(12) United States Patent
Nagasawa et al.

(10) Patent No.: US 7,880,005 B2
(45) Date of Patent: Feb. 1, 2011

(54) PROCESS FOR PRODUCING 5-METHYL-4,5,6,7-TETRAHYDROTHIAZOLO[5,4-C]PYRIDINE-2-CARBOXYLIC ACID

(75) Inventors: Hiroshi Nagasawa, Tokyo (JP); Koji Sato, Tokyo (JP); Tsutomu Yagi, Tokyo (JP); Yasuo Kitani, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 12/631,002

(22) Filed: Dec. 4, 2009

(65) Prior Publication Data

US 2010/0076192 A1    Mar. 25, 2010

Related U.S. Application Data

(60) Continuation of application No. 12/418,750, filed on Apr. 6, 2009, now Pat. No. 7,678,910, which is a division of application No. 10/578,844, filed as application No. PCT/JP2004/016874 on Nov. 12, 2004, now Pat. No. 7,547,786.

(30) Foreign Application Priority Data

| Nov. 12, 2003 | (JP) | ............................. 2003-382382 |
| Nov. 12, 2003 | (JP) | ............................. 2003-382383 |
| Nov. 12, 2003 | (JP) | ............................. 2003-382384 |

(51) Int. Cl.
   C07D 513/04    (2006.01)
(52) U.S. Cl. .................................................... 546/114
(58) Field of Classification Search ................. 546/114
   See application file for complete search history.

(56) References Cited

U.S. PATENT DOCUMENTS

| 4,289,524 A | 9/1981 | Belkind |
| 5,424,431 A | 6/1995 | Ohta et al. |
| 2004/0122063 A1 | 6/2004 | Yoshino et al. |
| 2005/0020645 A1 | 1/2005 | Ohta et al. |
| 2005/0119486 A1 | 6/2005 | Ohta et al. |
| 2005/0245563 A1 | 11/2005 | Boyle et al. |
| 2006/0252837 A1 | 11/2006 | Ohta et al. |

FOREIGN PATENT DOCUMENTS

| GB | 1140387 | 1/1969 |
| JP | 2001-294572 | 10/2001 |
| JP | 2003-104975 | 4/2003 |
| NL | 6610324 | 1/1967 |
| WO | WO 92/07849 | 5/1992 |
| WO | WO 01/62763 A1 | 8/2001 |
| WO | WO 01/74774 A1 | 10/2001 |
| WO | WO 03/000657 A1 | 1/2003 |
| WO | WO 03/000680 A1 | 1/2003 |
| WO | WO 03/016302 A1 | 2/2003 |
| WO | 2004/058715 | 7/2004 |
| WO | 2004/058728 | 7/2004 |
| WO | WO 2004/058715 A1 | 7/2004 |

OTHER PUBLICATIONS

Edited by Kagaku Daijiten Henshu Iinkai, reduced-side edition Kagaku Daijiten 6, Kyoritsu Shuppan Co., Ltd., Dec. 15, 1963, pp. 729-731. (with partial English translation).
Herkes, F. E. et al. "Perhalogenated Thiazoles. Their Synthesis, Reactions and Mass Spectra", Journal of Heterocyclic Chemistry, vol. 13, No. 6, pp. 1297-1304, Dec. 1976.
Paul A. Wender, et al., Methodology for the Facile and Regio-Controlled Synthesis of Indoles[1a,b], Tetrahedoron, vol. 39, No. 22, 1983, pp. 3767-3776.
Haginoya et al., "Facile Methods for Preparation, Etc.," Heterocycles, 63(7), 2004, pp. 1555-1561.

Primary Examiner—Patricia L Morris
(74) Attorney, Agent, or Firm—Oblon, Spivak, McClelland, Maier & Neustadt, L.L.P.

(57) ABSTRACT

5-Methyl-4,5,6,7-tetrahydrothiazolo[5,4-c]pyridine of formula (6) or a salt thereof,

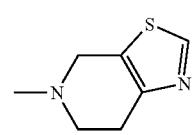

(6)

is prepared by reacting 2-amino-5-methyl-4,5,6,7-tetrahydrothiazolo[5,4-c]pyridine of formula (2) or a salt thereof,

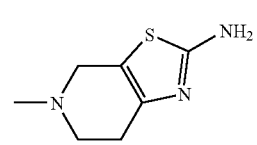

(2)

with an alkali metal nitrite in the presence of a reducing agent in an aqueous solution of an acidic compound.

3 Claims, No Drawings

PROCESS FOR PRODUCING 5-METHYL-4,5,6,7-TETRAHYDROTHIAZOLO [5,4-C]PYRIDINE-2-CARBOXYLIC ACID

CROSS REFERENCE TO RELATED APPLICATIONS

This application is a continuation application of prior U.S. application Ser. No. 12/418,750, filed Apr. 6, 2009, U.S. Pat. No. 7,678,910 the disclosure of which is incorporated herein by reference in its entirety The parent application is a divisional application of prior U.S. application Ser. No. 10/578,844, filed May 10, 2006, U.S. Pat. No. 7,547,786 which is the National Stage of PCT/JP 04/16874, filed Nov. 12, 2004, the disclosures of which are incorporated herein by reference in their entireties. The parent applications claim priority to Japanese Application Nos. 2003-382382, filed Nov. 12, 2003, JP 2003-382383, filed Nov. 12, 2003, and JP 2003-382384, filed Nov. 12, 2003, the disclosures of which are incorporated herein by reference in their entireties.

BACKGROUND OF THE INVENTION

1. Technical Field

The present invention relates to a process for producing intermediates of a useful compound which exhibits an inhibitory action on an activated coagulation factor X, and which is thus useful as a preventive/therapeutic drug for thrombus-related diseases.

2. Description of the Background

Compounds having a heterocyclic group and a diamine structure are known to be useful as preventive/therapeutic drugs for a variety of thrombus-related diseases, because they exhibit excellent inhibitory action against an activated coagulation factor (FXa) (Patent Documents 1 to 6, and others). For introducing a heterocyclic group into any of the above compounds, the compound of formula (5); i.e., 5-methyl-4,5,6,7-tetrahydrothiazolo[5,4-c]pyridine-2-carboxylic acid (hereinafter referred to as compound (5)):

[F1]

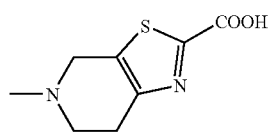

(5)

is an important intermediate.

In one process which has hitherto been known to produce compound (5), a piperidone derivative is treated with phosphorus sulfide to thereby form a thiazole ring, and then, a methyl group is introduced to the 5-position by use of lithium aluminum hydride, and the 2-position is converted to a lithium salt of carboxylic acid (see, for example, Patent Document 7). In another known process, a mercapto group which has been introduced into a protected aminopyridine is subjected to a ring formation reaction, followed by chemical reduction of the pyridine ring to thereby form a lithium salt of carboxylic acid (see, for example, Patent Document 1). In yet another known process, protected piperidone is first transformed into 2-amino-4,5,6,7-tetrahydrothiazolo[5,4-c]pyridine (hereinafter referred to as compound (2)) in the presence of a secondary amine by use of sulfur powder and cyanamide, then brominated with copper bromide(II) and alkyl nitrite, after which a methyl group is introduced to the 5-position by use of formaldehyde and triacetoxysodium borohydride, and the resultant 2-bromo-5-methyl-4,5,6,7-tetrahydrothiazolo [5,4-c]pyridine (hereinafter referred to as compound (3)) is transformed to a lithium salt of carboxylic acid (see, for example, Patent Document 1).

However, any of the above methods involves reactions that are difficult to manipulate when performed on an industrial scale, and includes a considerable number of steps because protection/deprotection steps are needed. Moreover, since chromatography is employed for purification, the overall production time is extended, which is industrially disadvantageous. Also, a compound (5) isolated as a lithium salt is highly hygroscopic, and therefore handling is difficult. Moreover, since the compound (5) lacks stability, storage-related problems arise.

In the meantime, compound (2) has been known to be obtained by reacting 1-methyl-4-piperidone (hereinafter referred to as compound (1)) with bromine (see for example, Patent Document 8).

However, use of bromine is industrially disadvantageous, as it is difficult to handle and places a great load on the environment. Moreover, during the process, a brominated compound must be isolated as an intermediate, which means that the process requires two steps.

Another method which has been known for preparing a compound (3) includes bromination of compound (2) with copper bromide (II) (see, for example, Patent Document 9). However, this method requires copper bromide (II) in an amount equal to or more than that of the compound (2). This makes it difficult to separate by-produced copper salts after the reaction, and chromatography is needed for purifying compound (3). Thus, the method is industrially disadvantageous.

[Patent Document 1] International Publication WO 01/74774 pamphlet
[Patent Document 2] International Publication WO 03/000680 pamphlet
[Patent Document 3] International Publication WO 03/016302 pamphlet
[Patent Document 4] International Publication WO 2004/058715 pamphlet
[Patent Document 5] International Publication WO 2004/058728 pamphlet
[Patent Document 6] International Publication WO 03/000657 pamphlet
[Patent Document 7] International Publication WO 01/62763 pamphlet
[Patent Document 8] Netherlands patent No. 6610324
[Patent Document 9] International Publication WO 92/07849 pamphlet

SUMMARY OF THE INVENTION

Problems to be Solved by the Invention

The object of the present invention is to provide a process for industrially producing, through use of inexpensive starting materials, intermediates of a useful compound which exhibits activated blood coagulation factor X inhibitory effect. The process enables efficient production of the intermediates with a fewer number of production steps.

Means for Solving the Problems

In order to solve the aforementioned problems, the present inventors have studied extensively and have found that (a) a compound (5) can efficiently be produced by subjecting a compound (3) to cyanation thereby giving 2-cyano-5-methyl-4,5,6,7-tetrahydrothiazolo[5,4-c]pyridine (compound (4)) and then hydrolyzing the compound (4); (b)—the compound (5) can be produced by subjecting a compound (2) to reduction and thereby giving 4,5,6,7-tetrahydrothiazolo[5,4-c]pyridine (compound 6) and then subjecting the compound (6) to trihalogenoacetylation and then to hydrolysis; and (c) the compound (2) can conveniently be produced from a compound (1) with a single step by use of a catalytic amount of a secondary amine, the compound (3) can be produced from the compound (2) without copper bromide (II), and each of the compounds (2) to (6) can be isolated, by treating with an acidic compound, as a stable salt with the acidic compound; and that, through use of any of these steps in combination, the compound (5) can be produced in an industrial scale with a small number of production steps. The present invention is accomplished based on the findings.

Accordingly, the present invention provides a process for producing a compound represented by formula (5) or a salt thereof:

[F4]

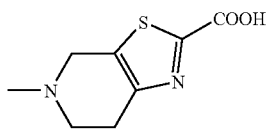

(5)

wherein the process is characterized by comprising reacting a compound represented by formula (3) or a salt thereof:

[F2]

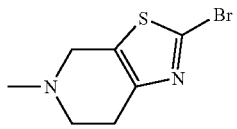

(3)

with a metal cyanide, to thereby obtain a compound represented by formula (4) or a salt thereof:

[F3]

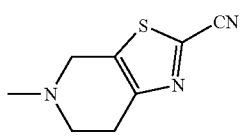

(4)

and hydrolyzing the obtained compound or a salt thereof.

The present invention also provides a process for producing a compound represented by formula (4) or a salt thereof:

[F6]

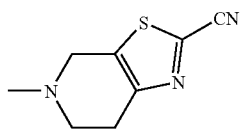

(4)

wherein the process is characterized by comprising reacting a compound represented by formula (3) or a salt thereof:

[F5]

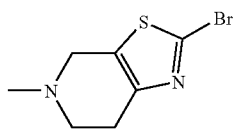

(3)

with a metal cyanide.

The present invention also provides a process for producing a compound represented by formula (5) or a salt thereof:

[F8]

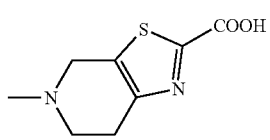

(5)

wherein the process is characterized by comprising hydrolyzing a compound represented by formula (4) or a salt thereof:

[F7]

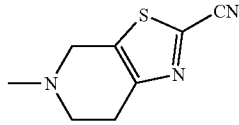

(4)

The present invention also provides a process for producing a compound represented by formula (5) or a salt thereof:

[F11]

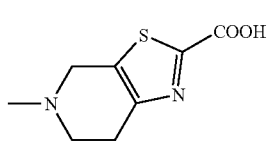

(5)

wherein the process is characterized by comprising reacting a compound represented by formula (2) or a salt thereof:

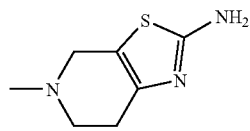 (2)

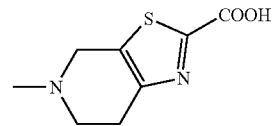 (5)

wherein the process is characterized by comprising reacting a compound represented by formula (6) or a salt thereof:

with an alkali metal nitrite in the presence of a reducing agent in an aqueous solution of an acidic compound, to thereby obtain a compound represented by formula (6) or a salt thereof:

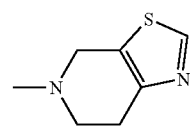 (6)

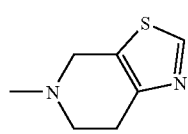 (6)

with trihalogenoacetyl halide in the presence of a base, followed by hydrolysis.

The present invention also provides a process for producing a compound represented by formula (5) or a salt thereof:

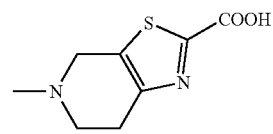 (5)

and reacting the obtained compound or a salt thereof with trihalogenoacetyl halide in the presence of a base, followed by hydrolysis.

The present invention also provides a process for producing a compound represented by formula (6) or a salt thereof:

wherein the process is characterized by comprising reacting a compound represented by formula (1) or a salt thereof:

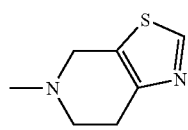 (6)

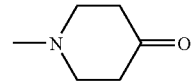 (1)

wherein the process is characterized by comprising reacting a compound represented by formula (2) or a salt thereof:

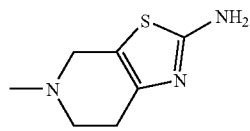 (2)

with sulfur powder and cyanamide in the presence of a secondary amine, to thereby obtain a compound represented by formula (2) or a salt thereof:

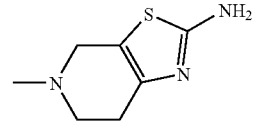 (2)

with an alkali metal nitrite in the presence of a reducing agent in an aqueous solution of an acidic compound.

The present invention also provides a process for producing a compound represented by formula (5) or a salt thereof:

and reacting the obtained compound or a salt thereof hydrobromic acid and alkali metal nitrite, to thereby obtain a compound represented by formula (3) or a salt thereof:

[F18]

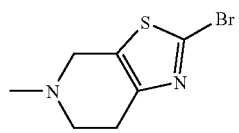
(3)

and reacting the obtained compound or a salt thereof with alkyllithium and carbon dioxide.

The present invention also provides a process for producing a compound represented by formula (2) or a salt thereof:

[F21]

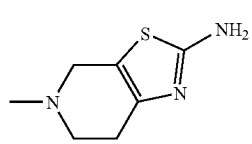
(2)

wherein the process is characterized by comprising reacting a compound represented by formula (1) or a salt thereof:

[F20]

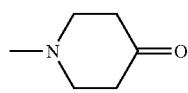
(1)

with sulfur powder and cyanamide in the presence of a secondary amine.

The present invention also provides a process for producing a compound represented by formula (3) or a salt thereof:

[F23]

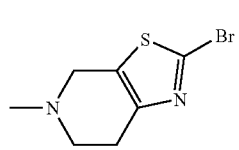
(3)

wherein the process is characterized by comprising reacting a compound represented by formula (2) or a salt thereof:

[F22]

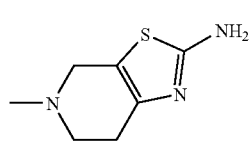
(2)

with hydrobromic acid and an alkali metal nitrite.

The present invention also provides a salt formed between an acidic compound and a compound represented by formula (4).

[F24]

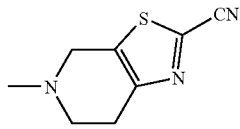
(4)

The present invention also provides a salt formed between an acidic compound and a compound represented by formula (5).

[F25]

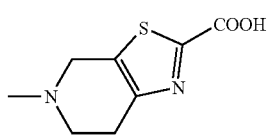
(5)

The present invention also provides a salt formed between an acidic compound and a compound represented by formula (6).

[F26]

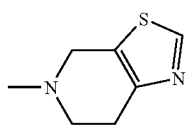
(6)

The present invention also provides a salt formed between an acidic compound and a compound represented by formula (2).

[F27]

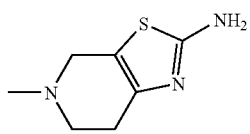
(2)

The present invention also provides a salt formed between an acidic compound and a compound represented by formula (3).

[F28]

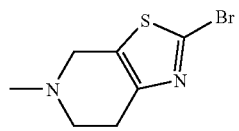
(3)

The present invention also provides a process for producing a compound represented by formula (8) or a salt thereof:

[F31]

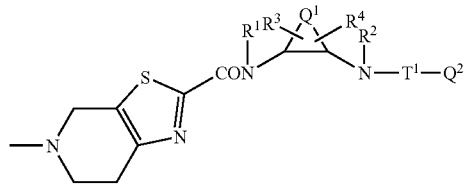
(8)

(wherein each of $R^1$ and $R^2$ represents a hydrogen atom, hydroxyl, alkyl or alkoxy; $Q^1$ represents C1-C8 alkylene, C2-C8 alkenylene, or —$(CH_2)_m$—$CH_2$-A-$CH_2$—$(CH_2)_n$— (wherein each of m and n represents 0 or an integer of 1 to 3 and A represents an oxygen atom, a nitrogen atom, a sulfur atom, —SO—, —$SO_2$—, —NH—, —O—NH—, —NH—NH—, —S—NH—, —SO—NH—, or $SO_2$—NH—);

each of $R^3$ and $R^4$, which is a substituent linked to a carbon atom, a nitrogen atom, or a sulfur atom forming the $Q^1$-containing ring, represents a hydrogen atom, hydroxyl, alkyl, alkenyl, alkynyl, a halogen atom, halogenoalkyl, cyano, cyanoalkyl, amino, aminoalkyl, N-alkylaminoalkyl, N,N-dialkylaminoalkyl, acyl, acylalkyl, acylamino which may have a substituent, alkoxyimino, hydroxyimino, acylaminoalkyl, alkoxy, alkoxyalkyl, hydroxyalkyl, carboxyl, carboxyalkyl, alkoxycarbonyl, alkoxycarbonylalkyl, alkoxycarbonylalkylamino, carboxyalkylamino, alkoxycarbonylamino, alkoxycarbonylaminoalkyl, carbamoyl, N-alkylcarbamoyl whose alkyl may or may not be substituted, N,N-dialkylcarbamoyl whose alkyl may or may not be substituted, N-alkenylcarbamoyl, N-alkenylcarbamoylalkyl, N-alkenyl-N-alkylcarbamoyl, N-alkenyl-N-alkylcarbamoylalkyl, N-alkoxycarbamoyl, N-alkyl-N-alkoxycarbamoyl, N-alkoxycarbamoylalkyl, N-alkyl-N-alkoxycarbamoylalkyl, carbazoyl which may be substituted by 1 to 3 alkyl groups, alkylsulfonyl, alkylsulfonylalkyl, 3- to 6-membered heterocyclic carbonyl which may have a substituent, carbamoylalkyl, N-alkylcarbamoylalkyl whose alkyl may or may not be substituted, N,N-dialkylcarbamoylalkyl whose alkyl may or may not be substituted, carbamoyloxyalkyl, N-alkylcarbamoyloxyalkyl, N,N-dialkylcarbamoyloxyalkyl, 3- to 6-membered heterocyclic carbonylalkyl which may have a substituent, 3- to 6-membered heterocyclic carbonyloxyalkyl which may have a substituent, aryl, aralkyl, 3- to 6-membered heterocyclic group which may have a substituent, 3- to 6-membered heterocyclic alkyl which may have a substituent, alkylsulfonylamino, arylsulfonylamino, alkylsulfonylaminoalkyl, arylsulfonylaminoalkyl, alkylsulfonylaminocarbonyl, arylsulfonylaminocarbonyl, alkylsulfonylaminocarbonylalkyl, arylsulfonylaminocarbonylalkyl, oxo, carbamoyloxy, aralkyloxy, carboxyalkyloxy, alkoxycarbonylalkyloxy, acyloxy, acyloxyalkyl, arylsulfonyl, alkoxycarbonylalkylsulfonyl, carboxyalkylsulfonyl, alkoxycarbonylacyl, alkoxyalkyloxycarbonyl, hydroxyacyl, alkoxyacyl, halogenoacyl, carboxyacyl, aminoacyl, acyloxyacyl, acyloxyalkylsulfonyl, hydroxyalkylsulfonyl, alkoxyalkylsulfonyl, 3- to 6-membered heterocyclic sulfonyl which may have a substituent, 3- to 6-membered heterocyclic oxy which may have a substituent, N-alkylaminoacyl, N,N-dialkylaminoacyl, N,N-dialkylcarbamoylacyl whose alkyl may or may not be substituted, N,N-dialkylcarbamoylalkylsulfonyl whose alkyl may or may not be substituted, alkylsulfonylacyl, N-arylcarbamoyl, N-3- to 6-membered heterocyclic carbamoyl, N-alkyl-N-arylcarbamoyl, N-alkyl-N-3- to 6-membered heterocyclic carbamoyl, N-arylcarbamoylalkyl, N-3- to 6-membered heterocyclic carbamoylalkyl, N-alkyl-N-arylcarbamoylalkyl, N-alkyl-N-3- to 6-membered heterocyclic carbamoylalkyl, aminocarbothioyl, N-alkylaminocarbothioyl, N,N-dialkylaminocarbothioyl, alkoxyalkyl(thiocarbonyl), alkylthioalkyl, or N-acyl-N-alkylaminoalkyl; when $R^3$ and $R^4$ are linked together to form a group, the group represents C1-C5 alkylene, C2-C5 alkenylene, C1-C5 alkylenedioxy, or carbonyldioxy;

$Q^2$ represents aryl which may have a substituent, arylalkenyl which may have a substituent, arylalkynyl which may have a substituent, heteroaryl which may have a substituent, heteroarylalkenyl which may have a substituent, a saturated or unsaturated bicyclic or tricyclic condensed hydrocarbon group which may have a substituent, or a saturated or unsaturated bicyclic or tricyclic condensed heterocyclic group which may have a substituent;

$T^1$ represents carbonyl, sulfonyl, —C(=O)—C(=O)—N(R')—, —C(=S)—C(=O)—N(R')—, —C(=O)—C(=S)—N(R')—, —C(=S)—C(=S)—N(R')— (wherein R' represents a hydrogen atom, hydroxyl, alkyl, or alkoxy), —C(=O)-$A^1$-N(R")— (wherein $A^1$ represents an C1-C5 alkylene which may have a substituent and R" represents a hydrogen atom, hydroxyl, alkyl, or alkoxy), —C(=O)—NH—, —C(=S)—NH—, —C(=O)—NH—NH—, —C(=O)-$A^2$-C(=O)— (wherein $A^2$ represents a single bond or C1-C5 alkylene), —C(=O)-$A^3$-C(=O)—NH— (wherein $A^3$ represents C1-C5 alkylene), —C(=O)—C(=$NOR^a$)—N($R^b$)—, —C(=S)—C(=$NOR^a$)—N($R^b$)— (wherein $R^a$ represents a hydrogen atom, alkyl, or alkanoyl and $R^b$ represents a hydrogen atom, hydroxyl, alkyl, or alkoxy), —C(=O)—N=N—, —C(=S)—N=N—, —C(=$NOR^c$)—C(=O)—N($R^d$)— (wherein $R^C$ represents a hydrogen atom, alkyl, alkanoyl, aryl, or aralkyl and $R^d$ represents a hydrogen atom, hydroxyl, alkyl, or alkoxy), —C(=N—N($R^e$)($R^f$))—C(=O)—N($R^g$)— (wherein, each of $R^e$ and $R^f$ represents a hydrogen atom, alkyl, alkanoyl, or alkyl(thiocarbonyl) and $R^g$ represents a hydrogen atom, hydroxyl, alkyl, or alkoxy), —C(=O)—NH—C(=O)—, —C(=S)—NH—C(=O)—, —C(=O)—NH—C(=S)—, —C(=S)—NHC(=S)—, —C(=O)—NH—$SO_2$—, —$SO_2$—NH—, —C(=NCN)—NH—C(=O)—, —C(=S)—C(=O)—, or thiocarbonyl), wherein the process is characterized by comprising reacting a compound which is represented by formula (5) and which is produced through any of the above processes or a salt thereof:

[F29]

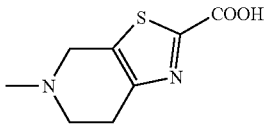
(5)

with diamines represented by formula (7) or a salt thereof:

[F30]

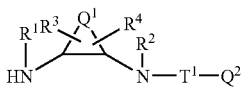
(7)

(wherein $R^1$, $R^2$, $R^3$, $R^4$, $T^1$, $Q^1$, and $Q^2$ have the same meanings as described above).

The present invention also provides a process for producing a compound represented by formula (8) or a salt thereof:

[F37]

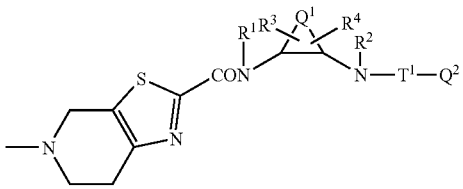
(8)

(wherein $R^1$, $R^2$, $R^3$, $R^4$, $T^1$, $Q^1$, and $Q^2$ have the same meanings as described above), wherein the process is characterized by comprising reacting a compound which is represented by formula (5) and which is produced through any of the above processes or a salt thereof:

[F32]

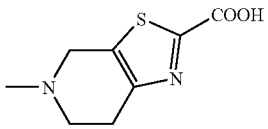
(5)

with diamines represented by formula (9) or a salt thereof:

[F33]

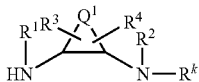
(9)

(wherein $R^k$ is an amino-group-protective group and $R^1$, $R^2$, $R^3$, $R^4$, and $Q^1$ have the same meanings as described above) to thereby obtain a compound represented by formula (10):

[F34]

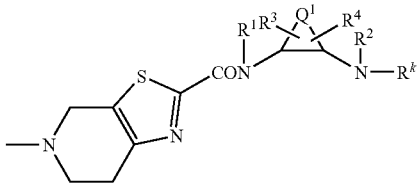
(10)

(wherein $R^1$, $R^2$, $R^3$, $R^4$, $Q^1$, and $R^K$ have the same meanings as described above), and removing $R^k$ from the obtained compound or a salt thereof, to thereby produce a compound represented by formula (11) or a salt thereof:

[F35]

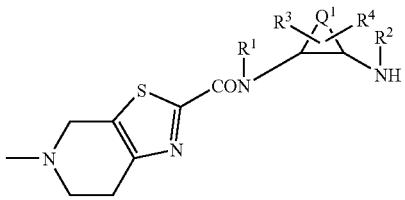
(11)

(wherein $R^1$, $R^2$, $R^3$, $R^4$, and $Q^1$ have the same meanings as described above), and reacting the obtained compound or a salt thereof with a compound represented by formula (12) or a salt thereof:

$$HO\text{-}T^1\text{-}Q^2 \qquad (12)$$

(wherein $T^1$ and $Q^2$ have the same meanings as described above).

The present invention also provides a process for producing a compound represented by formula (8'):

[F43]

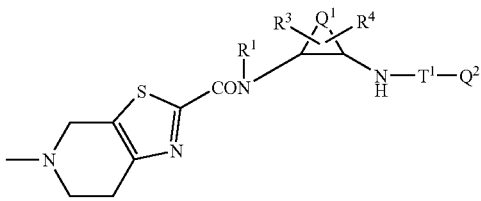
(8')

(wherein $R^1$, $R^3$, $R^4$, $T^1$, $Q^1$, and $Q^2$ have the same meanings as described above), wherein the process is characterized by comprising reacting a compound which is represented by formula (5) and which is produced through any of the above processes or a salt thereof:

[F38]

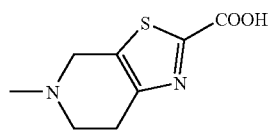

(5)

with diamines represented by formula (13) or a salt thereof:

[F39]

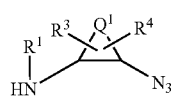

(13)

(wherein $R^1$, $R^3$, $R^4$, and $Q^1$ have the same meanings as described above) to thereby obtain a compound represented by formula (14) or a salt thereof:

[F40]

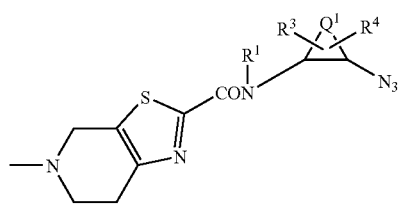

(14)

(wherein $R^1$, $R^3$, $R^4$, and $Q^1$ have the same meanings as described above), and reducing the obtained compound or a salt thereof, to thereby yield a compound represented by formula (11') or a salt thereof:

[F41]

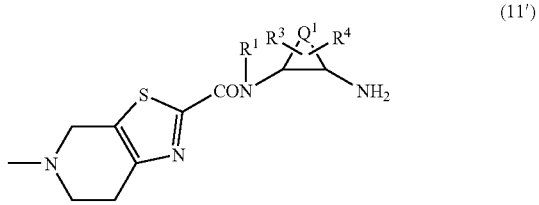

(11')

(wherein $R^1$, $R^3$, $R^4$, and $Q^1$ have the same meanings as described above), and reacting the obtained compound or a salt thereof with a compound represented by formula (12) or a salt thereof:

$$HO\text{-}T^1\text{-}Q^2 \quad (12)$$

(wherein $T^1$ and $Q^2$ have the same meanings as described above).

EFFECTS OF THE INVENTION

The processes of the present invention enable production of a compound (5) in an industrially advantageous manner. Through use of the processes of the present invention, a compound which exhibits excellent FXa inhibitory effect and thus is useful as a preventive/therapeutic drug for thrombotic diseases can be produced in an industrially advantageous manner.

DETAILED DESCRIPTION OF THE PREFERRED EMBODIMENTS

The processes for producing the compound (5) according to the present invention are represented by the following reaction scheme and will next be described.

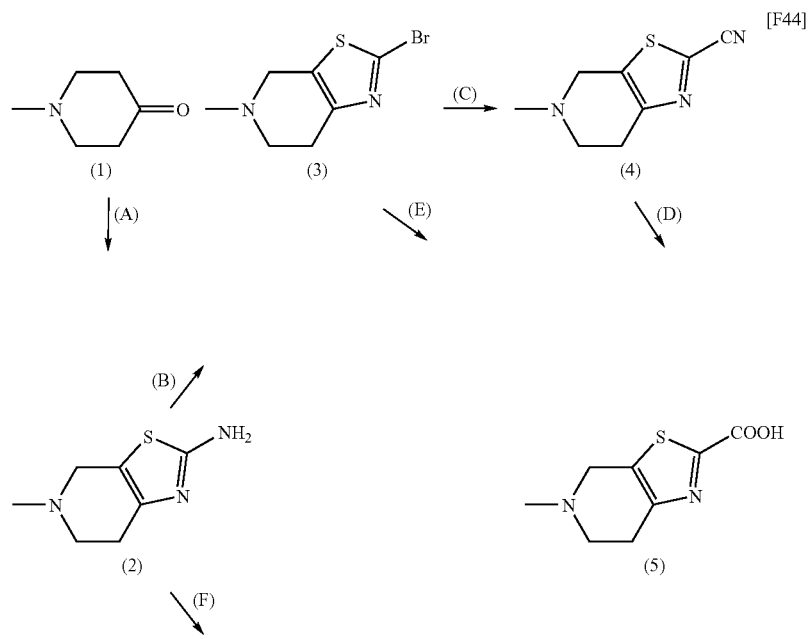

-continued

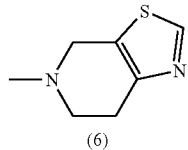

(G)

(6)

Step (A): 1-Methyl-4-piperidone (1) or a salt thereof is reacted, in the presence of a secondary amine, with a sulfur powder and a cyanamide, to thereby produce a compound (2) or a salt thereof. The compound (1) may be prepared through, for example, methylation of 4-piperidone by use of a conventional method.

The cyanamide is preferably used in an amount of 1 to 2 equivalents, more preferably 1 equivalent on the basis of 1 mole of the compound (1). The sulfur powder is preferably used in an amount of 1 to 2 equivalents, more preferably 1 equivalent on the basis of 1 male of the compound (1). No particular limitation is imposed on the secondary amine. Examples of the secondary amine include diethylamine, diisopropylamine, pyrrolidine, piperidine, and morpholine, with pyrrolidine being preferred. The amount of secondary amine added may be a catalytic amount, preferably 0.01 to 1.2 equivalents, more preferably 0.1 to 0.5 equivalents, still more preferably 0.1 equivalents on the basis of 1 mole of the compound (1).

No particular limitation is imposed on the reaction solvent, so long as the solvent is inert with respect to the reaction. Examples of the solvent which may be employed include alcoholic solvents such as methanol, ethanol, and 2-propanol; ether solvents such as diethyl ether, tetrahydrofuran, and 1,4-dioxane; acetonitrile; and acetic acid alkyl ester solvents such as ethyl acetate and isopropyl acetate. Among these solvents, alcoholic solvents are preferred, with 2-propanol being more preferred.

The reaction temperature, which differs depending on the solvent to be employed, typically falls within a range of 0° C. to the boiling point of the solvent, preferably a range of 45° C. to the boiling point of the solvent. The reaction is carried out for about 1 to 24 hours, preferably about 2 to 5 hours until virtually completion.

The reaction mixture may be directly subjected to filtration to isolate the compound (2) as crystals. Alternatively, when the compound (2) is to be isolated in the form of a salt, an acidic compound is added to the reaction mixture. The "acidic compound" refers to a compound which, as itself, is acidic, or which, when being dissolved in water, is acidic. Examples of the acidic compound which may be employed include organic carboxylic acids such as oxalic acid, acetic acid, benzoic acid, p-nitrobenzoic acid, malic acid, tartaric acid, succinic acid, maleic acid, and fumaric acid; organic sulfonic acids such as p-toluenesulfonic acid, and methanesulfonic acid; and inorganic acids such as hydrochloric acid, hydrobromic acid, sulfuric acid, and phosphoric acid. Among these acidic compounds, hydrobromic acid is preferred.

Step (B): The compound (2) or a salt thereof is reacted, in the presence of hydrobromic acid, with an alkali metal nitrite, to thereby give a compound (3) or a salt thereof.

Examples of the alkali metal nitrite which may be employed include sodium nitrite, potassium nitrite, and lithium nitrite, with sodium nitrite being preferred. The alkali metal nitrite is preferably used in an amount of 1 to 3 equivalents, more preferably 1.5 equivalents on the basis of 1 mole of the compound (2).

The reaction is performed at a temperature falling within a range of −20 to 100° C., preferably −5 to 15° C. for about 1 to 36 hours, preferably 3 to 24 hours until virtually completion.

The compound (2) may be isolated through addition of an aqueous solution of an alkali metal hydroxide (e.g., sodium hydroxide, potassium hydroxide, or lithium hydroxide) or an alkaline earth metal hydroxide (e.g., calcium hydroxide or barium hydroxide), preferably aqueous sodium hydroxide, for alkalifying the mixture (about pH 12 to 13); extraction of the mixture through use of a suitable solvent; and evaporation under reduced pressure.

No particular limitation is imposed on the solvent employed for extraction. Examples of the extraction solvent include ether solvents such as diethyl ether, diisopropyl ether, and methyl tert-butyl ether; aromatic hydrocarbon solvents such as benzene and toluene; and acetic acid alkyl ester solvents such as ethyl acetate and isopropyl acetate. Among these solvents, aromatic hydrocarbon solvents are preferred, with toluene being more preferred.

The compound (3) may be isolated in the form of a salt through dissolution in a suitable solvent and treatment with an acidic compound. Examples of the acidic compound include the same compounds as described above. Of these, p-toluenesulfonic acid is preferred.

No particular limitation is imposed on the solvent. Examples of the solvent which may be employed include alcoholic solvents such as methanol, ethanol, and 2-propanol; ether solvents such as diethyl ether, tetrahydrofuran, and 1,4-dioxane; aromatic hydrocarbon solvents such as benzene and toluene; acetonitrile; and acetic acid alkyl ester solvents such as ethyl acetate and isopropyl acetate. Among these solvents, alcoholic solvents are preferred, with methanol being more preferred.

Step (C): The compound (3) or a salt thereof is reacted with a metal cyanide, to thereby give 2-cyano-5-methyl-4,5,6,7-tetrahydrothiazolo[5,4-c]pyridine (hereinafter referred to as "compound (4)") or a salt thereof.

Examples of the metal cyanide include sodium cyanide, potassium cyanide, lithium cyanide, copper cyanide, and zinc cyanide. These metal cyanides may be employed in combination of two or more species, and a combination of sodium cyanide and copper cyanide is preferred. The metal cyanide is preferably used in an amount of 1 to 3 equivalents, more preferably 1.5 equivalents on the basis of 1 mole of the compound (3).

No particular limitation is imposed on the reaction solvent, so long as the solvent is inert with respect to the reaction. Examples of the reaction solvent include amide solvents such as N,N-dimethylformamide and N,N-dimethylacetamide;

aromatic hydrocarbon solvents such as benzene and toluene; and dimethyl sulfoxide. Of these, N,N-dimethylacetamide is preferred.

The reaction temperature falls within a range of 0 to 200° C., preferably 140 to 160° C. The reaction is performed for about 8 to 48 hours, preferably 13 to 20 hours until virtually completion.

The thus-obtained compound (4) may be isolated through addition of aqueous sodium hydrogencarbonate or a similar solution; extraction with a suitable solvent; evaporation under reduced pressure.

No particular limitation is imposed on the extraction solvent. Examples of the extraction solvent which may be employed include ether solvents such as diethyl ether, diisopropyl ether, and methyl tert-butyl ether; aromatic hydrocarbon solvents such as benzene and toluene; and acetic acid alkyl ester solvents such as ethyl acetate and isopropyl acetate. Among these solvents, aromatic hydrocarbon solvents are preferred, with toluene being more preferred.

Alternatively, the compound (4) may be isolated in the form of a salt of an acidic compound. Examples of the acidic compound include the same as described above. Of these acidic compounds, hydrochloric acid is preferred.

Step (D): The compound (4) or a salt thereof is hydrolyzed, to thereby give a compound (5) or a salt thereof.

The hydrolysis may be carried out by dissolving the compound (4) in a suitable solvent and treating the solution with an aqueous solution of an alkali metal hydroxide. Examples of the alkali metal hydroxide include sodium hydroxide, lithium hydroxide, and potassium hydroxide, with lithium hydroxide being preferred. Examples of the solvent which may be employed include alcoholic solvents such as ethanol, methanol, and 2-propanol, acetone, and acetonitrile, with ethanol being preferred.

The reaction temperature falls within a range of 0° C. to the boiling point of the solvent, preferably 40 to 70° C. The reaction is performed until virtually completion, for about 1 to 24 hours, preferably 5 to 10 hours.

The compound (5) may be isolated in the form of a salt through addition of an acidic compound to the reaction mixture. Examples of the acidic compound include the same as described above. Of these, hydrochloric acid is preferred.

Step (E): The compound (3) or a salt thereof is reacted with an alkyllithium and carbon dioxide gas, to thereby give a compound (5) or a salt thereof.

The reaction consists of two sub-steps. The first sub-step is lithiation through use of an alkyllithium. The alkyllithium is used preferably in an amount of 1 to 2 equivalents, more preferably 1 to 1.2 equivalents on the basis of 1 mole of the compound (3). The alkyllithium is preferably n-butyllithium. The reaction temperature falls within a range of −78° C. to the boiling point of the solvent, preferably −78 to 0° C. The reaction is performed for several minutes to 24 hours, preferably several minutes to 2 hours until virtually completion.

The second sub-step is a reaction between the lithium salt obtained in the first sub-step and carbon dioxide gas. Specifically, carbon dioxide is injected to the reaction mixture obtained through the above lithiation, or the reaction system is placed in a carbon dioxide atmosphere. The reaction temperature falls within a range of −78° C. to the boiling point of the solvent, preferably −78 to 0° C. The reaction is performed until virtually completion, for several minutes to 24 hours, preferably several minutes to 2 hours. Preferably, in the step (E), the sub-steps are both carried out under nitrogen, argon, or a similar inert gas.

No particular limitation is imposed on the reaction solvent, so long as the solvent is inert with respect to reaction. Examples of the reaction solvent include ether solvents such as methyl tert-butyl ether, diisopropyl ether, tetrahydrofuran, and 1,4-dioxane; linear of cyclic saturated hydrocarbon solvents such as n-hexane, n-heptane, and cyclohexane; and aromatic hydrocarbon solvents such as benzene and toluene. Among these solvents, ether solvents are preferred, with tetrahydrofuran being more preferred.

The compound (5) may be isolated in the form of a lithium salt by directly subjecting the reaction mixture to filtration. However, a lithium salt of the compound (5) is unstable. Therefore, preferably, the lithium salt is transformed into a free carboxylic acid, or, alternatively, a suitable second solvent is added to the resultant free carboxylic acid, and the solution is treated with an acidic compound, to thereby isolate the compound (5) as a salt. Examples of the acidic compound include the same as described above, with hydrochloric acid being preferred.

No particular limitation is imposed on the second solvent. Examples of the second solvent which may be employed include alcoholic solvents such as methanol, ethanol, and 2-propanol; acetonitrile; and acetic acid alkyl ester solvents such as ethyl acetate and isopropyl acetate. Among these solvents, alcoholic solvents are preferred, with methanol being more preferred.

Step (F): The compound (2) or a salt thereof is reacted with an alkali metal nitrite in the presence of a reducing agent in an aqueous solution of an acidic compound, to thereby give a compound (6) or a salt thereof.

Examples of the acidic compound include the same compounds as described above, with sulfuric acid being preferred.

Examples of the reducing agent include hydrogen, sodium borohydride, hypophosphorous acid, and formic acid, with hypophosphorous acid being preferred. Examples of the alkali metal nitrite include sodium nitrite, potassium nitrite, and lithium nitrite, with sodium nitrite being preferred.

The reducing agent is used preferably in an amount of 1 to 3 equivalents, more preferably 2 equivalents on the basis of 1 mole of the compound (2). The alkali metal nitrite is preferably used in an amount of 1 to 3 equivalents, more preferably 2 equivalents on the basis of 1 mole of the compound (2). The reaction is performed at a temperature falling within a range of −20 to 50° C., preferably −5 to 15° C., for about 1 to 36 hours, preferably 1 to 24 hours.

The compound (6) may be isolated through addition of an aqueous solution of an alkali metal hydroxide (e.g., sodium hydroxide, potassium hydroxide, lithium hydroxide), preferably an aqueous lithium hydroxide solution for alkalifying the mixture (pH 12 to 13 or thereabouts); extraction through use of a suitable solvent; and evaporation under reduced pressure.

No particular limitation is imposed on the extraction solvent. Examples of the extraction solvent which may be employed include ether solvents such as diethyl ether, diisopropyl ether, and methyl tert-butyl ether; aromatic hydrocarbon solvents such as benzene and toluene; acetic acid alkyl ester solvents such as ethyl acetate and isopropyl acetate; and halohydrocarbon solvents such as dichloromethane and chloroform. Among these solvents, acetic acid alkyl ester solvents and halohydrocarbon solvents are preferred, with ethyl acetate being more preferred.

Alternatively, the compound (6) may be isolated in the form of a salt through addition of an acidic compound in a suitable solvent. No particular limitation is imposed on the solvent. Examples of the solvent which may be employed include alcoholic solvents such as methanol, ethanol, and 2-propanol; ether solvents such as diethyl ether, tetrahydrofuran, and 1,4-dioxane; aromatic hydrocarbon solvents such as benzene and toluene; acetonitrile; and acetic acid alkyl ester solvents such as ethyl acetate and isopropyl acetate. Among these solvents, alcoholic solvents are preferred, with 2-propanol being more preferred.

Examples of the acidic compound include the same compound as described above, with p-toluene sulfonic acid being preferred.

Step (G): The compound (6) or a salt thereof is reacted with a trihalogenoacetyl halide in the presence of a base, followed by hydrolysis, to thereby give a compound (5) or a salt thereof.

The trihalogenoacetyl halide is preferably used in an amount of 1 to 3 equivalents, more preferably 2 equivalents on the basis of 1 mole of the compound (6). Examples of the trihalogenoacetyl halide include tribromoacetyl chloride and trichloroacetyl chloride, with trichloroacetyl chloride being preferred. No particular limitation is imposed on the base. Examples of the base which may be employed include tertiary amines such as triethylamine, diisopropylethylamine, and N-methylmorpholine; alkali metal hydroxides such as sodium hydroxide, potassium hydroxide, and lithium hydroxide; and inorganic bases such as carbonic acid salt and hydrogen carbonic acid salt. Among these bases, tertiary amines are preferred, and triethylamine, diisopropylethylamine, and N-methylmorpholine are more preferred. The base is preferably used in an amount of 1 to 3 equivalents, more preferably 2 equivalents on the basis of 1 mole of the compound (6).

No particular limitation is imposed on the reaction solvent. Examples of the reaction solvent which may be employed include ether solvents such as diethyl ether, tetrahydrofuran, and 1,4-dioxane; aromatic hydrocarbon solvents such as benzene and toluene; amide solvents such as N,N-dimethylformamide and N,N-dimethylacetamide; dimethyl sulfoxide; acetonitrile; and acetic acid alkyl ester solvents such as ethyl acetate and isopropyl acetate. Among these solvents, aromatic hydrocarbon solvents such as toluene and acetic acid alkyl ester solvents such as ethyl acetate and isopropyl acetate are preferred, and toluene, ethyl acetate, and isopropyl acetate are more preferred.

The reaction temperature, which differs depending on the solvent to be employed, typically falls within a range of −78° C. to the boiling point of solvent, preferably 0° C. to the boiling point of solvent. The reaction is performed for about 1 to 24 hours, preferably 1 to 5 hours until virtually completion.

The hydrolysis may be continuously performed through addition of an aqueous solution of an alkali metal hydroxide to the reaction mixture. Examples of the alkali metal hydroxide include sodium hydroxide, lithium hydroxide, and potassium hydroxide, with lithium hydroxide being preferred.

The reaction temperature typically falls within a range of −5° C. to the boiling point of the solvent, preferably 0° C. to the boiling point of the solvent. The reaction is performed for about 1 to 10 hours, preferably 1 to 5 hours until virtually completion.

After completion of hydrolysis, the organic layer and the aqueous layer are partitioned with each other, whereby the compound (5) is collected in the aqueous layer, and oil-soluble impurities or other oil-soluble substances are removed to the organic layer. The thus-collected compound (5) may be isolated in the form of a salt through evaporation of the aqueous layer, addition of a suitable second solvent, and addition of an acidic compound.

No particular limitation is imposed on the second solvent. Examples of the second solvent which may be employed include alcoholic solvents such as methanol, ethanol, and 2-propanol; acetonitrile; and acetic acid alkyl ester solvents such as ethyl acetate and isopropyl acetate. Among these solvents, alcoholic solvents are preferred, and methanol is particularly preferred.

Examples of the acidic compound include the same compounds as described above, with hydrochloric acid being preferred.

Next will be described a process for producing, from the compound (5), a compound (8) which is useful as a preventive/therapeutic agent for thrombotic diseases. The compound (8) may be produced from the compound (5) through a process described in International Publication WO 2004/058715 pamphlet, or a similar process. A representative process represented by the following reaction scheme will next be described:

[F45]

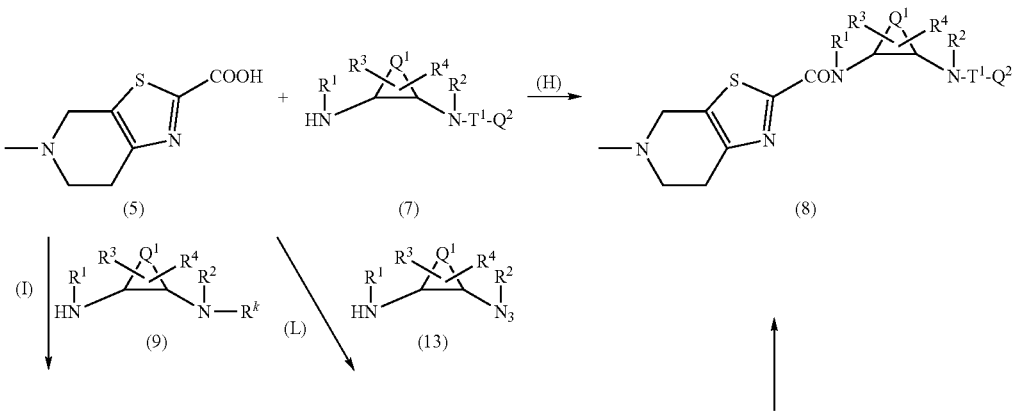

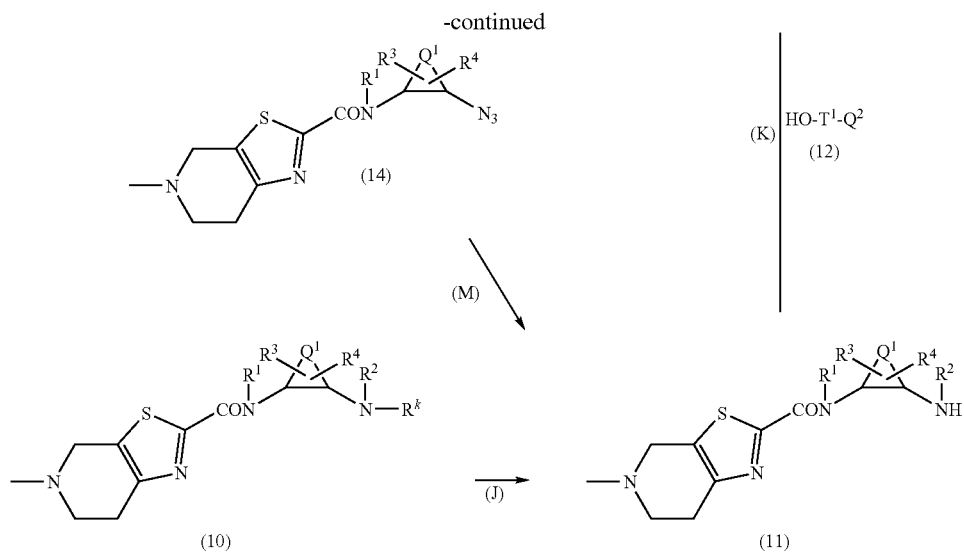

(wherein $R^1$, $R^2$, $R^3$, $R^4$, $R^k$, $T^1$, $Q^1$, and $Q^2$ have the same meanings as described above).

Step (H): The compound (5) or a salt thereof is reacted with a diamine compound (7) or a salt thereof, to thereby give a compound (8) or a salt thereof.

The compound (5) may be transformed, prior to being subjected to the reaction, to a mixed acid anhydride, an acid halide, or an active ester, according to needs. The transformation reaction may be performed through use of a reagent under conditions, the reagent and the conditions being usually employed in a peptide synthesis. When the compound (5) is transformed to a mixed acid anhydride, for example, the compound (5) may be reacted with a chloroformate such as ethyl chloroformate or isobutyl chloroformate in the presence of a base. When the compound (5) is transformed to an acid halide, the compound (5) may be treated with an acid halide such as thionyl chloride or oxalyl chloride. A variety of active esters can be produced. For example, the compound (5) may reacted with a phenol compound such as p-nitrophenol or with N-hydroxybenzotriazole, N-hydroxysuccinimide, or a similar compound through use of a condensing agent such as N,N'-dicyclohexylcarbodiimide or 1-ethyl-3-(3-dimethylaminopropyl)carbodiimide hydrochloride. Alternatively, an active ester of the compound (5) may be produced, among others, by reacting the compound (5) with pentafluorophenyl trifluoroacetate or a similar compound, by reacting the compound (5) with 1-benzo triazolyloxytripyrrolidinophosphonium hexafluorophosphite, by reacting the compound (5) with diethyl cyanophosphate (the Shioiri method), or by reacting the compound (5) with triphenylphosphine and 2,2'-dipyridyldisulfide (the Mukaiyama method). The thus-obtained mixed acid anhydride, acid halide, or active ester of the compound (5) is reacted with a diamine compound (7) in the presence of a suitable base in an inert solvent at a temperature of −78° C. to 150° C., to thereby give a compound (8).

Specific examples of the base employed in the above-described step (H) include carbonates of alkali metals and alkaline earth metals, alkali metal alkoxides, alkali metal hydroxides, and hydrides (e.g., sodium carbonate, and potassium carbonate, sodium ethoxide, potassium butoxide, sodium hydroxide, potassium hydroxide, sodium hydroxide, and potassium hydroxide); alkyllithiums such as n-butyl lithium; organometallic bases such as dialkylamino lithium (e.g., lithium diisopropylamide); bissilylamine organometallic bases such as lithium bis(trimethylsilyl)amide; and organic bases such as pyridine, 2,6-lutidine, collidine, 4-dimethylaminopyridine, triethylamine, N-methylmorpholine, diisopropylethylamine, and diazabicyclo[5.4.0]undec-7-ene (DBU).

Examples of the inert solvent which is employed in the reaction include haloalkyl solvents such as dichloromethane, chloroform, and carbon tetrachloride; ether solvents such as tetrahydrofuran, 1,2-dimethoxyethane, and dioxane; aromatic solvents such as benzene and toluene; amide solvents such as N,N-dimethylformamide, N,N-dimethylacetamide, and N-methylpyrrolidin-2-one. Additionally, in some cases, there may be employed sulfoxide solvents such as dimethyl sulfoxide, and sulfolane; and ketone solvents such as acetone and methyl ethyl ketone.

Step (I): The compound (5) or a salt thereof is reacted with a diamine compound (9) or a salt thereof, to thereby give a compound (10) or a salts thereof. Examples of a protection group for the amino group, represented by $R^k$, include alkanoyls such as acetyl; alkoxycarbonyls such as methoxycarbonyl, ethoxycarbonyl, and tert-butoxycarbonyl; arylmethoxycarbonyls such as benzyloxycarbonyl, paramethoxybenzyloxycarbonyl, and p-(or o-)nitrobenzyloxycarbonyl; benzyls; arylmethyls such as triphenylmethyl; aroyl such as benzoyl; and arylsulfonyls such as 2,4-dinitrobenzenesulfonyl and orthonitrobenzenesulfonyl. The reaction of the compound (5) and the diamine compound (9) may be performed in a manner similar to that described in relation to the step (H).

Step (J): The compound (10) or a salt thereof is deprotected through removal of the protection group ($R^k$), to thereby give a compound (11) or a salt thereof. The deprotection reaction may be performed through use of a reagent under conditions, the reagent and the conditions being usually selected in accordance with the type of the protection group. For example, when the protection group is a tert-butoxycarbonyl group, the compound (10) or a salt thereof may be treated at a temperature of −20 to 70° C. with trifluoroacetic acid or a similar substance.

Step (K): The compound (11) or a salt thereof is reacted with a compound (12) or a salt thereof, to thereby give a compound (8) or a salt thereof. The reaction may be performed in a manner similar to that described above in relation to the step (H).

Step (L): The compound (5) or a salt thereof is reacted with a compound (13) or a salt thereof, to thereby give a compound (14) or a salt thereof. In the reaction, $R^1$ is preferably a hydrogen atom.

The reaction may be performed in a manner similar to that described above in relation to step (I) or (H).

Step (M): The compound (14) or a salt thereof is reduced, to thereby give a compound (11) or a salt thereof in which $R^2$ in formula (11) is a hydrogen atom. The reduction may be performed through catalytic reduction in the presence of a catalyst such as platinum or palladium through, if necessary, pressurization.

It should be noted that the starting materials of steps (I) to (M); i.e., the compounds (7), (9), (12), and (13) may be obtained through a method described in International Publication WO 2004/058715 pamphlet.

Next will be described the substituents of the compound represented by formula (8).

<Group $Q^2$>

$Q^2$ means an aryl group which may have a substituent, an arylalkenyl group which may have a substituent, an arylalkynyl group which may have a substituent, an heteroaryl group which may have a substituent, an heteroarylalkenyl group which may have a substituent, a saturated or unsaturated bicyclic or tricyclic fused hydrocarbon group which may have a substituent, or a saturated or unsaturated bicyclic or tricyclic fused heterocyclic group which may have a substituent.

In group $Q^2$, examples of the aryl group include C6-C14 aryl groups such as phenyl, naphthyl, anthryl, and phenanthryl. The arylalkenyl is a group composed of a C6-C14 aryl group and a C2-C6 alkenylene group, and specific examples include a styryl group. The arylalkynyl group is a group composed of a C6-C14 aryl group and a C2-C6 alkynylene group, and specific examples include a phenylethynyl group.

The heteroaryl group is a monovalent aromatic group having at least one heteroatom selected from among an oxygen atom, a sulfur atom, and a nitrogen atom. Specific examples include heteroaryl groups having a total number of ring-forming atoms of 5 or 6 such as pyridyl, pyridazinyl, pyrazinyl, furyl, thienyl, pyrrolyl, thiazolyl, oxazolyl, pyrimidinyl, and tetrazolyl. The heteroarylalkenyl group is a group composed of the above heteroaryl group and a C2-C6 alkenylene group, and specific examples include thienylethenyl and pyridylethenyl.

The saturated or unsaturated bicyclic or tricyclic condensed hydrocarbon group is a monovalent group derived from saturated or unsaturated bicyclic or tricyclic condensed hydrocarbon. The saturated or unsaturated bicyclic or tricyclic condensed hydrocarbon is a bicyclic or tricyclic condensed hydrocarbon which is formed through condensation of 2 or 3 saturated or unsaturated 5- or 6-membered cyclic hydrocarbons which may be identical to or different from one another. Examples of the saturated or unsaturated 5- or 6-membered cyclic hydrocarbon include cyclopentane, cyclopentene, cyclohexane, cyclohexene, cyclohexadiene, and benzene. Specific examples of the saturated or unsaturated bicyclic or tricyclic condensed hydrocarbon include indenyl, indanyl, tetrahydronaphthyl, and naphthyl. No particular limitation is imposed on the position, in the saturated or unsaturated bicyclic or tricyclic condensed hydrocarbon group, to which $T^1$ is linked.

The saturated or unsaturated bicyclic or tricyclic condensed heterocyclic group refers to a monovalent group derived from saturated or unsaturated bicyclic or tricyclic condensed heterocyclic ring. The term "saturated or unsaturated bicyclic or tricyclic condensed heterocyclic ring" refers to any of the following compounds 1) to 3):

1) bicyclic or tricyclic condensed heterocyclic ring which is formed through condensation of 2 or 3 saturated or unsaturated 5- to 7-membered heterocyclic rings which may be identical to or different from one another, 2) bicyclic or tricyclic condensed heterocyclic ring which is formed through condensation of one saturated or unsaturated 5- to 7-membered heterocyclic ring and 1 or 2 saturated or unsaturated 5- or 6-membered cyclic hydrocarbons, and 3) tricyclic condensed heterocyclic ring which is formed through condensation of 2 saturated or unsaturated 5- to 7-membered heterocyclic rings and one saturated or unsaturated 5- or 6-membered cyclic hydrocarbon.

No particular limitation is imposed on the position, in the aforementioned saturated or unsaturated bicyclic or tricyclic condensed heterocyclic group, to which $T^1$ is linked.

The aforementioned saturated or unsaturated 5- to 7-membered heterocyclic ring refers to a heterocyclic ring having at least one heteroatom selected from an oxygen atom, a sulfur atom, and a nitrogen atom. Specific examples include furan, pyrrole, thiophene, pyrazole, imidazole, oxazole, oxazolidine, thiazole, thiadiazole, furazane, pyran, pyridine, pyrimidine, pyridazine, pyrrolidine, piperazine, piperidine, oxazine, oxadiazine, morpholine, thiazine, thiadiazine, thiomorpholine, tetrazole, triazole, triazine, thiadiazine, oxadiazine, azepine, diazepine, triazepine, thiazepine, and oxazepine.

The saturated or unsaturated 5- or 6-membered cyclic hydrocarbon includes the same as exemplified in relation to the saturated or unsaturated bicyclic or tricyclic condensed hydrocarbon group. Specific examples of the saturated or unsaturated bicyclic or tricyclic condensed heterocyclic group include benzofuryl, isobenzofuryl, benzothienyl, indolyl, indolinyl, isoindolyl, isoindolinyl, indazolyl, quinolyl, dihydroquinolyl, 4-oxodihydroquinolyl(dihydroquinolin-4-one), tetrahydroquinolyl, isoquinolyl, tetrahydroisoquinolyl, chromenyl, chromanyl, isochromanyl, 4H-4-oxobenzopyranyl, 3,4-dihydro-4H-4-oxobenzopyranyl, 4H-quinolizinyl, quinazolinyl, dihydroquinazolinyl, tetrahydroquinazolinyl, quinoxalinyl, tetrahydroquinoxalinyl, cinnolinyl, tetrahydrocinnolinyl, indolizinyl, tetrahydroindolizinyl, benzothiazolyl, tetrahydrobenzothiazolyl, benzoxazolyl, benzoisothiazolyl, benzoisoxazolyl, benzimidazolyl, naphthyridinyl, tetrahydronaphthyridinyl, thienopyridyl, tetrahydrothienopyridyl, thiazolopyridyl, tetrahydrothiazolopyridyl, thiazolopyridazinyl, tetrahydrothiazolopyridazinyl, pyrrolopyridyl, dihydropyrrolopyridyl, tetrahydropyrrolopyridyl, pyrrolopyrimidinyl, dihydropyrrolopyrimidinyl, pyridoquinazolinyl, dihydropyridoquinazolinyl pyridopyrimidinyl, tetrahydropyridopyrimidinyl, pyranothiazolyl, dihydropyranothiazolyl, furopyridyl, tetrahydrofuropyridyl, oxazolopyridyl, tetrahydroxazolopyridyl, oxazolopyridazinyl, tetrahydroxazolopyridazinyl, pyrrolothiazolyl, clihydropyrrolothiazolyl, pyrroloxazolyl, dihydropyrroloxazolyl, thienopyrrolyl, thiazolopyrimidinyl, 4-oxotetrahydrocinnolinyl, 1,2,4-benzothiadiazinyl, 1,1-dioxy-2H-1,2,4-benzothiadiazinyl, 1,2,4-benzoxadiazinyl, cyclopentapyranyl, thienofuranyl, furopyranyl, pyridoxazinyl, pyrazoloxazolyl, imidazothiazolyl, imidazopyridyl, tetrahydroimidazopyridyl, pyrazinopyridazinyl, benzisoquinolyl, furocinnolyl, pyrazolothiazolopyridazinyl, tetrahydropyrazolothiazolopyridazinyl, hexahydrothiazolopyridazinopyridazinyl, imidazotriazinyl, oxazolopyridyl, benzoxepynyl, benzazepinyl, tetrahydrobenzazepinyl, benzodiazepinyl, benzotriazepinyl, thienoazepinyl, tetrahydrothienoazepinyl, thienodiazepinyl, thienotriazepinyl, thiazoloazepinyl, tetrahydrothiazoloazepinyl, tetrahydro-5,6-tetramethylenethiazolopyridazinyl, and 5,6-trimethylene-4,5,6,7-tetrahydrothiazolopyridazinyl. No particular limitation is imposed on the manner of the condensation of the above condensed heterocyclic group.

Each of the aforementioned aryl, heteroaryl, arylalkenyl, heteroarylalkenyl, a saturated or unsaturated bicyclic or tricyclic condensed hydrocarbon group, and a saturated or unsaturated bicyclic or tricyclic condensed heterocyclic group may have 1 to 3 substituents. Examples of the substituents include hydroxyl, halogen atoms such as a fluorine atom, a chlorine atom, a bromine atom, and an iodine atom, C1-C6 halogenoalkyl containing 1 to 3 halogen atoms, amino, cyano, aminoalkyl, nitro, hydroxyalkyl (e.g., hydroxymethyl and 2-hydroxyethyl), alkoxyalkyl (e.g., methoxymethyl and 2-methoxyethyl), carboxyl, carboxyalkyl (e.g., carboxymethyl and 2-carboxyethyl), alkoxycarbonylalkyl (e.g., methoxycarbonylmethyl and ethoxycarbonylmethyl), acyl (e.g., alkanoyls such as formyl, acetyl, and propionyl), amidino, hydroxyamidino(amino(hydroxyimino)methyl), linear, branched, or cyclic C1-C6 alkyl (e.g., methyl and ethyl), linear, branched, or cyclic C1-C6 alkoxy (e.g., methoxy and ethoxy), amidino which is substituted by linear, branched, or cyclic C1-C6 alkyl (e.g., imino(methylamino)methyl), amidino which is substituted by a linear, branched, or cyclic C1-C6 alkoxy group (e.g., amino(methoxyimino)methyl), amidino which is substituted by linear, branched, or cyclic C2-C7 alkoxycarbonyl (e.g., amino(methoxycarbonylimino)methyl and amino(ethoxycarbonylimino)methyl), linear, branched, or cyclic C2-C6 alkenyl (e.g., vinyl and allyl), linear or branched C2-C6 alkynyl (e.g., ethynyl and propynyl), linear, branched, or cyclic C2-C6 alkoxycarbonyl (e.g., methoxycarbonyl and ethoxycarbonyl), carbamoyl, mono or dialkylcarbamoyl which is substituted by linear, branched, or cyclic C1-C6 alkyl group at the nitrogen atom thereof (e.g., methylcarbamoyl, ethylcarbamoyl, dimethylcarbamoyl, and ethylmethylcarbamoyl), mono or dialkylamino which is substituted by linear, branched, or cyclic C1-C6 alkyl (e.g., ethylamino, dimethylamino, and methylethylamino) and 5- or 6-membered nitrogen-containing heterocyclic group (e.g., pyrrolidino, piperidino, piperazino, and morpholino).

Among the above-described groups, group $Q^2$ is preferably any one of the following 12 groups (a) to (l);

[F46]

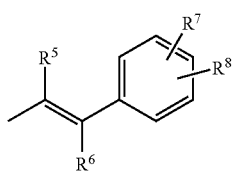

(a)

(wherein each of $R^5$ and $R^6$ represents a hydrogen atom, cyano, a halogen atom, alkyl, hydroxyalkyl, alkoxy, alkoxyalkyl, carboxyl, carboxyalkyl, acyl, alkoxycarbonyl, alkoxycarbonylalkyl, or phenyl which may be substituted by cyano, hydroxyl, a halogen atom, alkyl, or alkoxy, and each of $R^7$ and $R^8$ represents a hydrogen atom, hydroxyl, nitro, amino, cyano, a halogen atom, alkyl, alkenyl, alkynyl, halogenoalkyl, hydroxyalkyl, alkoxy, alkoxyalkyl, carboxyl, carboxyalkyl, acyl, carbamoyl, N-alkylcarbamoyl, N,N-dialkylcarbamoyl, alkoxycarbonyl, amidino, or alkoxycarbonylalkyl);

[F47]

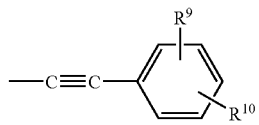

(b)

(wherein each of $R^9$ and $R^{10}$ represents a hydrogen atom, hydroxyl, nitro, amino, cyano, a halogen atom, alkyl, alkenyl, alkynyl, halogenoalkyl, hydroxyalkyl, alkoxy, alkoxyalkyl, carboxyl, carboxyalkyl, acyl, carbamoyl, N-alkylcarbamoyl, N,N-dialkylcarbamoyl, alkoxycarbonyl, amidino, or alkoxycarbonylalkyl);

[F48]

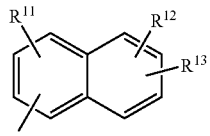

(c)

(wherein each of $R^{11}$, $R^{12}$, and $R^{13}$ represents a hydrogen atom, hydroxyl, nitro, amino, cyano, a halogen atom, alkyl, alkenyl, alkynyl, halogenoalkyl, hydroxyalkyl, alkoxy, alkoxyalkyl, carboxyl, carboxyalkyl, acyl, carbamoyl, N-alkylcarbamoyl, N,N-dialkylcarbamoyl, alkoxycarbonyl, amidino, or alkoxycarbonylalkyl);

[F49]

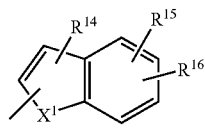

(d)

(wherein $X^1$ represents $CH_2$, CH, NH, NOH, N, O, or S, and each of $R^{14}$, $R^{15}$ and $R^{16}$ represents a hydrogen atom, hydroxyl, nitro, amino, cyano, a halogen atom, alkyl, alkenyl, alkynyl, halogenoalkyl, hydroxyalkyl, alkoxy, alkoxyalkyl, carboxyl, carboxyalkyl, acyl, carbamoyl, N-alkylcarbamoyl, N,N-dialkylcarbamoyl, alkoxycarbonyl, amidino, or alkoxycarbonylalkyl);

[F50]

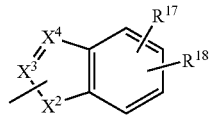

(e)

(wherein $X^2$ represents NH, N, O, or S; $X^3$ represents N, C, or CH; $X^4$ represents N, C, or CH, and each of $R^{17}$ and $R^{18}$ represents a hydrogen atom, hydroxyl, nitro, amino, cyano, a halogen atom, alkyl, alkenyl, alkynyl, halogenoalkyl, hydroxyalkyl, alkoxy, alkoxyalkyl, carboxyl, carboxyalkyl, acyl, carbamoyl, N-alkylcarbamoyl, N,N-dialkylcarbamoyl, alkoxycarbonyl, amidino, or alkoxycarbonylalkyl, excluding the cases where $X^3$ and $X^4$ are combinations of C and CH, and are both C or CH;

[F51]

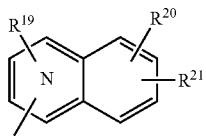

(f)

(wherein N denotes that one or two ring carbon atoms of the ring having $R^{19}$ and being represented with reference "N" are substituted by nitrogen, each of $R^{19}$, $R^{20}$, and $R^{21}$ represents a hydrogen atom, hydroxyl, nitro, amino, cyano, a halogen atom, alkyl, alkenyl, alkynyl, halogenoalkyl, hydroxyalkyl, alkoxy, alkoxyalkyl, carboxyl, carboxyalkyl, acyl, carbamoyl, N-alkylcarbamoyl, N,N-dialkylcarbamoyl, alkoxycarbonyl, amidino, or alkoxycarbonylalkyl);

[F52]

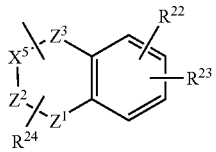

(g)

(wherein $X^5$ represents $CH_2$, CH, N, or NH; $Z^1$ represents N, NH, or O; $Z^2$ represents $CH_2$, CH, C, or N; $Z^3$ represents $CH_2$, CH, S, $SO_2$, or C=O; $X^5$—$Z^2$ represents a moiety in which $X^5$ and $Z^2$ are linked via a single bond or a double bond; each of $R^{22}$ and $R^{23}$ represents a hydrogen atom, hydroxyl, nitro, amino, cyano, a halogen atom, alkyl, alkenyl, alkynyl, halogenoalkyl, hydroxyalkyl, alkoxy, alkoxyalkyl, carboxyl, carboxyalkyl, acyl, carbamoyl, N-alkylcarbamoyl, N,N-dialkylcarbamoyl, alkoxycarbonyl, amidino, or alkoxycarbonylalkyl; $R^{24}$ represents a hydrogen atom or alkyl);

[F53]

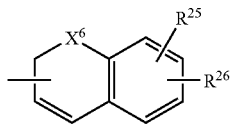

(h)

(wherein $X^6$ represents O or S, and each of $R^{25}$ and $R^{26}$ represents a hydrogen atom, hydroxyl, nitro, amino, cyano, a halogen atom, alkyl, alkenyl, alkynyl, halogenoalkyl, hydroxyalkyl, alkoxy, alkoxyalkyl, carboxyl, carboxyalkyl, acyl, carbamoyl, N-alkylcarbamoyl, N,N-dialkylcarbamoyl, alkoxycarbonyl, amidino, or alkoxycarbonylalkyl);

[F54]

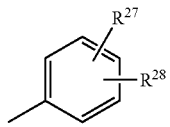

(i)

(wherein each of $R^{27}$ and $R^{28}$ represents a hydrogen atom, hydroxyl, nitro, amino, cyano, halogen atom, alkyl, alkenyl, alkynyl, halogenoalkyl, hydroxyalkyl, alkoxy, alkoxyalkyl, carboxyl, carboxyalkyl, acyl, carbamoyl, N-alkylcarbamoyl, N,N-dialkylcarbamoyl, alkoxycarbonyl, amidino or alkoxycarbonylalkyl);

[F55]

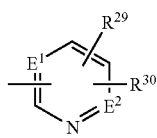

(j)

(wherein each of $E^1$ and $E^2$ represents N or CH, and each of $R^{29}$ and $R^{30}$ represents a hydrogen atom, hydroxyl, nitro, amino, cyano, a halogen atom, alkyl, alkenyl, alkynyl, halogenoalkyl, hydroxyalkyl, alkoxy, alkoxyalkyl, carboxyl, carboxyalkyl, acyl, carbamoyl, N-alkylcarbamoyl, N,N-dialkylcarbamoyl, alkoxycarbonyl, amidino, or alkoxycarbonylalkyl);

[F56]

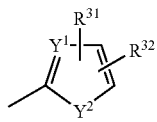

(k)

(wherein $Y^1$ represents CH or N; $Y^2$ represents —N($R^{33}$)— (Wherein $R^{33}$ represents a hydrogen atom or C1-C6 alkyl.), O, or S, each of $R^{31}$ and $R^{32}$ represents a hydrogen atom, hydroxyl, nitro, amino, cyano, a halogen atom, alkyl, alkenyl, alkynyl, halogenoalkyl, hydroxyalkyl, alkoxy, alkoxyalkyl, carboxyl, carboxyalkyl, acyl, carbamoyl, N-alkylcarbamoyl, N,N-dialkylcarbamoyl, alkoxycarbonyl, amidino, or alkoxycarbonylalkyl); and

[F57]

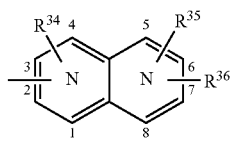

(l)

(wherein numerals 1 to 8 indicate positions; each of N indicate that any one of carbon atoms of positions 1 to 4 and any one of carbon atoms of positions 5 to 8 has been substituted by a nitrogen atom; each of $R^{34}$, $R^{35}$, and $R^{36}$ represents a hydrogen atom, hydroxyl, nitro, amino, cyano, a halogen atom, alkyl, alkenyl, alkynyl, halogenoalkyl, hydroxyalkyl, alkoxy, alkoxyalkyl, carboxyl, carboxyalkyl, acyl, carbamoyl, N-alkylcarbamoyl, N,N-dialkylcarbamoyl, alkoxycarbonyl, amidino, or alkoxycarbonylalkyl).

These groups will next be described in detail.

In the description of $R^5$ to $R^{36}$ in the above groups, the halogen atom is a fluorine atom, a chlorine atom, a bromine atom, or an iodine atom; the alkyl is a linear, branched, or cyclic C1-C6; the alkenyl is a linear, branched, or cyclic C2-C6; the alkynyl is a linear or branched C2-C6; the hydroxyalkyl is a group corresponding to the above C1-C6 alkyl which has been substituted by one hydroxyl group; the alkoxy is a linear, branched, or cyclic C1-C6; the alkoxyalkyl is a group corresponding to the above $C_1$-$C_6$ alkyl which has been substituted by the above one $C_1$-$C_6$ alkoxy group; the carboxyalkyl is a group corresponding to the above $C_1$-$C_6$ alkyl which has been substituted by one carboxyl group; the acyl is a C1-C6 alkanoyl (including formyl), aroyl such as benzoyl or naphthoyl, or arylalkanoyl corresponding to the above $C_1$-$C_6$ alkanoyl which has been substituted by the above $C_6$-$C_{14}$ aryl; the N-alkylcarbamoyl is a group corresponding to a carbamoyl group which has been substituted by the above $C_1$-$C_6$ alkyl group at the nitrogen atom of the carbamoyl group; the N,N-dialkylcarbamoyl is a group corresponding to a carbamoyl group which has been substituted by two of the above $C_1$-$C_6$ alkyl groups at the nitrogen atom of the carbamoyl group; the alkoxycarbonyl is a group composed of the above $C_1$-$C_6$ alkoxy and carbonyl; the alkoxycarbonylalkyl is a group corresponding to the above $C_1$-$C_6$ alkyl which has been substituted by one of the ($C_1$-$C_6$ alkoxy) carbonyl groups mentioned above, the halogenoalkyl is a group corresponding to the above $C_1$-$C_6$ alkyl which has been substituted by 1 to 3 halogen atoms. In the above description, no particular limitation is imposed on the position of the substitution.

In the following group:

[F58]

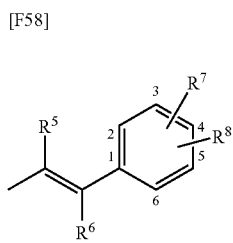

(a)

(wherein $R^5$, $R^6$, $R^7$, and $R^8$ have the same meanings as described above, numerals 1 to 6 represent positions), each of $R^5$ and $R^6$ is preferably a hydrogen atom, cyano, a halogen atom, alkyl, alkenyl, alkynyl, or halogenoalkyl, with a hydrogen atom and alkyl being more preferred. Of alkyl groups, methyl is preferred. Preferably, one of $R^7$ and $R^8$ is a hydrogen atom, and the other group is a hydrogen atom, cyano, a halogen atom, alkyl, alkenyl, alkynyl, or halogenoalkyl. Among the cases in which one of $R^7$ and $R^8$ is a hydrogen atom, the other group is more preferably a hydrogen atom, a halogen atom, alkyl, or alkynyl. In this case, the halogen atom is preferably a fluorine atom, a chlorine atom, or a bromine atom, and the alkyl group is preferably a methyl group. As alkynyl, ethynyl is particularly preferred. Preferred examples of the groups represented by the above formula include chlorostyryl, fluorostyryl, bromostyryl, and ethynylstyryl. No particular limitation is imposed on the position, in any of these groups, to which a halogen atom, alkyl, or alkynyl is linked. Among the positions of the group represented by the above formula, 4-position is particularly preferred. Preferred examples of the groups include 4-chlorostyryl, 4-fluorostyryl, 4-bromostyryl, and 4-ethynylstyryl.

In the following group:

[F59]

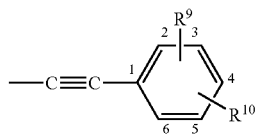

(b)

(wherein $R^9$ and $R^{10}$ have the same meanings as described above, and numerals "1" to "6" represent positions), each of $R^9$ and $R^{10}$ is preferably a hydrogen atom, a halogen atom, alkyl, or alkynyl. The case where $R^9$ is a hydrogen atom and $R^{10}$ is a hydrogen atom, a halogen atom, alkyl, or alkynyl is more preferred. In the above case, the halogen atom is preferably fluorine, chlorine, or bromine, the alkyl group is preferably methyl, and the alkynyl group is particularly preferably ethynyl. Preferred examples of the group represented by the above formula include chlorophenylethynyl, fluorophenylethynyl, bromophenylethynyl, and ethynylphenylethynyl. No limitation is imposed on the position, in any of these groups, to which a halogen atom, alkyl, or alkynyl is linked. Among them, 4-position is particularly preferred. Specifically, 4-chlorophenylethynyl, 4-fluorophenylethynyl, 4-bromophenylethynyl, and 4-ethynylphenylethynyl are preferred, among others.

In the following group:

[F60]

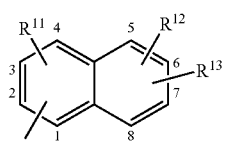

(c)

(wherein $R^{11}$, $R^{12}$, and $R^{13}$ have the same meanings as described above, and numerals "1" to "8" represent positions) each of $R^{11}$, $R^{12}$ and $R^{13}$ is preferably a hydrogen atom, cyano, a halogen atom, alkyl, alkenyl, alkynyl, or halogenoalkyl. $R^{11}$ is preferably a hydrogen atom, alkyl, a halogen atom, or hydroxyl, with a hydrogen atom being more preferred. Preferably, one of $R^{12}$ and $R^{13}$ is a hydrogen atom, and the other group is a hydrogen atom, cyano, a halogen atom, alkyl, alkenyl, alkynyl, or halogenoalkyl. Among the cases in which one of $R^{12}$ and $R^{13}$ is a hydrogen atom, the other group is more preferably a hydrogen atom, a halogen atom, alkyl, or alkynyl. In this case, the halogen atom is preferably a fluorine atom, a chlorine atom, or a bromine atom, and the alkyl group is preferably a methyl group. As alkynyl, ethynyl is preferred. In the naphthyl group, a 2-naphthyl group is preferred to a 1-naphthyl group. In the case of the 2-naphthyl group, the position substituted by a halogen atom, alkyl group or alkynyl group is preferably a 6- or 7-position in the above formula though it should not be particularly limited, with a 6-position being most preferred. These naphthyl groups are preferably substituted by a chlorine, fluorine, or bromine atom, an alkynyl group, or the like. Particularly preferably, these naphthyl groups are substituted with a chlorine, fluorine, or bromine atom, an alkynyl group, or the like. Specific examples include 6-chloro-2-naphthyl, 6-fluoro-2-naphthyl, 6-bromo-2-naphthyl, 6-ethynyl-2-naphthyl, 7-chloro-2-naphthyl, 7-fluoro-2-naphthyl, 7-bromo-2-naphthyl, and 7-ethynyl-2-naphthyl.

In the following group:

[F61]

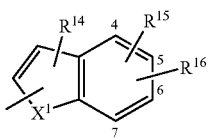

(d)

(wherein $X^1$, $R^{14}$, $R^{15}$, and $R^{16}$ have the same meanings as described above, and numerals "4" to "7" represent positions), $X^1$ is preferably NH, NOH, N, O, or S, with NH, O, and S being more preferred. $R^{14}$ is preferably a hydrogen atom, a halogen atom, acyl, N-alkylcarbamoyl, N,N-dialkylcarbamoyl, or alkyl. Each of $R^{15}$ and $R^{16}$ is preferably a hydrogen atom, cyano, a halogen atom, alkyl, alkenyl, alkynyl, or halogenoalkyl. Preferably, one of $R^{15}$ and $R^{16}$ is a hydrogen atom or a halogen atom, with a fluorine atom or a chlorine atom being more preferred, and the other group is a hydrogen atom, cyano, a halogen atom, alkyl, alkenyl, alkynyl, or halogenoalkyl. Among them, the other group is particularly preferably a hydrogen atom, a halogen atom, alkyl, or alkynyl. In this case, the halogen atom is preferably a fluorine atom, a chlorine atom, or a bromine atom, the alkyl group is preferably methyl, and the alkynyl group is preferably ethynyl. No particular limitation is imposed on the position to which a halogen atom, alkyl, or alkynyl is linked. Among them, 4-, 5-, and 6-positions are preferred.

Preferred examples of the group represented by the above formula include 5-chloroindolyl, 5-fluoroindolyl, 5-bromoindolyl, 5-ethynylindolyl, 5-methylindolyl, 5-chloro-4-fluoroindolyl, 5-chloro-3-fluoroindolyl, 5-fluoro-3-chloroindolyl, 5-ethynyl-3-fluoroindolyl, 5-chloro-3-(N,N-dimethylcarbamoyl)indolyl, 5-fluoro-3-(N,N-dimethylcarbamoyl)indolyl, 5-chloro-3-formylimidolyl, 5-fluoro-3-formylindolyl, 6-chloroindolyl, 6-fluoroindolyl, 6-bromoindolyl, 6-ethynylindolyl, 6-methylindolyl, 5-chlorobenzothienyl, 5-fluorobenzothienyl, 5-bromobenzothienyl, 5-ethynylbenzothienyl, 5-methylbenzothienyl, 5-chloro-4-fluorobenzothienyl, 6-chlorobenzothienyl, 6-fluorobenzothienyl, 6-bromobenzothienyl, 6-ethynylbenzothienyl, 6-methylbenzothienyl, 5-chlorobenzofuryl, 5-fluorobenzofuryl, 5-bromobenzofuryl, 5-ethynylbenzofuryl, 5-methylbenzofuryl, 5-chloro-4-fluorobenzofuryl, 6-chlorobenzofuryl, 6-fluorobenzofuryl, 6-bromobenzofuryl, 6-ethynylbenzofuryl, and 6-methylbenzofuryl.

No particular limitation is imposed on the position, in any of these substituents, to which $T^1$ is linked. In the above formula (d), 2-position and 3-position are preferred. Preferably, the group is, among others, 5-chloroindol-2-yl, 5-fluoroindol-2-yl, 5-bromoindol-2-yl, 5-ethynylindol-2-yl, 5-methylindol-2-yl, 5-chloro-4-fluoroindol-2-yl, 5-chloro-3-fluoroindol-2-yl, 3-bromo-5-chloroindol-2-yl, 3-chloro-5-fluoroindol-2-yl, 3-bromo-5-fluoroindol-2-yl, 5-bromo-3-chloroindol-2-yl, 5-bromo-3-fluoroindol-2-yl, 5-chloro-3-form 5-fluoro-3-formylindol-2-yl, 5-bromo-3-formylindol-2-yl, 5-ethynyl-3-formylindol-2-yl, 5-chloro-3-(N,N-dimethylcarbamoyl)indol-2-yl, 5-fluoro-3-(N,N-dimethylcarbamoyl)indol-2-yl, 5-bromo-3-(N,N-dimethylcarbamoyl)indol-2-yl, 5-ethynyl-3-(N,N-dimethylcarbamoyl)indol-2-yl, 6-chloroindol-2-yl, 6-fluoroindol-2-yl, 6-bromoindol-2-yl, 6-ethynylindol-2-yl, 6-methylindol-2-yl, 5-chloroindol-3-yl, 5-fluoroindol-3-yl, 5-bromoindol-3-yl, 5-ethynylindol-3-yl, 5-methylindol-3-yl, 5-chloro-4-fluoroindol-3-yl, 6-chloroindol-3-yl, 6-fluoroindol-3-yl, 6-bromoindol-3-yl, 6-ethynylindol-3-yl, 6-methylindol-3-yl, 5-chlorobenzothiophen-2-yl, 5-fluorobenzothiophen-2-yl, 5-bromobenzothiophen-2-yl, 5-ethynylbenzothiophen-2-yl, 5-methylbenzothiophen-2-yl, 5-chloro-4-fluorobenzothiophen-2-yl, 6-chlorobenzothiophen-2-yl, 6-fluorobenzothiophen-2-yl, 6-bromobenzothiophen-2-yl, 6-ethynylbenzothiophen-2-yl, 6-methylbenzothiophen-2-yl, 5-chlorobenzothiophen-3-yl, 5-fluorobenzothiophen-3-yl, 5-bromobenzothiophen-3-yl, 5-ethynylbenzothiophen-3-yl, 5-methylbenzothiophen-3-yl, 5-chloro-4-fluorobenzothiophen-3-yl, 6-chlorobenzothiophen-3-yl, 6-fluorobenzothiophen-3-yl, 6-bromobenzothiophen-3-yl, 6-ethynylbenzothiophen-3-yl, 6-methylbenzothiophen-3-yl, 5-chlorobenzofuran-2-yl, 5-fluorobenzofuran-2-yl, 5-bromobenzofuran-2-yl, 5-ethynylbenzofuran-2-yl, 5-methylbenzofuran-2-yl, 5-chloro-4-fluorobenzofuran-2-yl, 6-chlorobenzofuran-2-yl, 6-fluorobenzofuran-2-yl, 6-bromobenzofuran-2-yl, 6-ethynylbenzofuran-2-yl, 6-methylbenzofuran-2-yl, 5-chlorobenzofuran-3-yl, 5-fluorobenzofuran-3-yl, 5-bromobenzofuran-3-yl, 5-ethynylbenzofuran-3-yl, 5-methylbenzofuran-3-yl, 5-chloro-4-fluorobenzofuran-3-yl, 6-chlorobenzofuran-3-yl, 6-fluorobenzofuran-3-yl, 6-bromobenzofuran-3-yl, 6-ethynylbenzofuran-3-yl, or 6-methylbenzofuran-3-yl.

More preferably, the group is, among others, 5-chloroindol-2-yl, 5-fluoroindol-2-yl, 5-bromoindol-2-yl, 5-ethynylindol-2-yl, 5-methylindol-2-yl, 5-chloro-4-fluoroindol-2-yl, 6-chloroindol-2-yl, 6-fluoroindol-2-yl, 6-bromoindol-2-yl, 6-ethynylindol-2-yl, 6-methylindol-2-yl, 5-chloro-3-fluoroindol-2-yl, 3-bromo-5-chloroindol-2-yl, 3-chloro-5-fluoroindol-2-yl, 3-bromo-5-fluoroindol-2-yl, 5-bromo-3-chloroindol-2-yl, 5-bromo-3-fluoroindol-2-yl, 5-chloro-3-formylindol-2-yl, 5-fluoro-3-formylindol-2-yl, 5-bromo-3-formylindol-2-yl, 5-ethynyl-3-formylindol-2-yl, 5-chloro-3-(N,N-dimethylcarbamoyl)indol-2-yl, 5-fluoro-3-(N,N-dimethylcarbamoyl)indol-2-yl, 5-bromo-3-(N,N-dimethylcarbamoyl)indol-2-yl, 5-ethynyl-3-(N,N-dimethylcarbamoyl)indol-2-yl, 5-chlorobenzothiophen-2-yl, 5-fluorobenzothiophen-2-yl, 5-bromobenzothiophen-2-yl, 5-ethynylbenzothiophen-2-yl, 5-methylbenzothiophen-2-yl, 5-chloro-4-fluorobenzothiophen-2-yl, 6-chlorobenzothiophen-2-yl, 6-fluorobenzothiophen-2-yl, 6-bromobenzothiophen-2-yl, 6-ethynylbenzothiophen-2-yl, 6-methylbenzothiophen-2-yl, 5-chlorobenzofuran-2-yl, 5-fluorobenzofuran-2-yl, 5-bromobenzofuran-2-yl, 5-ethynylbenzofuran-2-yl, 5-methylbenzofuran-2-yl, 5-chloro-4-fluorobenzofuran-2-yl, 6-chlorobenzofuran-2-yl, 6-fluorobenzofuran-2-yl, 6-bromobenzofuran-2-yl, 6-ethynylbenzofuran-2-yl, or 6-methylbenzofuran-2-yl.

In the following group:

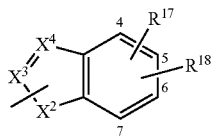

(e)

(wherein $X^2$, $X^3$, $X^4$, $R^{17}$, and $R^{18}$ have the same meanings as described above, and numerals "4" to "7" represent positions), $X^2$ is preferably NH, O, or S. The case where any one of $X^3$ and $X^4$ is CH or C is preferred, and the case where one of $X^3$ and $X^4$ is C is particularly preferred. Preferably, $R^{17}$ and $R^{18}$ each independently represent a hydrogen atom, cyano, a halogen atom, alkyl, alkenyl, alkynyl, or halogenoalkyl. Preferably, one of $R^{17}$ and $R^{18}$ is a hydrogen atom, and the other group is a hydrogen atom, cyano, a halogen atom, alkyl, alkenyl, alkynyl, or halogenoalkyl. Among the cases in which one of $R^{17}$ and $R^{18}$ is a hydrogen atom, the other group is more preferably a hydrogen atom, a halogen atom, alkyl, or alkynyl. In this case, the halogen atom is preferably a fluorine atom, a chlorine atom, or a bromine atom, the alkyl group is preferably a methyl group, and the alkynyl group is preferably ethynyl.

No particular limitation is imposed on the position to which a halogen atom, alkyl, or alkynyl is linked. Among them, 5-position or 6-position is preferred. Specific examples of preferred groups represented by the above formula include 5-chloroindazolyl, 5-fluoroindazolyl, 5-bromoindazolyl, 5-ethynylindazolyl, 6-chloroindazolyl, 6-fluoroindazolyl, 6-bromoindazolyl, 6-ethynylindazolyl, 5-chlorobenzimidazolyl, 5-fluorobenzimidazolyl, 5-bromobenzimidazolyl, 5-ethynylbenzimidazolyl, 6-chlorobenzimidazolyl, 6-fluorobenzimidazolyl, 6-bromobenzimidazolyl, 6-ethynylbenzimidazolyl, 5-chlorobenzothiazolyl, 5-fluorobenzothiazolyl, 5-bromobenzothiazolyl, 5-ethynylbenzothiazolyl, 6-chlorobenzothiazolyl, 6-fluorobenzothiazolyl, 6-bromobenzothiazolyl, 6-ethynylbenzothiazolyl, 5-chlorobenzoxazolyl, 5-fluorobenzoxazolyl, 5-bromobenzoxazolyl, 5-ethynylbenzoxazolyl, 6-chlorobenzoxazolyl, 6-fluorobenzoxazolyl, 6-bromobenzoxazolyl, 6-ethynylbenzoxazolyl, 5-chlorobenzoisothiazolyl, 5-fluorobenzoisothiazolyl, 5-bromobenzoisothiazolyl, 5-ethynylbenzoisothiazolyl, 6-chlorobenzoisothiazolyl, 6-fluorobenzoisothiazolyl, 6-bromobenzoisothiazolyl, 6-ethynylbenzoisothiazolyl, 5-chlorobenzoisoxazolyl, 5-fluorobenzoisoxazolyl, 5-bromobenzoisoxazolyl, 5-ethynylbenzoisoxazolyl, 6-chlorobenzoisoxazolyl, 6-fluorobenzoisoxazolyl, 6-bromobenzoisoxazolyl, and 6-ethynylbenzoisoxazolyl.

No particular limitation is imposed on the position, in any of these substituents, to which $T^1$ is hiked. However, the group is preferably 5-chloroindazol-3-yl, 5-fluoroindazol-3-yl, 5-bromoindazol-3-yl, 5-ethynylindazol-3-yl, 6-chloroindazol-3-yl, 6-fluoroindazol-3-yl, 6-bromoindazol-3-yl, 6-ethynylindazol-3-yl, 5-chlorobenzimidazol-2-yl, 5-fluorobenzimidazol-2-yl, 5-bromobenzimidazol-2-yl, 5-ethynylbenzimidazol-2-yl, 6-chlorobenzimidazol-2-yl, 6-fluorobenzimidazol-2-yl, 6-bromobenzimidazol-2-yl, 6-ethynylbenzimidazol-2-yl, 5-chlorobenzothiazol-2-yl, 5-fluorobenzothiazol-2-yl, 5-bromobenzothiazol-2-yl, 5-ethynylbenzothiazol-2-yl, 6-chlorobenzothiazol-2-yl, 6-fluorobenzothiazol-2-yl, 6-bromobenzothiazol-2-yl, 6-ethynylbenzothiazol-2-yl, 5-chlorobenzoxazol-2-yl, 5-fluorobenzoxazol-2-yl, 5-bromobenzoxazol-2-yl, 5-ethynylbenzoxazol-2-yl, 6-chlorobenzoxazol-2-yl, 6-fluorobenzoxazol-2-yl, 6-bromobenzoxazol-2-yl, 6-ethynylbenzoxazol-2-yl, 5-chlorobenzoisothiazol-3-yl, 5-fluorobenzoisothiazol-3-yl, 5-bromobenzoisothiazol-3-yl, 5-ethynylbenzoisothiazol-3-yl, 6-chlorobenzoisothiazol-3-yl, 6-fluorobenzoisothiazol-3-yl, 6-bromobenzoisothiazol-3-yl, 6-ethynylbenzoisothiazol-3-yl, 5-chlorobenzoisoxazol-3-yl, 5-fluorobenzoisoxazol-3-yl, 5-bromobenzoisoxazol-3-yl, 5-ethynylbenzoisoxazol-3-yl, 6-chlorobenzoisoxazol-3-yl, 6-fluorobenzoisoxazol-3-yl, 6-bromobenzoisoxazol-3-yl, or 6-ethynylbenzoisoxazol-3-yl.

The group is more preferably 5-chlorobenzimidazol-2-yl, 5-fluorobenzimidazol-2-yl, 5-bromobonzimidazol-2-yl, 5-ethynylbenzimidazol-2-yl, 6-chlorobenzimidazol-2-yl, 6-fluorobenzimidazol-2-yl, 6-bromobenzimidazol-2-yl, 6-ethynylbenzimidazol-2-yl, 5-chlorobenzothiazol-2-yl, 5-fluorobenzothiazol-2-yl, 5-bromobenzothiazol-2-yl, 5-ethynylbenzothiazol-2-yl, 6-chlorobenzothiazol-2-yl, 6-fluorobenzothiazol-2-yl, 6-bromobenzothiazol-2-yl, 6-ethynylbenzothiazol-2-yl, 5-chlorobenzoxazol-2-yl, 5-fluorobenzoxazol-2-yl, 5-bromobenzoxazol-2-yl, 5-ethynylbenzoxazol-2-yl, 6-chlorobenzoxazol-2-yl, 6-fluorobenzoxazol-2-yl, 6-bromobenzoxazol-2-yl, and 6-ethynylbenzoxazol-2-yl, still more preferably 5-chlorobenzimidazol-2-yl, 5-fluorobenzimidazol-2-yl, 5-bromobenzimidazol-2-yl, or 5-ethynylbenzimidazol-2-yl.

In the following group:

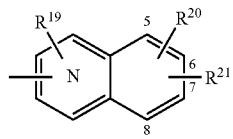

(f)

(wherein N denotes that one or two ring carbon atoms of the ring having $R^{19}$ and being represented with reference "N" are substituted by nitrogen, $R^{19}$, $R^{20}$, and $R^{21}$ have the same meanings as described above, and numerals "5" to "8" represent positions) each of $R^{19}$, $R^{20}$, and $R^{21}$ represents a hydrogen atom, cyano, a halogen atom, alkyl, alkenyl, alkynyl, or halogenoalkyl. $R^{19}$ is particularly preferably a hydrogen atom. Preferably, one of $R^{20}$ and $R^{21}$ is a hydrogen atom, and the other group is a hydrogen atom, cyano, a halogen atom, alkyl, alkenyl, alkynyl, or halogenoalkyl. Among the cases in which one of $R^{20}$ and $R^{21}$ is a hydrogen atom, the other group is more preferably a hydrogen atom, a halogen atom, alkyl, or alkynyl. In this case, the halogen atom is preferably a fluorine atom, a chlorine atom, or a bromine atom, the alkyl group is preferably a methyl group, and the alkynyl group is preferably an ethynyl group. No particular limitation is imposed on the position to which a halogen atom, alkyl, or alkynyl is linked. Among them, 6-position or 7-position is preferred.

Specific examples of the group represented by the above formula include quinolinyl, isoquinolinyl, and cinnolinyl. Among them, the group is preferably, among others, 6-chloroquinolinyl, 6-fluoroquinolinyl, 6-bromoquinolinyl, 6-ethynylquinolinyl, 6-chloroisoquinolinyl, 6-fluoroisoquinolinyl, 6-bromoisoquinolinyl, 6-ethynylisoquinolinyl, 7-chlorocinnolinyl, 7-fluorocinnolinyl, 7-bromocinnolinyl, or 7-ethynylcinnolinyl, more preferably, among others, 6-chloroquinolin- 2-yl, 6-fluoroquinolin-2-yl, 6-bromoquinolin-2-yl, 6-ethynylquinolin-2-yl, 6-chloroquinolin-3-yl, 6-fluoroquinolin-3-yl, 6-bromoquinolin-3-yl, 6-ethynylquinolin-3-yl, 7-chloroquinolin-2-yl, 7-fluoroquinolin-2-yl, 7-bromoquinolin-2-yl, 7-ethynylquinolin-2-yl, 7-chloroquinolin-3-yl, 7-fluoroquinolin-3-yl, 7-bromoquinolin-3-yl, 7-ethynylquinolin-3-yl, 6-chloroisoquinolin-3-yl, 6-fluoroisoquinolin-3-yl, 6-bromoisoquinolin-3-yl, 6-ethynylisoquinolin-3-yl, 7-chloroisoquinolin-3-yl, 7-fluoroisoquinolin-3-yl, 7-bromoisoquinolin-3-yl, 7-ethynylisoquinolin-3-yl, 7-chlorocinnolin-3-yl, 7-fluorocinnolin-3-yl, 7-bromocinnolin-3-yl, or 7-ethynylcinnolin-3-yl.

Among them, the group is still more preferably 6-chloroquinolin-2-yl, 6-fluoroquinolin-2-yl, 6-bromoquinolin-2-yl, 6-ethynylquinolin-2-yl, 7-chloroquinolin-3-yl, 7-fluoroquinolin-3-yl, 7-bromoquinolin-3-yl, 7-ethynylquinolin-3-yl, 7-chloroisoquinolin-3-yl, 7-fluoro isoquinolin-3-yl, 7-bromoisoquinolin-3-yl, 7-ethynylisoquinolin-3-yl, 7-chlorocinnolin-3-yl, 7-fluorocinnolin-3-yl, 7-bromocinnolin-3-yl, or 7-ethynylcinnolin-3-yl.

In the following group:

[F64]

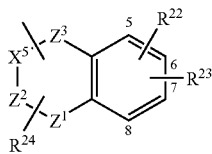

(g)

(wherein numerals "5" to "8" represent positions; $X^5$ represents $CH_2$, CH, N, or NH; $Z^1$ represents N, NH, or O; $Z^2$ represents $CH_2$, CH, C, or N; $Z^3$ represents $CH_2$, CH, S, $SO_2$, or C=O; $X^5$—$Z^2$ represents a moiety in which $X^5$ and $Z^2$ are linked via a single bond or a double bond; $R^{22}$, $R^{23}$, and $R^{24}$ have the same meanings as described above) each of $R^{22}$ and $R^{23}$ is preferably a hydrogen atom, cyano, a halogen atom, alkyl, alkenyl, alkynyl, or halogenoalkyl. Preferably, one of $R^{22}$ and $R^{23}$ is a hydrogen atom, and the other group is a hydrogen atom, cyano, a halogen atom, alkyl, alkenyl, alkynyl, or halogenoalkyl. Among the cases in which one of $R^{22}$ and $R^{23}$ is a hydrogen atom, the other group is more preferably a hydrogen atom, a halogen atom, alkyl, or alkynyl. In this case, the halogen atom is preferably a fluorine atom, a chlorine atom, and a bromine atom, the alkyl group is preferably a methyl group, and the alkynyl group is preferably an ethynyl group. No particular limitation is imposed on the position to which a halogen atom, alkyl, or alkynyl is linked. Among them, 6-position or 7-position is preferred. $R^{24}$ is preferably a hydrogen atom or alkyl. Among alkyl groups, methyl is preferred. $R^{24}$ is particularly preferably a hydrogen atom.

Specific examples of groups represented by the above formula include 4-oxodihydroquinolinyl, tetrahydroquinolinyl, 4-oxodihydroquinazolin-2-yl, 4-oxotetrahydrocinnolinyl, 4-oxobenzopyranyl, 4-oxobenzothiadiazinyl, 1,1-dioxy-4-oxobenzothiadiazinyl, and benzoxadiazinyl.

More specific examples of the group include 6-chloro-4-oxodihydroquinolinyl, 6-fluoro-4-oxodihydroquinolinyl, 6-bromo-4-oxodihydroquinolinyl, 6-ethynyl-4-oxodihydroquinolinyl, 7-chloro-4-oxodihydroquinolinyl, 7-fluoro-4-oxodihydroquinolinyl, 7-bromo-4-oxodihydroquinolinyl, 7-ethynyl-4-oxodihydroquinolinyl, 6-chloro-4-oxo-1,4-dihydroquinazolinyl, 6-fluoro-4-oxo-1,4-dihydroquinazolinyl, 6-bromo-4-oxo-1,4-dihydroquinazolinyl, 6-ethynyl-4-oxo-1,4-dihydroquinazolinyl, 7-chloro-4-oxo-1,4-dihydroquinazolinyl, 7-fluoro-4-oxo-1,4-dihydroquinazolinyl, 7-bromo-4-oxo-1,4-dihydroquinazolinyl, 7-ethynyl-4-oxo-1,4-dihydroquinazolinyl, 6-chloro-1,2,3,4-tetrahydroquinolinyl, 6-fluoro-1,2,3,4-tetrahydroquinolinyl, 6-bromo-1,2,3,4-tetrahydroquinolinyl, 6-ethynyl-1,2,3,4-tetrahydroquinolinyl, 7-chloro-1,2,3,4-tetrahydroquinolinyl, 7-fluoro-1,2,3,4-tetrahydroquinolinyl, 7-bromo-1,2,3,4-tetrahydroquinolinyl, 7-ethynyl-1,2,3,4-tetrahydroquinolinyl, 6-chloro-1,2,3,4-tetrahydro-4-oxocinnolinyl, 6-fluoro-1,2,3,4-tetrahydro-4-oxocinnolinyl, 6-bromo-1,2,3,4-tetrahydro-4-oxocinnolinyl, 6-ethynyl-1,2,3,4-tetrahydro-4-oxocinnolinyl, 7-chloro-1,2,3,4-tetrahydro-4-oxocinnolinyl, 7-fluoro-1,2,3,4-tetrahydro-4-oxocinnolinyl, 7-bromo-1,2,3,4-tetrahydro-4-oxocinnolinyl, 7-ethynyl-1,2,3,4-tetrahydro-4-oxocinnolinyl, 6-chloro-4H-4-oxobenzopyranyl, 6-fluoro-4H-4-oxobenzopyranyl, 6-bromo-4H-4-oxobenzopyranyl, 6-ethynyl-4H-4-oxobenzopyranyl, 7-chloro-4H-4-oxobenzopyranyl, 7-fluoro-4H-4-oxobenzopyranyl, 7-bromo-4H-4-oxobenzopyranyl, 7-ethynyl-4H-4-oxobenzopyranyl, 6-chloro-1,1-dioxy-2H-1,2,4-benzothiadiazinyl, 6-fluoro-1,1-dioxy-2H-1,2,4-benzothiadiazinyl, 6-bromo-1,1-dioxy-2H-1,2,4-benzothiadiazinyl, 6-ethynyl-1,1-dioxy-2H-1,2,4-benzothiadiazinyl, 7-chloro-1,1-dioxy-2H-1,2,4-benzothiadiazinyl, 7-fluoro-1,1-dioxy-2H-1,2,4-benzothiadiazinyl, 7-bromo-1,1-dioxy-2H-1,2,4-benzothiadiazinyl, 7-ethynyl-1,1-dioxy-2H-1,2,4-benzothiadiazinyl, 6-chloro-2H-1,2,4-benzoxadiazinyl, 6-fluoro-2H-1,2,4-benzoxadiazinyl, 6-bromo-2H-1,2,4-benzoxadiazinyl, 6-ethynyl-2H-1,2,4-benzoxadiazinyl, 7-chloro-2H-1,2,4-benzoxadiazinyl, 7-fluoro-2H-1,2,4-benzoxadiazinyl, 7-bromo-2H-1,2,4-benzoxadiazinyl, and 7-ethynyl-2H-1,2,4-benzoxadiazinyl.

Particularly preferred are, for example, 6-chloro-4-oxo-1,4-dihydroquinolin-2-yl, 6-fluoro-4-oxo-1,4-dihydroquinolin-2-yl, 6-bromo-4-oxo-1,4-dihydroquinolin-2-yl, 6-ethynyl-4-oxo-1,4-dihydroquinolin-2-yl, 7-chloro-4-oxo-1,4-dihydroquinolin-2-yl, 7-fluoro-4-oxo-1,4-dihydroquinolin-2-yl, 7-bromo-4-oxo-1,4-dihydroquinolin-2-yl, 7-ethynyl-4-oxo-1,4-dihydroquinolin-2-yl, 6-chloro-4-oxo-1,4-dihydroquinazolin-2-yl, 6-fluoro-4-oxo-1,4-dihydroquinazolin-2-yl, 6-bromo-4-oxo-1,4-dihydroquinazolin-2-yl, 6-ethynyl-4-oxo-1,4-dihydroquinazolin-2-yl, 7-chloro-4-oxo-1,4-dihydroquinazolin-2-yl, 7-fluoro-4-oxo-1,4-dihydroquinazolin-2-yl, 7-bromo-4-oxo-1,4-dihydroquinazolin-2-yl, 7-ethynyl-4-oxo-1,4-dihydroquinazolin-2-yl, 6-chloro-1,2,3,4-tetrahydroquinolin-2-yl, 6-fluoro-1,2,3,4-tetrahydroquinolin-2-yl, 6-bromo-1,2,3,4-tetrahydroquinolin-2-yl, 6-ethynyl-1,2,3,4-tetrahydroquinolin-2-yl, 6-chloro-1,2,3,4-tetrahydro-4-oxocinnolin-2-yl, 6-fluoro-1,2,3,4-tetrahydro-4-oxocinnolin-2-yl, 6-bromo-1,2,3,4-tetrahydro-4-oxocinnolin-2-yl, 6-ethynyl-1,2,3,4-tetrahydro-4-oxocinnolin-2-yl, 7-chloro-1,2,3,4-tetrahydro-4-oxocinnolin-2-yl, 7-fluoro-1,2,3,4-tetrahydro-4-oxocinnolin-2-yl, 7-bromo-1,2,3,4-tetrahydro-4-oxocinnolin-2-yl, 7-ethynyl-1,2,3,4-tetrahydro-4-oxocinnolin-2-yl, 6-chloro-4H-4-oxobenzopyran-2-yl, 6-fluoro-4H-4-oxobenzopyran-2-yl, 6-bromo-4H-4-oxobenzopyran-2-yl, 6-ethynyl-4H-4-oxobenzopyran-2-yl, 7-chloro-4H-4-oxobenzopyran-2-yl, 7-fluoro-4H-4-oxobenzopyran-2-yl, 7-bromo-4H-4-oxobenzopyran-2-yl, 7-ethynyl-4H-4-oxobenzopyran-2-yl, 6-chloro-1,1-dioxy-2H-1,2,4-benzothiadiazin-3-yl, 6-fluoro-1,1-dioxy-2H-1,2,4-benzothiadiazin-3-yl, 6-bromo-1,1-dioxy-2H-1,2,4-benzothiadiazin-3-yl, 6-ethynyl-1,1-dioxy-2H-1,2,4-benzothiadiazin-3-yl, 7-chloro-1,1-dioxy-2H-1,2,4-benzothiadiazin-3-yl, 7-fluoro-1,1-dioxy-2H-1,2,4-benzothiadiazin-3-yl, 7-bromo-1,1-dioxy-2H-1,2,4-benzothiadiazin-3-yl, 7-ethynyl-1,1-dioxy-2H-1,2,4-benzothiadiazin-3-yl, 6-chloro-2H-1,2,4-benzoxadiazin-3-yl, 6-fluoro-2H-1,2,4-benzoxadiazin-3-yl, 6-bromo-2H-1,2,4-benzoxadiazin-3-yl, 6-ethynyl-2H-1,2,4-benzoxadiazin-3-yl, 7-chloro-2H-1,2,4-benzoxadiazin-3-yl, 7-fluoro-2H-1,2,4-benzoxadiazin-3-yl, 7-bromo-2H-1,2,4-benzoxadiazin-3-yl, and 7-ethynyl-2H-1,2,4-benzoxadiazin-3-yl.

Among them, still more preferred are 6-chloro-4-oxo-1,4-dihydroquinolin-2-yl, 6-fluoro-4-oxo-1,4-dihydroquinolin-2-yl, 6-bromo-4-oxo-1,4-dihydroquinolin-2-yl, 6-ethynyl-4-oxo-1,4-dihydroquinolin-2-yl, 6-chloro-4-oxo-1,4-dihydroquinazolin-2-yl, 6-fluoro-4-oxo-1,4-dihydroquinazolin-2-yl, 6-bromo-4-oxo-1,4-dihydroquinazolin-2-yl, and 6-ethynyl-4-oxo-1,4-dihydroquinazolin-2-yl.

In the following group:

[F65]

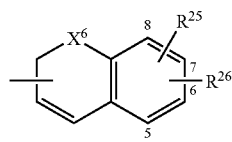

(h)

(wherein $X^6$ represents O or S; $R^{25}$ and $R^{26}$ have the same meanings as described above; and numerals "5" to "8" represent positions), $X^6$ is preferably O, and each of $R^{25}$ and $R^{26}$ is preferably a hydrogen atom, cyano, a halogen atom, alkyl, alkenyl, alkynyl, or halogenoalkyl. Preferably, one of $R^{25}$ and $R^{26}$ is a hydrogen atom, and the other group is a hydrogen atom, cyano, a halogen atom, alkyl, alkenyl, alkynyl, or halogenoalkyl. Among the cases in which one of $R^{25}$ and $R^{26}$ is a hydrogen atom, the other group is particularly preferably a hydrogen atom, a halogen atom, alkyl, or alkynyl. In this case, the halogen atom is preferably a fluorine atom, a chlorine atom, or a bromine atom, the alkyl group is preferably a methyl group, and the alkynyl group is an ethynyl group. No particularly limitation is imposed on the position to which a halogen atom, alkyl, or alkynyl is linked. Among them, 6-position or 7-position is preferred.

Specific examples of preferred groups include 6-chloro-2H-chromen-3-yl, 6-fluoro-2H-chromen-3-yl, 6-bromo-2H-chromen-3-yl, 6-ethynyl-2H-chromen-3-yl, 7-chloro-2H-chromen-3-yl, 7-fluoro-2H-chromen-3-yl, 7-bromo-2H-chromen-3-yl, and 7-ethynyl-2H-chromen-3-yl. 7-chloro-2H-chromen-3-yl, 7-fluoro-2H-chromen-3-yl, 7-bromo-2H-chromen-3-yl, and 7-ethynyl-2H-chromen-3-yl are particularly preferred.

In the following group:

[F66]

(i)

(wherein $R^{27}$ and $R^{28}$ have the same meanings as described above, and numerals "1" to "6" represent positions), preferably, one of $R^{27}$ and $R^{28}$ is a hydrogen atom or a halogen atom, and the other group is a hydrogen atom, cyano, nitro, amino, a halogen atom, alkyl, alkenyl, alkynyl, halogenoalkyl, or N,N-dialkylcarbamoyl. Among the cases in which one of $R^{27}$ and $R^{28}$ is a hydrogen atom or a halogen atom, the other group is particularly preferably a hydrogen atom, a halogen atom, alkyl, or alkynyl. In this case, the halogen atom is preferably a fluorine atom, a chlorine atom, or a bromine atom, the alkyl group is preferably a methyl group, and the alkynyl group is particularly preferably an ethynyl group. Preferred examples of the group represented by the above formula include phenyl, chlorophenyl, fluorophenyl, bromophenyl, ethynylphenyl, and chlorofluorophenyl. No particular limitation is imposed on the position, in any of these groups, to which halogen atom(s), alkyl, or alkynyl is linked. However, when these groups are mono-substituted, 3-position and 4-position of the ring in the above formula are particularly preferred, whereas when these groups are di-substituted, combinations of 4- and 2-positions and 4- and 3-positions of the ring in the above formula are particularly preferred.

Preferred examples of the group include phenyl, 4-chlorophenyl, 4-fluorophenyl, 4-bromophenyl, 4-ethynylphenyl, 3-chlorophenyl, 3-fluorophenyl, 3-bromophenyl, 3-ethynylphenyl, 3-chloro-4-fluorophenyl, 4-chloro-3-fluorophenyl, 4-chloro-2-fluorophenyl, 2-chloro-4-fluorophenyl, 4-bromo-2-fluorophenyl, 2-bromo-4-fluorophenyl, 2,4-dichlorophenyl, 2,4-difluorophenyl, 2,4-dibromophenyl, 4-chloro-3-methylphenyl, 4-fluoro-3-methylphenyl, 4-bromo-3-methylphenyl, 4-chloro-2-methylphenyl, 4-fluoro-2-methylphenyl, 4-bromo-2-methylphenyl, 3,4-dichlorophenyl, 3,4-difluorophenyl, and 3,4-dibromophenyl.

In the following formula:

[F67]

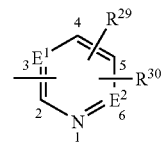

(j)

(wherein $E^1$, $E^2$, $R^{29}$, and $R^{30}$ have the same meanings as described above, and numerals "1" to "6" represent positions), preferably, one of $R^{29}$ and $R^{30}$ is a hydrogen atom or a halogen atom, and the other of the group is a hydrogen atom, cyano, a halogen atom, alkyl, alkenyl, alkynyl, or halogenoalkyl. Among the cases in which one of $R^{29}$ and $R^{30}$ is a hydrogen atom or a halogen atom, the other group is particularly preferably a hydrogen atom, a halogen atom, alkyl, or alkynyl. In this case, the halogen atom is preferably a fluorine atom, a chlorine atom, or a bromine atom, the alkyl group is preferably a methyl group, and the alkynyl group is particularly preferably an ethynyl group.

Specific examples of the group represented by the above formula include pyridyl, pyrimidyl, and pyridazinyl. No particular limitation is imposed on the position, in any of these groups to which a halogen atom, alkyl, or alkynyl is linked. However, when $T^1$ is linked to the group on the 2-position of the ring in the above formula, 4-position and 5-position of the ring in the above formula are particularly preferred.

Specifically, preferred examples of the group include 2-pyridyl, 3-pyridyl, 4-pyridyl, 4-chloro-2-pyridyl, 4-fluoro-2-pyridyl, 4-bromo-2-pyridyl, 4-ethynyl-2-pyridyl, 4-chloro-3-pyridyl, 4-fluoro-3-pyridyl, 4-bromo-3-pyridyl, 4-ethynyl-3-pyridyl, 5-chloro-2-pyridyl, 5-fluoro-2-pyridyl, 5-bromo-2-pyridyl, 5-ethynyl-2-pyridyl, 4-chloro-5-fluoro-2-pyridyl, 5-chloro-4-fluoro-2-pyridyl, 5-chloro-3-pyridyl, 5-fluoro-3-pyridyl, 5-bromo-3-pyridyl, 5-ethynyl-3-pyridyl, 5-chloro-2-pyrimidyl, 5-fluoro-2-pyrimidyl, 5-bromo-2-pyrimidyl, 5-ethynyl-2-pyrimidyl, 4-chloro-3-pyridazinyl, 4-fluoro-3-pyridazinyl, 4-bromo-3-pyridazinyl, 4-ethynyl-3-pyridazinyl, 6-chloro-3-pyridazinyl, 6-fluoro-3-pyridazinyl, 6-bromo-3-pyridazinyl, and 6-ethynyl-3-pyridazinyl.

Among them, particularly preferred are 2-pyridyl, 3-pyridyl, 4-pyridyl, 4-chloro-2-pyridyl, 4-fluoro-2-pyridyl, 4-bromo-2-pyridyl, 4-ethynyl-2-pyridyl, 4-chloro-3-pyridyl, 4-fluoro-3-pyridyl, 4-bromo-3-pyridyl, 4-ethynyl-3-pyridyl, 5-chloro-2-pyridyl, 5-fluoro-2-pyridyl, 5-bromo-2-pyridyl, 5-ethynyl-2-pyridyl, 4-chloro-5-fluoro-2-pyridyl, 5-chloro-4-fluoro-2-pyridyl, 5-chloro-3-pyridyl, 5-fluoro-3-pyridyl, 5-bromo-3-pyridyl, 5-ethynyl-3-pyridyl, 6-chloro-3-pyridazinyl, 6-fluoro-3-pyridazinyl, 6-bromo-3-pyridazinyl, 6-ethynyl-3-pyridazinyl, 4-chloro-3-pyridazinyl, 4-fluoro-3-pyridazinyl, 4-bromo-3-pyridazinyl, and 4-ethynyl-3-pyridazinyl.

Among them, still more preferred are 2-pyridyl, 3-pyridyl, 4-pyridyl, 5-chloro-2-pyridyl, 5-fluoro-2-pyridyl, 5-bromo-2-pyridyl, 5-ethynyl-2-pyridyl, 5-chloro-4-fluoro-2-pyridyl, 4-chloro-5-fluoro-2-pyridyl, 4-chloro-3-pyridazinyl, 4-fluoro-3-pyridazinyl, 4-bromo-3-pyridazinyl, and 4-ethynyl-3-pyridazinyl.

In the following group:

[F68]

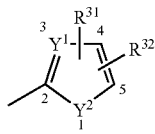

(k)

(wherein $Y^1$, $Y^2$, $R^{31}$ and $R^{32}$ have the same meanings as described above, and numerals "1" to "5" represent positions), preferably, one of $R^{31}$ and $R^{32}$ is a hydrogen atom or a halogen atom, and the other group is a hydrogen atom, cyano, a halogen atom, alkyl, alkenyl, alkynyl, or halogenoalkyl. Among the cases in which one of $R^{31}$ and $R^{32}$ is a hydrogen atom or a halogen atom, the other group is particularly preferably a hydrogen atom, a halogen atom, alkyl, or alkynyl. In these cases, the halogen atom is preferably a fluorine atom, a chlorine atom, or a bromine atom, the alkyl group is preferably methyl, and the alkynyl group is particularly preferred ethynyl.

Specific examples of the group represented by the above formula include thienyl, pyrrolyl, furyl, oxazolyl, and thiazolyl. No particular limitation is imposed on the position, in any of these groups, to which a halogen atom, alkyl, or alkynyl is linked. Among them, 4-position and 5-position are particularly preferred.

Specific examples of the group include 4-chloro-2-thienyl, 4-fluoro-2-thienyl, 4-bromo-2-thienyl, 4-ethynyl-2-thienyl, 4-chloro-2-pyrrolyl, 4-fluoro-2-pyrrolyl, 4-bromo-2-pyrrolyl, 4-ethynyl-2-pyrrolyl, 4-chloro-2-furyl, 4-fluoro-2-furyl, 4-bromo-2-furyl, 4-ethynyl-2-furyl, 5-chloro-2-thienyl, 5-fluoro-2-thienyl, 5-bromo-2-thienyl, 5-ethynyl-2-thienyl, 5-chloro-2-thiazolyl, 5-fluoro-2-thiazolyl, 5-bromo-2-thiazolyl, 5-ethynyl-2-thiazolyl, 5-chloro-2-oxazolyl, 5-fluoro-2-oxazolyl, 5-bromo-2-oxazolyl, and 5-ethynyl-2-oxazolyl. Among them, 5-chloro-2-thiazolyl, 5-fluoro-2-thiazolyl, 5-bromo-2-thiazolyl, and 5-ethynyl-2-thiazolyl are preferred.

Furthermore, in the following group:

[F69]

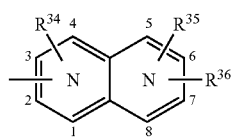

(1)

(wherein, numerals "1" to "8" represent positions, each N indicates that any one of carbon atoms of positions 1 to 4 and any one of carbon atoms of positions 5 to 8 has been substituted by a nitrogen atom, and $R^{34}$ to $R^{36}$ have the same meanings as described above), the substituent nitrogen atoms may locate at any positions, $R^{34}$ is preferably a hydrogen atom or a halogen atom. One of $R^{35}$ and $R^{36}$ is a hydrogen atom or a halogen atom, and the other group is a hydrogen atom, cyano, halogen atom, alkyl, alkenyl, alkynyl or halogenoalkyl. Among the cases in which one of $R^{35}$ and $R^{36}$ is a hydrogen atom or a halogen atom, the other group is particularly preferably a hydrogen atom, a halogen atom, alkyl or alkynyl. The halogen atom is preferably a fluorine atom, a chlorine atom, or a bromine atom, the alkyl group is a methyl group, and the alkynyl group is particularly preferably an ethynyl group.

No particular limitation is imposed on the position to which a halogen atom, alkyl, or alkynyl is linked. Specific examples of the group represented by the above formula include 6-chloro-1,5-naphthyridin-2-yl, 6-fluoro-1,5-naphthyridin-2-yl, 6-bromo-1,5-naphthyridin-2-yl, 6-ethynyl-1,5-naphthyridin-2-yl, 7-chloro-1,5-naphthyridin-2-yl, 7-fluoro-1,5-naphthyridin-2-yl, 7-bromo-1,5-naphthyridin-2-yl, 7-ethynyl-1,5-naphthyridin-2-yl, 6-chloro-1,5-naphthyridin-3-yl, 6-fluoro-1,5-naphthyridin-3-yl, 6-bromo-1,5-naphthyridin-3-yl, 6-ethynyl-1,5-naphthyridin-3-yl, 7-chloro-1,5-naphthyridin-3-yl, 7-fluoro-1,5-naphthyridin-3-yl, 7-bromo-1,5-naphthyridin-3-yl, 7-ethynyl-1,5-naphthyridin-3-yl, 6-chloro-1,7-naphthyridin-2-yl, 6-fluoro-1,7-naphthyridin-2-yl, 6-bromo-1,7-naphthyridin-2-yl, 6-ethynyl-1,7-naphthyridin-2-yl, 6-chloro-1,7-naphthyridin-3-yl, 6-fluoro-1,7-naphthyridin-3-yl, 6-bromo-1,7-naphthyridin-3-yl, 6-ethynyl-1,7-naphthyridin-3-yl, 6-chloro-1,8-naphthyridin-2-yl, 6-fluoro-1,8-naphthyridin-2-yl, 6-bromo-1,8-naphthyridin-2-yl, 6-ethynyl-1,8-naphthyridin-2-yl, 7-chloro-1,8-naphthyridin-2-yl, 7-fluoro-1,8-naphthyridin- 2-yl, 7-bromo-1,8-naphthyridin-2-yl, 7-ethynyl-1,8-naphthyridin-2-yl, 6-chloro-1,8-naphthyridin-3-yl, 6-fluoro-1,8-naphthyridin-3-yl, 6-bromo-1,8-naphthyridin-3-yl, 6-ethynyl-1,8-naphthyridin-3-yl, 7-chloro-1,8-naphthyridin-3-yl, 7-fluoro-1,8-naphthyridin-3-yl, 7-bromo-1,8-naphthyridin-3-yl, 7-ethynyl-1,8-naphthyridin-3-yl, 6-chloro-2,5-naphthyridin-3-yl, 6-fluoro-2,5-naphthyridin-3-yl, 6-bromo-2,5-naphthyridin-3-yl, 6-ethynyl-2,5-naphthyridin-3-yl, 7-chloro-2,5-naphthyridin-3-yl, 7-fluoro-2,5-naphthyridin-3-yl, 7-bromo-2,5-naphthyridin-3-yl, 7-ethynyl-2,5-naphthyridin-3-yl, 7-chloro-2,6-naphthyridin-3-yl, 7-fluoro-2,6-naphthyridin-3-yl, 7-bromo-2,6-naphthyridin-3-yl, 7-ethynyl-2,6-naphthyridin-3-yl, 6-chloro-2,8-naphthyridin-3-yl, 6-fluoro-2,8-naphthyridin-3-yl, 6-bromo-2,8-naphthyridin-3-yl, 6-ethynyl-2,8-naphthyridin-3-yl, 7-chloro-2,8-naphthyridin-3-yl, 7-fluoro-2,8-naphthyridin-3-yl, 7-bromo-2,8-naphthyridin-3-yl, and 7-ethynyl-2,8-naphthyridin-3-yl.

Particularly preferred examples of the group include 7-chloro-2,5-naphthyridin-3-yl, 7-fluoro-2,5-naphthyridin-3-yl, 7-bromo-2,5-naphthyridin-3-yl, and 7-ethynyl-2,5-naphthyridin-3-yl.

In addition to the above 12 groups (a) to (1), a thienopyrrolyl group which may be substituted is also preferred. The thienopyrrolyl group may have 1 to 3 substituents, and examples of the substituent(s) include hydroxyl, nitro, amino, cyano, a halogen atom, alkyl, alkenyl, alkynyl, halogenoalkyl, hydroxyalkyl, alkoxy, alkoxyalkyl, carboxyl, carboxyalkyl, acyl, carbamoyl, N-alkylcarbamoyl, N,N-dialkylcarbamoyl, alkoxycarbonyl, amidino, and alkoxycarbonylalkyl. Among them, cyano, a halogen atom, alkyl, alkenyl, alkynyl, and halogenoalkyl are preferred.

Specifically, preferred examples include 2-chlorothieno[2,3-b]pyrrol-5-yl, 2-fluorothieno[2,3-b]pyrrol-5-yl, 2-bromothieno[2,3-b]pyrrol-5-yl, and 2-ethynylthieno[2,3-b]pyrrol-5-yl.

Next will be described, in detail, the following group:

[F70]

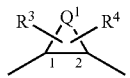

[wherein $Q^1$, $R^3$, and $R^4$ have the same meanings as described above, and 1 and 2 denotes positions].

The moiety having a cyclic structure containing the above group $Q^1$ is a 3- to 10-membered divalent cyclic hydrocarbon group which may have one double bond, or a 5- to 12-membered divalent heterocyclic group which has 2 heteroatoms. The moiety is preferably a 3- to 8-membered divalent cyclic hydrocarbon group or a 5- to 8-membered divalent heterocyclic group, more preferably a 5- to 7-membered divalent cyclic hydrocarbon group or a 5- to 7-membered divalent heterocyclic group. Of these, preferred is a group in which $Q^1$ represents a C3-C6 alkylene group or a group $(CH_2)_m$—$CH_2$-A-$CH_2$—$(CH_2)_n$— (wherein each of m and n is independently 0 or 1, and A has the same meaning as described above). Particularly preferred is a group in which $Q^1$ represents a C4 alkylene group.

The cyclic hydrocarbon or heterocyclic group may have cis-formation or trans-formation with respect to the 1-position and the 2-position. In the case of 5-membered ring, trans-formation is preferred. In the case of 6- or 7-membered ring, cis- and trans-formations are both preferred.

The above substituents $R^3$ and $R^4$ will next be described in detail. The halogen atom is a fluorine atom, chlorine atom, bromine atom, or iodine atom. Examples of the alkyl group include a linear, branched, or cyclic $C_1$-$C_6$ alkyl (e.g., methyl, cyclopropyl, isobutyl), examples of the halogenoalkyl group include a group corresponding to the above alkyl group which has been substituted by 1 to 3 halogen atoms (e.g., chloromethyl, 1-bromoethyl, trifluoromethyl). Examples of the cyanoalkyl group include a group corresponding to the above $C_1$-$C_6$ alkyl group which has been substituted by a single cyano group (e.g., cyanomethyl, 1-cyanoethyl). Examples of the alkenyl group include a linear or branched C2-C6 alkenyl group having a single double bond (e.g., vinyl, allyl). Examples of the alkynyl group include a linear or branched C2-C6 alkynyl group having a single triple bond (e.g., ethynyl, propynyl). Examples of the acyl group include a $C_1$-$C_6$ alkanoyl group (e.g., formyl, acetyl), a $C_7$-$C_{15}$ aroyl group (e.g., benzoyl, naphthoyl), and an arylalkanoyl group corresponding to the above $C_1$-$C_6$ alkanoyl group which has been substituted by one of the $C_6$-$C_{14}$ aryl groups mentioned above (e.g., phenacetyl). Examples of the acylalkyl group include a group corresponding to the above $C_1$-$C_6$ alkyl group which has been substituted by one of the acyl groups mentioned above (e.g., acetylmethyl). Examples of the alkoxy group include a linear, branched, or cyclic $C_1$-$C_6$ alkoxy group (e.g., methoxy, cyclopropoxy, isopropoxy). Examples of the alkoxyalkyl groups include a group corresponding to the above $C_1$-$C_6$ alkyl group which has been substituted by one of the $C_1$-$C_6$ alkoxy groups mentioned above (e.g., methoxymethyl, ethoxymethyl). Examples of the hydroxyalkyl groups include a group corresponding to the above $C_1$-$C_6$ alkyl group which has been substituted by a single hydroxyl group (e.g., hydroxymethyl, 1-hydroxyethyl). Examples of the carboxyalkyl groups include a group corresponding to the above $C_1$-$C_6$ alkyl group which has been substituted by a single carboxyl group (e.g., carboxymethyl, 1-carboxyethyl). Examples of the alkoxycarbonyl group include a group formed of the above $C_1$-$C_6$ alkoxy groups and a carbonyl group (e.g., methoxycarbonyl, ethoxycarbonyl). Examples of the alkoxycarbonylalkyl group include a group corresponding to the above $C_1$-$C_6$ alkyl group which has been substituted by one of the alkoxycarbonyl groups mentioned above (e.g., methoxycarbonylethyl, ethoxycarbonylethyl). Examples of the carbamoylalkyl group include a group corresponding to the above $C_1$-$C_6$ alkyl group which has been substituted by a carbamoyl group (e.g., carbamoylmethyl, carbamoylethyl).

The 3- to 6-membered heterocyclic group which may have a substituent is a saturated or unsaturated 3- to 6-membered heterocyclic group which may have 1 to 3 heteroatoms (e.g., nitrogen atom, oxygen atom, sulfur atom), and the heterocyclic group may have a substituent such as hydroxy, a halogen atom, amino, $C_1$-$C_6$ alkyl, oxo, or halogenoalkyl. Examples of the 3- to 6-membered heterocyclic group include pyrrolyl, thienyl, pyrazolyl, imidazolyl, pyrazolinyl, oxazolyl, oxazolinyl, oxadiazolyl, oxazolidinyl, thiazolyl, thiazolinyl, thiadiazolyl, furazanyl, pyranyl, pyridyl, pyrimidyl, pyridazinyl, pyrrolidinyl, piperazinyl, piperidinyl, oxazinyl, oxadiazinyl, morpholinyl, thiazinyl, thiadiazinyl, thiomorpholinyl, tetrazolyl, triazolyl, and triazinyl.

Specific examples of the 3- to 6-membered heterocyclic group which may have a substituent include thiazolyl, 4,5-dihydrothiazolyl, oxazolyl, 4,5-dihydroxazolyl, 5-methyloxazolyl, imidazolyl, pyrrolidinyl, 3-hydroxypyrrolidinyl, piperidyl, piperazinyl, morpholinyl, thiomorpholinyl, 1,1-dioxothiomorpholinyl, tetrahydropyranyl, pyridyl, 1,2,4-oxadiazolyl, 3-methyl-1,2,4-oxadiazolyl, 5-methyl-1,2,4-oxadiazolyl, 1,3,4-oxadiazolyl, 5-methyl-1,3,4-oxadiazolyl, 5-(trifluoromethyl)-1,3,4-oxadiazolyl, 1,3-oxazolyl, 1,3,4-thiadiazolyl, 5-methyl-1,3,4-thiadiazolyl, and 1,3-oxazolidinyl.

Examples of the 3- to 6-membered heterocyclic alkyl group which may have a substituent include a group corresponding to the above 3- to 6-membered heterocyclic group which may have a substituent, which group has been substituted by a single alkyl group (e.g., triazolylmethyl, 4,5-dihydrothiazolylmethyl, morpholinylmethyl, 1,1-dioxothiomorpholinylmethyl). Examples of the aryl group include C6-C14 aryl groups such as phenyl and naphthyl, and the aryl group may be substituted by one to three groups selected from among the above $C_1$-$C_6$ alkyl group, the above $C_1$-$C_6$ alkanoyl, hydroxyl, nitro, cyano, halogen atoms, the above $C_2$-$C_6$ alkenyl, the above $C_2$-$C_6$ alkynyl, the above $C_1$-$C_6$ halogenoalkyl, the above $C_1$-$C_6$ alkoxy, carboxy, carbamoyl, the above $C_1$-$C_6$ alkoxycarbonyl, and other groups. Examples of the aralkyl group include a group corresponding to the above $C_1$-$C_6$ alkyl group which has been substituted by one of the $C_6$-$C_{14}$ aryl groups (e.g., benzyl, phenethyl). It should be noted that, in the above description, no particular limitation is imposed on the position of the substitution.

Examples of the acylamino group which may have a substituent include a group corresponding to the above $C_1$-$C_6$ acyl which has been substituted by an amino group (e.g., formylamino and acetylamino) and also include an acyl group which has been substituted by a single or a plurality of groups such as halogen atoms, hydroxyl, $C_1$-$C_6$ alkoxy, amino, N—$C_1$-$C_6$ alkylamino, N,N-di-$C_1$-$C_6$ alkylamino, carboxyl, and $C_2$-$C_6$ alkoxycarbonyl (e.g., 2-methoxyacetylamino, 3-aminopropionylamino). Examples of the acylaminoalkyl group include a group corresponding to the above $C_1$-$C_6$ acylamino group which has been substituted by the above $C_1$-$C_6$ alkyl group (e.g., formylaminomethyl and acetylaminomethyl). Examples of the aminoalkyl group include a group corresponding to the above $C_1$-$C_6$ alkyl which has been substituted by a single amino group (e.g., aminomethyl and 1-aminoethyl). Examples of the N-alkylaminoalkyl group include a group corresponding to an amino-($C_1$-$C_6$ alkyl) group which has been substituted by a single $C_1$-$C_6$ alkyl group at the nitrogen atom of the amino-$C_1$-$C_6$ alkyl group (e.g., N-methylamino methyl, N-methylaminoethyl). Examples of the N,N-dialkylaminoalkyl group include a group corresponding to an amino-($C_1$-$C_6$ alkyl) group which has been substituted by two $C_1$-$C_6$ alkyl groups at the nitrogen atom of the N,N-dialkylaminoalkyl group (e.g., N,N-dimethylaminomethyl and N-ethyl-N-methylaminoethyl). Examples of the N-alkenylcarbamoyl group include a group corresponding to a carbamoyl group which has been substituted by a linear or branched $C_2$-$C_6$ alkenyl group (e.g., allylcarbamoyl). Examples of the N-alkenylcarbamoylalkyl group include a group corresponding to a $C_1$-$C_6$ alkyl group which has been substituted by the above N—($C_2$-$C_6$ alkenyl)carbamoyl group (e.g., allylcarbamoylethyl). Examples of the N-alkenyl-N-alkylcarbamoyl group include a group corresponding to the above N—($C_2$-$C_6$ alkenyl)carbamoyl group which has been substituted by a linear or branched $C_1$-$C_6$ alkyl group at the nitrogen atom of the N-alkenyl-N-alkylcarbamoyl group (e.g., N-allyl-N-methylcarbamoyl). Examples of the N-alkenyl-N-alkylcarbamoylalkyl group include a group corresponding to the above N—($C_2$-$C_6$ alkenyl)carbamoylalkyl group which has been substituted by a linear or branched $C_1$-$C_6$ alkyl group at the nitrogen atom of the N-alkenyl-N-alkylcarbamoylalkyl group (e.g., N-allyl-N-methylcarbamoylmethyl). Examples of the N-alkoxycarbamoyl group include a group corresponding to a carbamoyl group which has been substituted by a linear or branched $C_1$-$C_6$ alkoxy group (e.g., methoxycarbamoyl). Examples of the N-alkoxycarbamoylalkyl include a group corresponding to a linear or branched $C_1$-$C_6$ alkyl group which has been substituted by the above N—($C_1$-$C_6$ alkoxy)carbamoyl group (e.g., methoxycarbamoylmethyl). Examples of the N-alkyl-N-alkoxycarbamoyl group include a group corresponding to a carbamoyl group which has been substituted by a linear or branched $C_1$-$C_6$ alkoxy and $C_1$-$C_6$ alkyl groups (e.g., N-ethyl-N-methoxycarbamoyl). Examples of the N-alkyl-N-alkoxycarbamoylalkyl group include a group corresponding to a linear or branched $C_1$-$C_6$ alkyl group which has been substituted by the above N—($C_1$-$C_6$ alkyl)-N—($C_1$-$C_6$ alkoxy)carbamoyl group (e.g., N-ethyl-N-methoxycarbamoylmethyl). Examples of the carbazoyl group which may be substituted by 1 to 3 alkyl groups a carbazoyl group and a group corresponding to a carbazoyl group which has been substituted by 1 to 3 linear or branched $C_1$-$C_6$ alkyl groups (e.g., 1-methylcarbazoyl and 1,2-dimethylcarbazoyl). Examples of the alkylsulfonyl group include a linear, branched, or cyclic $C_1$-$C_6$ alkylsulfonyl group (e.g., methanesulfonyl).

Examples of the alkylsulfonylalkyl group include a group corresponding to a linear or branched $C_1$-$C_6$ alkyl group which has been substituted by the above $C_1$-$C_6$ alkylsulfonyl group (e.g., methanesulfonylmethyl). Examples of the alkoxyimino group include a $C_1$-$C_6$ alkoxyimino group (e.g., methoxyimino and ethoxyimino). Examples of the alkoxycarbonylalkylamino group include a group corresponding to an amino group which has been substituted by one of the above $C_1$-$C_6$ alkoxycarbonylalkyl groups (e.g., methoxycarbonylmethylamino and ethoxycarbonylpropylamino). Examples of the carboxyalkylamino group include a group corresponding to an amino group which has been substituted by one of the above carboxy $C_1$-$C_6$ alkyl groups (e.g., carboxymethylamino and carboxyethylamino). Examples of the alkoxycarbonylamino group include a group corresponding to an amino group which has been substituted by one of the above $C_1$-$C_6$ alkoxycarbonyl groups (e.g., methoxycarbonylamino and tert-butoxycarbonylamino). Examples of the alkoxycarbonylaminoalkyl group include a group corresponding to the above alkyl group which has been substituted by one of the above $C_1$-$C_6$ alkoxycarbonylamino groups (e.g., methoxycarbonylaminomethyl and tert-butoxycarbonylaminoethyl).

The N-alkylcarbamoyl group whose alkyl may or may not be substituted is a carbamoyl group which has been substituted by a linear, branched, or cyclic $C_1$-$C_6$ alkyl group which may be substituted by, for example, hydroxyl, amino, N—$C_1$-$C_6$ alkylamino, amidino, halogen atom, carboxyl, cyano, carbamoyl, $C_1$-$C_6$ alkoxy, $C_1$-$C_6$ alkanoyl, $C_1$-$C_6$ alkanoylamino, or $C_1$-$C_6$ alkylsulfonylamino. Examples include N-methylcarbamoyl, N-ethylcarbamoyl, N-isopropylcarbamoyl, N-cyclopropylcarbamoyl, N-(2-hydroxyethyl)carbamoyl, N-(2-fluoroethyl)carbamoyl, N-(2-cyanoethyl)carbamoyl, N-(2-methoxyethyl)carbamoyl, N-carboxymethylcarbamoyl, N-(2-aminoethyl)carbamoyl, and N-(2-amidinoethyl)carbamoyl. The N,N-dialkylcarbamoyl group whose alkyls may or may not be substituted is a carbamoyl group which has been substituted by two linear, branched, or cyclic $C_1$-$C_6$ alkyl groups which may be substituted by, for example, hydroxy, amino, N—$C_1$-$C_6$ alkylamino, amidino, halogen atom, carboxyl, cyano, carbamoyl, $C_1$-$C_6$ alkoxy, $C_1$-$C_6$ alkanoyl, $C_1$-$C_6$ alkanoylamino, and $C_1$-$C_6$ alkylsulfonylamino. Examples include N,N-dimethylcarbamoyl, N,N-diethylcarbamoyl, N-ethyl-N-methylcarbamoyl, N-isopropyl-N-methylcarbamoyl, N-(2-hydroxyethyl)-N-methylcarbamoyl, N,N-bis(2-hydroxyethyl)carbamoyl, N,N-bis(2-fluoroethyl)carbamoyl, N-(2- cyanoethyl)-N-methylcarbamoyl, N-(2-methoxyethyl)-N-methylcarbamoyl, N-carboxymethyl-N-methylcarbamoyl, and N,N-bis(2-aminoethyl)carbamoyl. Examples of the N-alkylcarbamoylalkyl group whose alkyl may or may not be substituted include a group corresponding to a linear or branched $C_1$-$C_6$ alkyl group which has been substituted by the above N-alkylcarbamoyl group whose $C_1$-$C_6$ alkyl may or may not be substituted (e.g., N-methylcarbamoylmethyl and N-(2-hydroxyethyl)carbamoylmethyl). Examples of the N,N-dialkylcarbamoylalkyl group whose alkyls may or may not be substituted include a group corresponding to a linear or branched $C_1$-$C_6$ alkyl group which has been substituted by the above N,N-dialkylcarbamoyl group whose $C_1$-$C_6$ alkyls may or may not be substituted (e.g., N,N-dimethylcarbamoylmethyl and N-(2-hydroxyethyl)-N-methylcarbamoylmethyl).

Examples of the 3- to 6-membered heterocyclic carbonyl group which may have a substituent include a group formed of a carbonyl group and the above 3- to 6-membered heterocyclic group which may have a substituent (e.g., aziridinylcarbonyl, azetidinylcarbonyl, 3-hydroxyazetidinylcarbonyl, 3-methoxyazetidinylcarbonyl, pyrrolidinylcarbonyl, 3-hydroxypyrrolidinylcarbonyl, 3-fluoropyrrolidinylcarbonyl, piperidylcarbonyl, piperazinylcarbonyl, morpholinylcarbonyl, thiomorpholinylcarbonyl, 1,1-dioxothiomorpholinylcarbonyl, tetrahydropyranylcarbonyl, pyridylcarbonyl, furoyl, and thiophenecarbonyl). Examples of the 3- to 6-membered heterocyclic carbonylalkyl group which may have a substituent include a group corresponding to the above $C_1$-$C_6$ alkyl group which has been substituted by one of the above 3- to 6-membered heterocyclic carbonyl groups which may have a substituent (e.g., azetidinylcarbonylmethyl and pyrrolidinylcarbonylethyl).

Examples of the 3- to 6-membered heterocyclic carbonyloxyalkyl group which may have a substituent include a group corresponding to the above $C_1$-$C_6$ alkyl group which has been substituted by one of the 3- to 6-membered heterocyclic carbonyloxy groups formed of an oxygen atom and the above 3- to 6-membered heterocyclic carbonyl group which may have a substituent (e.g., piperidinylcarbonyloxyethyl and morpholinylcarbonyloxymethyl). Examples of the carbamoyloxyalkyl group include a group corresponding to the above $C_1$-$C_6$ alkyl group which has been substituted by one of the carbamoyloxy groups formed of a carbamoyl group and an oxygen atom (e.g., carbamoyloxymethyl and carbamoyloxyethyl). Examples of the N-alkylcarbamoyloxyalkyl group include a group corresponding to the above $C_1$-$C_6$ alkyl group which has been substituted by one of the N-alkylcarbamoyloxy groups formed of an oxygen atom and the above N-alkylcarbamoyl group whose $C_1$-$C_6$ alkyl may or may not be substituted (e.g., N-methylcarbamoyloxymethyl and N-methylcarbamoyloxyethyl). Examples of the N,N-dialkylcarbamoyloxyalkyl group include a group corresponding to the above $C_1$-$C_6$ alkyl group which has been substituted by one of the N,N-dialkylcarbamoyloxy groups formed of an oxygen atom and the above N,N-dialkylcarbamoyl group whose $C_1$-$C_6$ alkyls may or may not be substituted (e.g., N,N-dimethylcarbamoyloxymethyl and N-ethyl-N-methylcarbamoyloxyethyl).

Examples of the alkylsulfonylamino group include a group corresponding to an amino group which has been substituted by one of the above alkylsulfonyl groups having a $C_1$-$C_6$ alkyl group (e.g., methylsulfonylamino and isopropylsulfonylamino). Examples of the arylsulfonylamino group include a group corresponding to an amino group which has been substituted by one of the above arylsulfonyl groups having an aryl group (e.g., phenylsulfonylamino and naphthylsulfonylamino). Examples of the alkylsulfonylaminoalkyl group include a group corresponding to the above $C_1$-$C_6$ alkyl group which has been substituted by one of the above $C_1$-$C_6$ alkylsulfonylamino groups (e.g., methylsulfonylaminomethyl and methylsulfonylaminoethyl). Examples of the arylsulfonylaminoalkyl group include a group corresponding to the above $C_1$-$C_6$ alkyl group which has been substituted by one of the above arylsulfonylamino groups (e.g., phenylsulfonylaminomethyl and naphthylsulfonylaminoethyl). Examples of the alkylsulfonylaminocarbonyl group include a group formed of the above $C_1$-$C_6$ alkylsulfonylamino group and a carbonyl group (e.g., methylsulfonylaminocarbonyl and isopropylsulfonylaminocarbonyl). Examples of the arylsulfonylaminocarbonyl group include a group formed of the above arylsulfonylamino group and a carbonyl group (e.g., phenylsulfonylaminocarbonyl and naphthylsulfonylaminocarbonyl). Examples of the alkylsulfonylaminocarbonylalkyl group include a group corresponding to the above $C_1$-$C_6$ alkyl group which has been substituted by the above $C_1$-$C_6$ alkylsulfonylaminocarbonyl group (e.g., methylsulfonylaminocarbonylmethyl and isopropylsulfimylaminocarbonylmethyl). Examples of the arylsulfonylaminocarbonylalkyl group include a group corresponding to the above $C_1$-$C_6$ alkyl group which has been substituted by the above arylsulfonylaminocarbonyl group (e.g., phenylsulfonylaminocarbonylmethyl and naphthylsulfonylaminocarbonylmethyl). Examples of the alkoxycarbonylalkyloxy group include a group corresponding to the above $C_1$-$C_6$ alkoxy group which has been substituted by the above alkoxycarbonyl group (e.g., methoxycarbonylmethyloxy).

The acyloxy group is a group formed of the above acyl group and an oxygen atom (e.g., formyloxy and acetyloxy). Examples of the acyloxyalkyl group include a group corresponding to the above $C_1$-$C_6$ alkyl group which has been substituted by the above acyloxy group (e.g., formyloxymethyl and acetyloxymethyl). Examples of the aralkyloxy group include a group corresponding to the above $C_1$-$C_6$ alkoxy group which has been substituted by the above aryl group (e.g., benzyloxy and naphthylmethoxy). Examples of the carboxyalkyloxy group include a group corresponding to the above alkoxy group which has been substituted by a carboxyl group (e.g., carboxymethoxy and carboxyethoxy).

Examples of the arylsulfonyl group include a $C_6$-$C_{14}$ arylsulfonyl group (e.g., phenylsulfonyl and naphthylsulfonyl). Examples of the alkoxycarbonylalkylsulfonyl group include a group formed of the above $C_1$-$C_6$ alkoxycarbonylalkyl group and a sulfonyl group (e.g., methoxycarbonylethylsulfonyl, and ethoxycarbonylethylsulfonyl). Examples of the carboxyalkylsulfonyl group include a group formed of the above carboxyalkyl group and a sulfonyl group (e.g., carboxymethylsulfonyl and carboxyethylsulfonyl). Examples of the alkoxycarbonylacyl group include a group formed of the above alkoxycarbonylalkyl group and a carbonyl group (e.g., methoxycarbonylmethylcarbonyl and ethoxycarbonylmethylcarbonyl). Examples of the alkoxyalkyloxycarbonyl group include a group corresponding to the above alkoxycarbonyl group which has been substituted by one of the above $C_1$-$C_6$ alkoxy groups (e.g., methoxymethyloxycarbonyl and methoxyethyloxycarbonyl). Examples of the hydroxyacyl group include a group corresponding to the above acyl group (including $C_1$-$C_6$ alkanoyl and aroyl) which has been substituted by one hydroxyl group (e.g., glycoloyl, lactoyl, and benziloyl). Examples of the alkoxyacyl group include a group corresponding to the above acyl group which has been substituted by one of the above $C_1$-$C_6$ alkoxy groups (e.g., methoxyacetyl and ethoxyacetyl). Examples of the halogenoacyl group include a group formed of the above halogenoalkyl group and a carbonyl group (e.g., chloromethylcarbonyl and trifluoromethylcarbonyl). Examples of the carboxyacyl group include a group corresponding to the above acyl group which has been substituted by one carboxyl group (e.g., carboxyacetyl and 2-carboxypropionyl). Examples of the aminoacyl group include a group corresponding to the above acyl group (including $C_1$-$C_6$ alkanoyl and aroyl) which has been substituted by one amino group (e.g., aminomethylcarbonyl and 1-aminoethylcarbonyl). Examples of the acyloxyacyl group include a group formed of the above acyloxyalkyl group and a carbonyl group (e.g., formyloxymethylcarbonyl and acetyloxymethylcarbonyl). Examples of the acyloxyalkylsulfonyl group include a group formed of the above acyloxyalkyl group and a sulfonyl group (e.g., formyloxymethylsulfonyl and acetyloxymethylsulfonyl). Examples of the hydroxyalkylsulfonyl group include a group formed of the above $C_1$-$C_6$ hydroxyalkyl group and a sulfonyl group (e.g., hydroxymethylsulfonyl and 1-hydroxyethylsulfonyl). Examples of the alkoxyalkylsulfonyl group include a group formed of the above $C_1$-$C_6$ alkoxyalkyl group and a sulfonyl group (e.g., methoxymethylsulfonyl and ethoxyethylsulfonyl).

Examples of the 3- to 6-membered heterocyclic sulfonyl group which may have a substituent include a group formed of a sulfonyl group and the above 3- to 6-membered heterocyclic ring which may have a substituent (e.g., aziridinylsulfonyl, azetidinylsulfonyl, pyrrolidinylsulfonyl, piperidylsulfonyl, piperazinylsulfonyl, morpholinylsulfonyl, and tetrahydropyranylsulfonyl). Examples of the 3- to 6-membered heterocyclic oxy group which may have a substituent include a group farmed of an oxygen atom and the above 3- to 6-membered heterocyclic ring which may have a substituent (e.g., tetrahydrofuranyloxy). Examples of the N-alkylaminoacyl include a group corresponding to the aminoacyl group whose nitrogen atom has been substituted by one of the above $C_1$-$C_6$ alkyl (e.g., N-methylamino acetyl and N-ethylaminoacetyl). Examples of the N,N-dialkylaminoacyl include a group corresponding to the above aminoacyl group whose nitrogen atom has been substituted by two $C_1$-$C_6$ alkyl groups (e.g., N,N-dimethylaminoacetyl and N-ethyl-N-methylaminoacetyl). Examples of the N,N-dialkylcarbamoylacyl group whose alkyl groups may or may not be substituted include a group corresponding to the above acyl group which has been substituted by the above N,N-dialkylcarbamoyl group whose $C_1$-$C_6$ alkyl groups may or may not be substituted (e.g., N,N-dimethylcarbamoylacetyl, N,N-diethylcarbamoylacetyl, and N-ethyl-N-methylcarbamoylacetyl). Examples of the N,N-dialkylcarbamoylalkylsulfonyl group whose alkyl groups may or may not be substituted include a group formed of a sulfonyl group and the above N,N-dialkylcarbamoyl group whose $C_1$-$C_6$ alkyl groups may or may not be substituted (e.g., N,N-dimethylcarbamoylmethylsulfonyl and N-(2-hydroxyethyl)-N-methylcarbamoylmethylsulfonyl). Examples of the alkylsulfonylacyl group include a group corresponding to an acyl group which has been substituted by one of the above alkylsulfonyl group having a $C_1$-$C_6$ alkyl group (e.g., methylsulfonylacetyl and isopropylsulfonylacetyl).

Examples of the N-arylcarbamoyl group include a group corresponding to a carbamoyl group which has been substituted by the above aryl group (e.g., phenylcarbamoyl and naphthylcarbamoyl). Examples of the N-(3- to 6-membered heterocyclic) carbamoyl group include a group corresponding to a carbamoyl group which has been substituted by the above 3- to 6-membered heterocyclic group which may have a substituent (e.g., pyridylcarbamoyl and thienylcarbamoyl). Examples of the N-alkyl-N-arylcarbamoyl group include a group corresponding to the above N-arylcarbamoyl group whose nitrogen atom has been substituted by a linear or branched $C_1$-$C_6$ alkyl group (e.g., N-methyl-N-phenylcarbamoyl). Examples of the N-alkyl-N-(3- to 6-membered heterocyclic) carbamoyl group include a group corresponding to the above N-(3- to 6-membered heterocyclic) carbamoyl group whose nitrogen atom has been substituted by a linear or branched $C_1$-$C_6$ alkyl group (e.g., N-methyl-N-thienylcarbamoyl). Examples of the N-arylcarbamoylalkyl group include a group corresponding to a linear or branched $C_1$-$C_6$ alkyl group which has been substituted by the above N-arylcarbamoyl group (e.g., phenylcarbamoylmethyl). Examples of the N-3- to 6-membered heterocyclic carbamoylalkyl group include a group corresponding to a linear or branched $C_1$-$C_6$ alkyl group which has been substituted by the above N-(3- to 6-membered heterocyclic) carbamoyl group (e.g., pyridylcarbamoylmethyl). Examples of the N-alkyl-N-arylcarbamoylalkyl group include a group corresponding to the above N-arylcarbamoylalkyl group whose nitrogen atom has been substituted by a linear or branched $C_1$-$C_6$ alkyl group (e.g., N-methyl-N-phenylcarbamoylmethyl). Examples of the N-alkyl-N-(3- to 6-membered heterocyclic) carbamoylalkyl group include a group corresponding to the above N-(3- to 6-membered heterocyclic) carbamoylalkyl group whose nitrogen atom has been substituted by a linear or branched $C_1$-$C_6$ alkyl group (e.g., N-methyl-N-thienylcarbamoylmethyl).

The aminocarbothioyl group is the group represented by —C(=S)—NH$_2$. The N-alkylaminocarbothioyl group is an aminothiocarbonyl group which has been substituted by one of the above alkyl groups, such as (methylamino)carbothioyl or (ethylamino)carbothioyl. The N,N-dialkylaminocarbothioyl group is an aminothiocarbonyl group which has been substituted by two of the above alkyl groups, such as (dimethylamino)carbothioyl, or (diethylamino)carbothioyl, (ethylmethylamino)carbothioyl. Examples of the alkylthioalkyl group include a group corresponding to a linear, branched, or cyclic $C_1$-$C_6$ alkylthio group which has been substituted by a linear, branched, or cyclic $C_1$-$C_6$ alkyl group (e.g., methylthiomethyl and 1-methylthioethyl). Examples of the N-acyl-N-alkylaminoalkyl group include a group corresponding to an amino-$C_1$-$C_6$ alkyl group whose nitrogen atom has been substituted by a $C_1$-$C_6$ alkyl group (e.g., N-acetyl-N-methylaminomethyl). Examples of the alkoxyalkyl(thiocarbonyl) group is a group formed of the above alkoxyalkyl group and a thiocarbonyl group, such as 2-ethoxyethanethioyl.

The alkylene group is a C1-C5 linear or branched alkylene group, such as methylene, ethylene, or propylene. The alkenylene group is a C2-C5 alkenylene group having one double bond, such as vinylene or propenylene. Examples of the alkylenedioxy group include C1-C5 alkylenedioxy groups such as methylenedioxy, ethylenedioxy, and propylenedioxy. The carbonyldioxy group is the group represented by —O—C(=O)—O—. It should be noted that, in the above description, no particular limitation is imposed on the position of the substitution.

Among these substituents represented by $R^3$ or $R^4$, preferred are, for example, hydrogen atom, hydroxyl, alkyl, alkenyl, alkynyl, halogen atom, halogenoalkyl, amino, hydroxyimino, alkoxyimino, aminoalkyl, N-alkylaminoalkyl, N,N-dialkylaminoalkyl, acyl, acylalkyl, acylamino which may have a substituent, acylaminoalkyl, alkoxy, alkoxyalkyl, hydroxyalkyl, carboxyl, carboxyalkyl, alkoxycarbonyl, alkoxycarbonylalkyl, alkoxycarbonylamino, alkoxycarbonylaminoalkyl, carbamoyl, N-alkylcarbamoyl groups whose alkyl group may or may not be substituted, N,N-dialkylcarbamoyl groups whose alkyl groups may or may not be substituted, N-alkenylcarbamoyl, N-alkenylcarbamoylalkyl, N-alkenyl-N-alkylcarbamoyl, N-alkenyl-N-alkylcarbamoylalkyl, N-alkoxycarbamoyl, N-alkyl-N-alkoxycarbamoyl, N-alkoxycarbamoylalkyl, N-alkyl-N-alkoxycarbamoylalkyl, carbazoyl groups which may be substituted by 1 to 3 alkyl groups, alkylsulfonyl, alkylsulfonylalkyl, 3- to 6-membered heterocyclic carbonyl groups which may have a substituent, 3- to 6-membered heterocyclic carbonyloxyalkyl groups which may have a substituent, 3- to 6-membered heterocyclic group groups which may have a substituent, carbamoylalkyl, carbamoyloxyalkyl, N-alkylcarbamoyloxyalkyl, N,N-dialkylcarbamoyloxyalkyl, N-alkylcarbamoylalkyl groups whose alkyl group may or may not be substituted, N,N-dialkylcarbamoylalkyl groups whose alkyl groups may or may not be substituted, alkylsulfonylamino, alkylsulfonylaminoalkyl, oxo, acyloxy, acyloxyalkyl, arylsulfonyl, alkoxycarbonylalkylsulfonyl, carboxyalkylsulfonyl, alkoxycarbonylacyl, carboxyacyl, alkoxyalkyloxycarbonyl, halogenoacyl, N,N-dialkylaminoacyl, acyloxyacyl, hydroxyacyl, alkoxyacyl, alkoxyalkylsulfonyl, N,N-dialkylcarbamoylacyl, N,N-dialkylcarbamoylalkylsulfonyl, alkylsulfonylacyl, aminocarbothioyl, N-alkylaminocarbothioyl, N,N-dialkylaminocarbothioyl, and alkoxyalkyl(thiocarbonyl). In addition, alkylene, alkenylene, alkylenedioxy, carbonyldioxy, and other groups which are formed by $R^3$ and $R^4$ together are preferred.

Preferred is the case where $R^3$ is a hydrogen atom, and $R^4$ is any one of the substituents listed above as preferred examples thereof. In this case, $R^4$ is more preferably a hydrogen atom, hydroxyl, alkyl, halogen atom, hydroxyimino, N-alkylaminoalkyl, N,N-dialkylaminoalkyl, acyl, acylamino groups which may have a substituent, acylaminoalkyl, alkoxy, alkoxyalkyl, hydroxyalkyl, carboxyl, alkoxycarbonyl, alkoxycarbonylalkyl, alkoxycarbonylamino, carbamoyl, N-alkylcarbamoyl groups whose alkyl group may or may not be substituted, N,N-dialkylcarbamoyl groups whose alkyl group may or may not be substituted, N-alkenylcarbamoyl, N-alkenylcarbamoylalkyl, N-alkenyl-N-alkylcarbamoyl, N-alkenyl-N-alkylcarbamoylalkyl, N-alkoxycarbamoyl, N-alkyl-N-alkoxycarbamoyl, N-alkyl-N-alkoxycarbamoylalkyl, carbazoyl group which may be substituted by 1 to 3 alkyl groups, alkylsulfonyl, alkylsulfonylalkyl, 3- to 6-membered heterocyclic carbonyl group which may have a substituent, 3- to 6-membered heterocyclic carbonyloxyalkyl group which may have a substituent, 3- to 6-membered heterocyclic group which may have a substituent, carbamoylalkyl, N,N-dialkylcarbamoyloxyalkyl, N-alkylcarbamoylalkyl group whose alkyl group may or may not be substituted, N,N-dialkylcarbamoylalkyl group whose alkyl groups may or may not be substituted, alkylsulfonylamino, alkylsulfonylaminoalkyl, acyloxy, arylsulfonyl, alkoxycarbonylalkylsulfonyl, carboxyalkylsulfonyl, alkoxycarbonylacyl, carboxyacyl, alkoxyalkyloxycarbonyl, halogenoacyl, N,N-dialkylaminoacyl, acyloxyacyl, hydroxyacyl, alkoxyacyl, alkoxyalkylsulfonyl, N,N-dialkylcarbamoylacyl, N,N-dialkylcarbamoylalkylsulfonyl, alkylsulfonylacyl, aminocarbothioyl, N-alkylaminocarbothioyl, N,N-dialkylaminocarbothioyl, and alkoxyalkyl(thiocarbonyl), among others.

Among these groups, as $R^4$, more preferred are a hydrogen atom, hydroxyl, alkyl, N,N-dialkylaminoalkyl, acylamino group which may have a substituent, acylaminoalkyl, alkoxy, alkoxyalkyl, hydroxyalkyl, alkoxycarbonyl, alkoxycarbonylamino, carbamoyl, N-alkylcarbamoyl whose alkyl group may or may not be substituted, N,N-dialkylcarbamoyl whose alkyl groups may or may not be substituted, N-alkenylcarbamoyl, N-alkenylcarbamoylalkyl, N-alkenyl-N-alkylcarbamoyl, N-alkenyl-N-alkylcarbamoylalkyl, N-alkyl-N-alkoxycarbamoyl, carbazoyl which may be substituted by 1 to 3 alkyl groups, alkylsulfonyl, alkylsulfonylalkyl, 3- to 6-membered heterocyclic carbonyl group which may have a substituent, 3- to 6-membered heterocyclic group which may have a substituent, N,N-dialkylcarbamoyloxyalkyl, N-alkylcarbamoylalkyl whose alkyl group may or may not be substituted, N,N-dialkylcarbamoylalkyl whose alkyl groups may or may not be substituted, alkylsulfonylamino, alkylsulfonylaminoalkyl, acyloxy, acyl, alkoxyalkyloxycarbonyl, halogenoacyl, N,N-dialkylaminoacyl, hydroxyacyl, alkoxyacyl, aminocarbothioyl, N-alkylaminocarbothioyl, N,N-dialkylaminocarbothioyl, and alkoxyalkyl(thiocarbonyl), among others.

Preferred examples of the substituent of $R^3$ or $R^4$ include a hydrogen atom, hydroxyl, methyl, ethyl, isopropyl, N,N-dimethylaminomethyl, N,N-dimethylaminoethyl, N,N-diethylaminomethyl, acetylamino, methoxyacetylamino, acetylaminomethyl, acetylaminoethyl, methoxy, ethoxy, methoxymethyl, methoxyethyl, hydroxymethyl, 2-hydroxyethyl, 1-hydroxy-1-methylethyl, methoxycarbonyl, ethoxycarbonyl, methoxycarbonylamino, ethoxycarbonylamino, N-allylcarbamoyl, N-allylcarbamoylmethyl, N-allyl-N-methylcarbamoyl, N-allyl-N-methylcarbamoylmethyl, N-methoxy-N-methylcarbamoyl, N,N-dimethylcarbazoyl, N,N,N'-trimethylcarbazoyl, methanesulfonyl, methanesulfonylmethyl, ethanesulfonylmethyl, N-methylcarbamoyl, N-ethylcarbamoyl, N-propylcarbamoyl, N-isopropylcarbamoyl, N-tert-butylcarbamoyl, N-cyclopropylcarbamoyl, N-cyclopropylmethylcarbamoyl, N-(1-ethoxycarbonylcyclopropyl)carbamoyl, N-(2-hydroxyethyl)carbamoyl, N-(2-fluoroethyl)carbamoyl, N-(2-methoxyethyl)carbamoyl, N-(carboxymethyl)carbamoyl, N-(2-aminoethyl)carbamoyl, N-(2-amidinoethyl)carbamoyl, N,N-dimethylcarbamoyl, N,N-diethylcarbamoyl, N-ethyl-N-methylcarbamoyl, N-isopropyl-N-methylcarbamoyl, N-methyl-N-propylcarbamoyl, N-(2-hydroxyethyl)-N-methylcarbamoyl, N-(2-fluoroethyl)-N-methylcarbamoyl, N,N-bis(2-hydroxyethyl)carbamoyl, N,N-bis(2-fluoroethyl)carbamoyl, N-(2-methoxyethyl)-N-methylcarbamoyl, N-carboxymethyl-N-methylcarbamoyl, N,N-bis(2-aminoethyl)carbamoyl, azetidinocarbonyl, 3-methoxyazetidinocarbonyl, 3-hydroxyazetidinocarbonyl, pyrrolidinocarbonyl, 3-hydroxypyrrolidinocarbonyl, 3-fluoropyrrolidinocarbonyl, 3,4-dimethoxypyrrolidinocarbonyl, piperidinocarbonyl, piperazinocatbonyl, morpholinocarbonyl, (tetrahydropyran-4-yl)carbonyl, benzoyl, pyridylcarbonyl, thiazolyl, 4,5-dihydrothiazolyl, oxazolyl, 4,5-dihydroxazolyl, 5-methyloxazolyl, imidazolyl, pyrrolidinyl, 3-hydroxypyrrolidinyl, piperidyl, piperazinyl, morpholinyl, thiomorpholinyl, 1,1-dioxothiomorpholinyl, tetrahydropyranyl, pyridyl, 1,2,4-oxadiazolyl, 3-methyl-1,2,4-oxadiazolyl, 5-methyl-1,2,4-oxadiazolyl, 1,3,4-oxadiazolyl, 5-methyl-1,3,4-oxadiazolyl, 5-(trifluoromethyl)-1,3,4-oxadiazolyl, 1,3-oxazolyl, 1,3,4-thiadiazolyl, 5-methyl-1,3,4-thiadiazolyl, 1,3-oxazolidinyl, N-methylcarbamoylmethyl, N-methylcarbamoylethyl, N-ethylcarbamoylmethyl, N-(2-fluoroethyl)carbamoylmethyl, N-(2-methoxyethyl)carbamoylmethyl, N,N-dimethylcarbamoylmethyl, N,N-dimethylcarbamoylethyl, N-(2-fluoroethyl)-N-methylcarbamoylmethyl, N-(2-methoxyethyl)-N-methylcarbamoylmethyl, N,N-dimethylcarbamoyloxymethyl, 2-(N-ethyl-N-methylcarbamoyloxy)ethyl, methylsulfonylamino, ethylsulfonylamino, methylsulfonylaminomethyl, methylsulfonylaminoethyl, acetyl, propionyl, isobutylyl, 2-methoxyethoxycarbonyl, trifluoroacetyl, N,N-dimethylaminoacetyl, N-ethyl-N-methylaminoacetyl, hydroxyacetyl, 1,1-dimethyl-2-hydroxyethylcarbonyl, methoxyacetyl, 1,1-dimethyl-2-methoxyethylcarbonyl, aminocarbothioyl, (dimethylamino)carbothioyl, and 2-methoxyethanethioyl.

As described above, preferred is the case in which $R^3$ represents a hydrogen atom, and $R^4$ is any of the groups listed above as specific examples or a similar group. In particular, N,N-dialkylcarbamoyl group which may have a substituent on the alkyl group thereof is preferred. Of these, N,N-dimethylcarbamoyl is preferred. However, $R^3$ and $R^4$ are not limited to the groups listed above as specific examples thereof.

<Group $T^1$>

$T^1$ represents carbonyl, sulfonyl, —C(=O)—C(=O)—N(R')—, —C(=S)—C(=O)—N(R')—, —C(=O)—C(=S)—N(R')—, —C(=S)—C(=S)—N(R')— (wherein R' represents a hydrogen atom, hydroxyl, alkyl, or alkoxy), —C(=O)-$A^1$-N(R")— (wherein $A^1$ represents a C1-C5 alkylene group which may have a substituent, R" represents a hydrogen atom, hydroxyl, alkyl, or alkoxy), —C(=O)—NH—, —C(=S)—NH—, —C(=O)—NH—NH—, —C(=O)-$A^2$-C(=O)— (wherein $A^2$ represents a single bond or a C1-C5 alkylene group), —C(=O)-$A^3$-C(=O)—NH— (wherein $A^3$ represents a C1-C5 alkylene), —C(=O)—C(=NOR$^a$)—N(R$^b$)—, —C(=S)—C(=NOR$^a$)—N(R$^b$)— (wherein R$^a$ represents a hydrogen atom, alkyl, or alkanoyl, R$^b$ represents a hydrogen atom, hydroxyl, alkyl, or alkoxy), —C(=O)—N=N—, —C(=S)—N=N—, —C(=NOR$^c$)—C(=O)—N(R$^d$)— (wherein R$^c$ represents a hydrogen atom, alkyl, alkanoyl, aryl, or aralkyl, R$^d$ represents a hydrogen atom, hydroxyl, alkyl, or alkoxy), —C(=N—N(R$^e$)(R$^f$))—C(=O)—N(R$^g$)— (wherein R$^e$ and R$^f$ each independently represents a hydrogen atom, alkyl, alkanoyl, or alkyl(thiocarbonyl), R$^g$ represents a hydrogen atom, hydroxyl, alkyl, or alkoxy), —C(=O)—NH—C(=O)—, —C(=S)—NH—C(=O)—, —C(=O)—NH—C(=S)—, —C(=S)—NHC(=S)—, —C(=O)—NH—SO$_2$—, —SO$_2$—NH—, —C(=NCN)—NH—C(=O)—, —C(=S)—C(=O)—, or thiocarbonyl.

In the above groups, the C1-C5 alkylene group in $A^1$, $A^2$, or $A^3$ is a C1-C5 linear, branched, or cyclic alkylene group, such as methylene, ethylene, propylene, cyclopropylene, or 1,3-cyclopentylene. In R', R", R$^a$, R$^b$, R$^c$, R$^d$, R$^e$, R$^f$, and R$^g$, the alkyl group is a C1-C6 linear, branched, or cyclic alkyl group, such as methyl or ethyl. The alkoxy group is a C1-C6 linear, branched, or cyclic alkoxy group, such as methoxy or ethoxy.

In R$^a$, R$^c$, R$^e$, and R$^f$, the alkanoyl group is a group composed of a linear, branched, or cyclic C1-C6 alkyl and a carbonyl group, such as acetyl or propionyl.

In R$^c$, the aryl group is a C6-C14 aryl group, such as phenyl or naphthyl. The aralkyl group is a group corresponding to a C1-C6 linear, branched, or cyclic alkyl group which has been substituted by a C6-C14 aryl group, such as benzyl or phenethyl.

$T^1$ is preferably carbonyl, —C(=O)—C(=O)—N(R')—, —C(=S)—C(=O)—N(R')—, —C(=O)—C(=S)—N(R')—, —C(=S)—C(=S)—N(R')—, or —C(=O)—CH$_2$—N(R")-, particularly preferably carbonyl, —C(=O)—C(=O)—N(R')—, —C(=S)—C(=O)—N(R')—, —C(=O)—C(=S)—N(R')—, or —C(=S)—C(=S)—N(R')—.

<Groups $R^1$ and $R^2$>

$R^1$ and $R^2$ each independently represent a hydrogen atom, hydroxyl, alkyl, or alkoxy, preferably a hydrogen atom or alkyl, more preferably a hydrogen atom.

In $R^1$ and $R^2$, the alkyl group is a C1-C6 linear, branched, or cyclic alkyl group, such as methyl or ethyl. The alkoxy group is a C1-C6 linear, branched, or cyclic alkoxy group, such as methoxy or ethoxy. The case where $R^1$ and $R^2$ each independently represent a hydrogen atom or an alkyl group is preferred, and the case where both are hydrogen atoms is more preferred.

When $T^1$ is a carbonyl group or a sulfonyl group, and $Q^1$ is a C1-C8 alkylene group or a C2-C8 alkenylene group, $Q^2$ is preferably, among the aforementioned 12 groups, any one of the groups (b), (f), (g), (h), (i), (j), (k), and (l) (wherein, in group (f), N denotes that two of the carbon atoms forming the ring substituted by $R^{19}$ are substituted by nitrogen atoms).

When $T^1$ is a carbonyl group or a sulfonyl group, and $Q^1$ is a C1-C8 alkylene group or a C2-C8 alkenylene group, the substituent(s) of the ring containing $Q^1$ is preferably N-alkylcarbamoyl or N,N-dialkylcarbamoyl.

When $T^1$ is —C(=O)—C(=O)—N(R')—, —C(=O)—C(=S)—N(R')—, or —C(=S)—C(=S)—N(R')—, and $Q^1$ is a C1-C8 alkylene group or a C2-C8 alkenylene group, $Q^2$ is preferably any one of the groups (i), (j), and (k), among the aforementioned 12 groups.

When $T^1$ is —C(=O)—C(=O)—N(R')—, —C(=S)—C(=O)—N(R')—, —C(=O)—C(=S)—N(R')—, or —C(=S)—C(=S)—N(R')—, and $Q^1$ is a C1-C8 alkylene group or a C2-C8 alkenylene group, the substituent of the ring containing $Q^1$ is preferably N-alkylcarbamoyl or N,N-dialkylcarbamoyl.

The feature of the compound represented by formula (8) resides in the combination of $T^1$ and $Q^2$. Generally, the compounds (8) is divided into the following two types (I) and (II):

(I) $T^1$ represents carbonyl, sulfonyl, —C(=O)—NH—C(=O)—, —C(=S)—NH—C(=O)—, —C(=O)—NH—C(=S)—, —C(=S)—NHC(=S)—, —C(=O)—NH—SO$_2$—, —SO$_2$—NH—, —C(=NCN)—NH—C(=O)—, —C(=S)—C(=O)—, or thiocarbonyl, and the group containing $Q^1$ is represented by the following formula:

[F71]

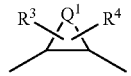

(wherein $Q^1$ represents —(CH$_2$)m-CH$_2$-A-CH$_2$—(CH$_2$)n- (wherein m and n are each independently 0 or an integer of 1 to 3, and A represents an oxygen atom, nitrogen atom, sulfur atom, —SO—, —SO$_2$—, —NH—, —O—NH—, —NH—NH—, —S—NH—, —SO—NH—, or SO$_2$—NH—); and (II) $T^1$ represents —C(=O)—C(=O)—N(R')—, —C(=S)—C(=O)—N(R')—, —C(=O)—C(=S)—N(R')—, —C(=S)—C(=S)—N(R')— (wherein R' represents a hydrogen atom, hydroxyl, alkyl, or alkoxy), —C(=O)-$A^1$-N(R")— (wherein $A^1$ represents a C1-C5 alkylene group which may have a substituent, R" represents a hydrogen atom, hydroxyl, alkyl, or alkoxy), —C(=O)—NH—, —C(=S)—NH—, —C(=O)—NH—NH—, —C(=O)-$A^2$-C(=O)— (wherein $A^2$ represents a single bond or a C1-C5 alkylene group), —C(=O)-$A^3$-C(=O)—NH— (wherein $A^3$ represents a C1-C5 alkylene), —C(=O)—C(=NOR$^a$)—N(R$^b$)—, —C(=S)—C(=NOR$^a$)—N(R$^b$)— (wherein R$^a$ represents a hydrogen atom, alkyl 又は a alkanoyl, R$^b$ represents a hydrogen atom, hydroxyl, alkyl, or alkoxy), —C(=O)—N=N—, —C(=S)—N=N—, —C(=NOR$^c$)—C(=O)—N(R$^d$)— (wherein R$^c$ represents a hydrogen atom, alkyl, alkanoyl, aryl, or aralkyl, R$^d$ represents a hydrogen atom, hydroxyl, alkyl, or alkoxy), —C(=N—N(R$^e$)(R$^f$))—C (=O)—N(R^g)— (wherein R^e and R^f each independently represents a hydrogen atom, alkyl, alkanoyl, or alkyl(thiocarbonyl), R^g represents a hydrogen atom, hydroxyl, alkyl, or alkoxy), —C(=O)—NH—C(=O)—, —C(=S)—NH—C(=O)—, —C(=O)—NH—C(=S)—, —C(=S)—NHC(=S)—, —C(=O)—NH—SO₂—, —SO₂—NH—, —C(=NCN)—NH—C(=O)—, —C(=S)—C(=O)—, or thiocarbonyl; and the group containing Q¹ is represented by the following formula:

[F72]

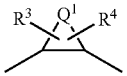

(wherein Q¹ represents a C1-C8 alkylene, C2-C8 alkenylene, or —(CH₂)m-CH₂-A-CH₂—(CH₂)n- (wherein m and n are each independently 0 or an integer of 1 to 3, and A represents an oxygen atom, nitrogen atom, sulfur atom, —SO—, —SO₂—, —NH—, —O—NH—, —NH—NH—, —S—NH—, —SO—NH—, or SO₂—NH—).

In the above (I) and (II), for example, the following (i) and (ii), respectively, are preferred:

(i) R¹ and R² each independently represents a hydrogen atom or an alkyl group, Q¹ represents —(CH₂)m-CH₂-A-CH₂—(CH₂)n- (wherein m and n are each independently 0 or 1, and A has the same meaning as described above), Q² is, among the aforementioned 12 groups, a group selected from the 9 groups (a) to (h), and (1), and T¹ represents a carbonyl group or a sulfonyl group; and (ii) R¹ and R² each independently represents a hydrogen atom or an alkyl group, Q¹ represents a C3-C6 alkylene group or —(CH₂)m-CH₂-A-CH₂—(CH₂)n- (wherein m and n are each independently 0 or 1, and A has the same meaning as described above), Q² is, among the aforementioned 12 groups, a group selected from the three groups (i), (j), and (k), and T¹ represents —C(=O)—C(=O)—N(R')—, —C(=S)—C(=O)—N(R')—, —C(=O)—C(=S)—N(R')—, or —C(=S)—C(=S)—N(R')—.

The compound represented by formula (8) may have corresponding stereochemical isomers and optical isomers based on asymmetric carbon atoms. The present invention encompasses any of the stereochemical isomers, the optical isomers and mixtures thereof.

No particular limitation is imposed on the salt of the compound represented by formula (8), so long as the salt is pharmaceutically acceptable. Examples of the salt include mineral acid salts such as hydrochloride, hydrobromide, hydroiodide, phosphate, nitrate, and sulfate, benzoate, organic sulfates such as methanesulfonate, 2-hydroxyethanesulfonate, and p-toluenesulfonate, and organic carboxylates such as acetate, propanoic acid salt, oxalate, malonate, succinate, glutarate, adipate, tartrate, maleate, malate, citrate, and mandelate.

When the compound represented by formula (8) has an acidic group, the compound may form a salt with an alkali metal ion or alkaline earth metal ion. The compound represented by formula (8) or a salt thereof may form a solvate. No particular limitation is imposed on the solvate, so long as the solvate is pharmaceutically acceptable, and examples of the solvate include hydrates and solvates with ethanol. When the compound represented by formula (8) includes a nitrogen atom, the compound may form an N-oxide.

The compound represented by formula (8) is particularly preferably any of the following compounds, a salt thereof, or similar compounds.

1) N-((1R*,2S*)-2-{[(5-chloroindol-2-yl)carbonyl]amino}cyclopropyl)-5-methyl-4,5,6,7-tetrahydrothiazolo[5,4-c]pyridine-2-carboxamide
2) N-((1R*,2S*)-2-{[(5-chloroindol-2-yl)carbonyl]amino}cyclobutyl)-5-methyl-4,5,6,7-tetrahydrothiazolo[5,4-c]pyridine-2-carboxamide
3) N-((1R*,2R*)-2-{[(5-chloroindol-2-yl)carbonyl]amino}cyclopentyl)-5-methyl-4,5,6,7-tetrahydrothiazolo[5,4-c]pyridine-2-carboxamide
4) N-((1R*,2S*)-2-{[(5-chloroindol-2-yl)sulfonyl]amino}cyclohexyl)-5-methyl-4,5,6,7-tetrahydrothiazolo[5,4-c]pyridine-2-carboxamide
5) N-((1R*,2R*)-2-{[(5-chloroindol-2-yl)carbonyl]amino}cyclohexyl)-5-methyl-4,5,6,7-tetrahydrothiazolo[5,4-c]pyridine-2-carboxamide
6) N-((1R*,2S*)-2-{[(5-chloroindol-2-yl)carbonyl]amino}cyclohexyl)-5-methyl-4,5,6,7-tetrahydrothiazolo[5,4-c]pyridine-2-carboxamide
7) N-{(1R*,2 S*)-2-[(6-chloro-2-naphthoyl)amino]cyclohexyl}-5-methyl-4,5,6,7-tetrahydrothiazolo[5,4-c]pyridine-2-carboxamide
8) N-((1R*,2R*)-2-{[(6-chloro-1-benzothiophen-2-yl)carbonyl]amino}cyclohexyl)-5-methyl-4,5,6,7-tetrahydrothiazolo[5,4-c]pyridine-2-carboxamide
9) N-((1R*,2R*)-2-{[(5-fluoroindol-2-yl)carbonyl]amino}cyclohexyl)-5-methyl-4,5,6,7-tetrahydrothiazolo[5,4-c]pyridine-2-carboxamide
10) N-((1R*,2R*)-2-{[(5-chloro-6-fluoroindol-2-yl)carbonyl]amino}cyclohexyl)-5-methyl-4,5,6,7-tetrahydrothiazolo[5,4-c]pyridine-2-carboxamide
11) N-((1R*,2S*)-2-{[(5-bromoindol-2-yl)carbonyl]amino}cyclohexyl)-5-methyl-4,5,6,7-tetrahydrothiazolo[5,4-c]pyridine-2-carboxamide
12) N-((1R*,2S*)-2-{[(5-ethynylindol-2-yl)carbonyl]amino}cyclohexyl)-5-methyl-4,5,6,7-tetrahydrothiazolo[5,4-c]pyridine-2-carboxamide
13) N-((1R*,2R*)-2-{[(5-chloroindol-2-yl)carbonyl]amino}cycloheptyl)-5-methyl-4,5,6,7-tetrahydrothiazolo[5,4-c]pyridine-2-carboxamide
14) N-((1R*,2S*)-2-{[(5-chloroindol-2-yl)carbonyl]amino}cyclooctyl)-5-methyl-4,5,6,7-tetrahydrothiazolo[5,4-c]pyridine-2-carboxamide
15) N-((1R*,2R*)-2-{[(5-chloroindol-2-yl)carbonyl]amino}-4-methoxycyclopentyl)-5-methyl-4,5,6,7-tetrahydrothiazolo[5,4-c]pyridine-2-carboxamide
16) 5-methyl-N-((1R*,2S*)-2-{[(5-methylindol-2-yl)carbonyl]amino}cyclohexyl)-4,5,6,7-tetrahydrothiazolo[5,4-c]pyridine-2-carboxamide
17) (1R*,3S*,4R*)-4-{[(5-chloroindol-2-yl)carbonyl]amino}-3-{[(5-methyl-4,5,6,7-tetrahydrothiazolo[5,4-c]pyridin-2-yl)carbonyl]amino}cyclohexanecarboxylic acid ethyl ester
18) (1S,3R,4S)-4-{[(5-chloroindol-2-yl)carbonyl]amino}-3-{[(5-methyl-4,5,6,7-tetrahydrothiazolo[5,4-c]pyridin-2-yl)carbonyl]amino}cyclohexanecarboxylic acid ethyl ester
19) (1R*,3R*,4S*)-3-{[(5-chloroindol-2-yl)carbonyl]amino}-4-{[(5-methyl-4,5,6,7-tetrahydrothiazolo[5,4-c]pyridin-2-yl)carbonyl]amino}cyclohexanecarboxylic acid methyl ester
20) (1R*,3S*,4R*)-3-{[(5-chloroindol-2-yl)carbonyl]amino}-4-{[(5-methyl-4,5,6,7-tetrahydrothiazolo[5,4-c]pyridin-2-yl)carbonyl]amino}cyclohexanecarboxylic acid ethyl ester 21) (1R*,3R*,4S*)-4-{[(5-chloroindol-2-yl)carbonyl]amino}-3-{[(5-methyl-4,5,6,7-tetrahydrothiazolo[5,4-c]pyridin-2-yl)carbonyl]amino}cyclohexanecarboxylic acid methyl ester 22) (1R,3R,4S)-4-{[(5-chloroindol-2-yl)carbonyl]amino}-3-{[(5-methyl-4,5,6,7-tetrahydrothiazolo[5,4-c]pyridin-2-yl)carbonyl]amino}cyclohexanecarboxylic acid methyl ester 23) N-((1R*,2 S*,5S*)-5-(aminocarbonyl)-2-{[(5-chloroindol-2-yl)carbonyl]amino}cyclohexyl)-5-methyl-4,5,6,7-tetrahydrothiazolo[5,4-c]pyridine-2-carboxamide 24) (1R*,3S*,4R*)-4-{[(5-chloroindol-2-yl)carbonyl]amino}-3-{[(5-methyl-4,5,6,7-tetrahydrothiazolo[5,4-c]pyridin-2-yl)carbonyl]amino}cyclohexanecarboxylic acid 25) N-{(1R*,2S*,5S*)-2-{[(5-chloroindol-2-yl)carbonyl]amino}-5-[(dimethylamino)carbonyl]cyclohexyl}-5-methyl-4,5,6,7-tetrahydrothiazolo[5,4-c]pyridine-2-carboxamide 26) (1S,3R,4S)-4-{[(5-chloroindol-2-yl)carbonyl]amino}-3-{[(5-methyl-4,5,6,7-tetrahydrothiazolo[5,4-c]pyridin-2-yl)carbonyl]amino}cyclohexanecarboxylic acid 27) N-{(1R,2S,5S)-2-{[(5-chloroindol-2-yl)carbonyl]amino}-5-[(cyclopropyl amino)carbonyl]cyclohexyl}-5-methyl-4,5,6,7-tetrahydrothiazolo[5,4-c]pyridine-2-carboxamide 28) N-[(1R,2S,5S)-2-{[(5-chloroindol-2-yl)carbonyl]amino}-5-(pyrrolidin-1-ylcarbonyl)cyclohexyl]-5-methyl-4,5,6,7-tetrahydrothiazolo[5,4-c]pyridine-2-carboxamide 29) N-[(1R*,2S*,5S*)-2-{[(5-chloroindol-2-yl)carbonyl]amino}-5-(4-morpholinylcarbonyl)cyclohexyl]-5-methyl-4,5,6,7-tetrahydrothiazolo[5,4-c]pyridine-2-carboxamide 30) N-{(1R,2 S,5S)-2-{[(5-chloroindol-2-yl)carbonyl]amino}-5-[(ethylamino)carbonyl]cyclohexyl}-5-methyl-4,5,6,7-tetrahydrothiazolo[5,4-c]pyridine-2-carboxamide 31) N-{(1R,2S,5S)-2-{[(5-chloroindol-2-yl)carbonyl]amino}-5-[(dimethylamino)carbonyl]cyclohexyl}-5-methyl-4,5,6,7-tetrahydrothiazolo[5,4-c]pyridine-2-carboxamide 32) N-((1R,2S,5S)-2-{[(5-chloroindol-2-yl)carbonyl]amino}-5-{[(2-methoxyethyl)(methyl)amino]carbonyl}cyclohexyl)-5-methyl-4,5,6,7-tetrahydrothiazolo[5,4-c]pyridine-2-carboxamide 33) N-((1R,2S,5S)-2-{[(5-chloroindol-2-yl)carbonyl]amino}-5-{[(2-hydroxyethyl)(methyl)amino]carbonyl}cyclohexyl)-5-methyl-4,5,6,7-tetrahydrothiazolo[5,4-c]pyridine-2-carboxamide 34) N-((1R,2S,5S)-5-(1-azetidinylcarbonyl)-2-{[(5-chloroindol-2-yl)carbonyl]amino}cyclohexyl)-5-methyl-4,5,6,7-tetrahydrothiazolo[5,4-c]pyridine-2-carboxamide 35) N-((1R,2S,5S)-2-{[(5-chloroindol-2-yl)carbonyl]amino}-5-{[(3S)-3-fluoropyrrolidinyl]carbonyl}cyclohexyl)-5-methyl-4,5,6,7-tetrahydrothiazolo[5,4-c]pyridine-2-carboxamide 36) (1R*,3R*,4S*)-3-{[(5-chloroindol-2-yl)carbonyl]amino}-4-{[(5-methyl-4,5,6,7-tetrahydrothiazolo[5,4-c]pyridin-2-yl)carbonyl]amino}cyclohexanecarboxylic acid 37) N-{(1R*,2S*,4S*)-2-{[(5-chloroindol-2-yl)carbonyl]amino}-4-[(dimethylamino)carbonyl]cyclohexyl}-5-methyl-4,5,6,7-tetrahydrothiazolo[5,4-c]pyridine-2-carboxamide 38) N-((1R,2S,5S)-2-{[(5-chloroindol-2-yl)carbonyl]amino}-5-{[(3R)-3-hydroxypyrrolidinyl]carbonyl}cyclohexyl)-5-methyl-4,5,6,7-tetrahydrothiazolo[5,4-c]pyridine-2-carboxamide 39) N-((1R*,2S*)-2-{[(5-chloroindol-2-yl)carbonyl]amino}-5,5-dimethoxycyclohexyl)-5-methyl-4,5,6,7-tetrahydrothiazolo[5,4-c]pyridine-2-carboxamide, N-((1R*,2S*)-2-{[(5-chloroindol-2-yl)carbonyl]amino}-4,4-dimethoxycyclohexyl)-5-methyl-4,5,6,7-tetrahydrothiazolo[5,4-c]pyridine-2-carboxamide 40) N-((1R*,2S*)-2-{[(5-chloroindol-2-yl)carbonyl]amino}-5-oxocyclohexyl)-5-methyl-4,5,6,7-tetrahydrothiazolo[5,4-c]pyridine-2-carboxamide, N-((1R*,2S*)-2-{[(5-chloroindol-2-yl)carbonyl]amino}-4-oxocyclohexyl)-5-methyl-4,5,6,7-tetrahydrothiazolo[5,4-c]pyridine-2-carboxamide 41) N-[(1R*,2S*)-2-{[(5-chloroindol-2-yl)carbonyl]amino}-5-(hydroxyimino)cyclohexyl]-5-methyl-4,5,6,7-tetrahydrothiazolo[5,4-c]pyridine-2-carboxamide, N-[(1R*,2S*)-2-{[(5-chloroindol-2-yl)carbonyl]amino}-4-(hydroxyimino)cyclohexyl]-5-methyl-4,5,6,7-tetrahydrothiazolo[5,4-c]pyridine-2-carboxamide 42) N-((7R*,8S*)-8-{[(5-chloroindol-2-yl)carbonyl]amino}-1,4-dioxaspiro[4.5]dec-7-yl)-5-methyl-4,5,6,7-tetrahydrothiazolo[5,4-c]pyridine-2-carboxamide, N-((7R*,8S*)-7-{[(5-chloroindol-2-yl)carbonyl]amino}-1,4-dioxaspiro[4.5]dec-8-yl)-5-methyl-4,5,6,7-tetrahydrothiazolo[5,4-c]pyridine-2-carboxamide 43) N-[(1R*,2S*)-2-{[(5-chloroindol-2-yl)carbonyl]amino}-5-(methoxyimino)cyclohexyl]-5-methyl-4,5,6,7-tetrahydrothiazolo[5,4-c]pyridine-2-carboxamide, N-[(1R*,2S*)-2-{[(5-chloroindol-2-yl)carbonyl]amino}-4-(methoxyimino)cyclohexyl]-5-methyl-4,5,6,7-tetrahydrothiazolo[5,4-c]pyridine-2-carboxamide 44) N-((1R*,2S*)-2-{[(5-chloroindol-2-yl)carbonyl]amino}-5-hydroxycyclohexyl)-5-methyl-4,5,6,7-tetrahydrothiazolo[5,4-c]pyridine-2-carboxamide, N-((1R*,2S*)-2-{[5-chloroindol-2-yl)carbonyl]amino}-4-hydroxycyclohexyl)-5-methyl-4,5,6,7-tetrahydrothiazolo[5,4-c]pyridine-2-carboxamide 45) N-((1R*,2S*)-2-{[(5-chloroindol-2-yl)carbonyl]amino}-5-hydroxy-5-methylcyclohexyl)-5-methyl-4,5,6,7-tetrahydrothiazolo[5,4-c]pyridine-2-carboxamide, N-((1R*,2S*)-2-{[(5-chloroindol-2-yl)carbonyl]amino}-4-hydroxy-4-methylcyclohexyl)-5-methyl-4,5,6,7-tetrahydrothiazolo[5,4-c]pyridine-2-carboxamide 46) N-[(1R*,2R*,5S*)-2-{[(5-chloroindol-2-yl)carbonyl]amino}-5-(hydroxymethyl)cyclohexyl]-5-methyl-4,5,6,7-tetrahydrothiazolo[5,4-c]pyridine-2-carboxamide 47) N-[(1R*,2S*,5S*)-2-{[(5-chloroindol-2-yl)carbonyl]amino}-5-(methoxymethyl)cyclohexyl]-5-methyl-4,5,6,7-tetrahydrothiazolo[5,4-c]pyridine-2-carboxamide 48) N-((1R*,2S*,5S*)-2-{[(5-chloroindol-2-yl)carbonyl]amino}-5-{[(methylsulfonyl)amino]methyl}cyclohexyl)-5-methyl-4,5,6,7-tetrahydrothiazolo[5,4-c]pyridine-2-carboxamide 49) N-{(1R*,2S*,5S*)-2-{[(5-chloroindol-2-yl)carbonyl]amino}-5-[(dimethylamino)methyl]cyclohexyl}-5-methyl-4,5,6,7-tetrahydrothiazolo[5,4-c]pyridine-2-carboxamide 50) (3R*,4S*)-4-{[(5-chloroindol-2-yl)carbonyl]amino}-3-{[(5-methyl-4,5,6,7-tetrahydrothiazolo[5,4-c]pyridin-2-yl)carbonyl]amino}cyclohexylcarbamic acid tert-butyl ester, (3R*,4S*)-3-{[(5-chloroindol-2-yl)carbonyl]amino}-4-{[(5-methyl-4,5,6,7-tetrahydrothiazolo[5,4-c]pyridin-2-yl)carbonyl]amino}cyclohexylcarbamic acid tert-butyl ester 51) N-((1R*,2S*)-5-amino-2-{[(5-chloroindol-2-yl)carbonyl]amino}cyclohexyl)-5-methyl-4,5,6,7-tetrahydrothiazolo[5,4-c]pyridine-2-carboxamide, N-((1R*,2S*)-4-amino-2-{[(5-chloroindol-2-yl)carbonyl]

amino}cyclohexyl)-5-methyl-4,5,6,7-tetrahydrothiazolo[5,4-c]pyridine-2-carboxamide 52) N-[(1R*,2S*)-2-{[(5-chloroindol-2-yl)carbonyl]amino}-5-[(methylsulfonyl)amino]cyclohexyl]-5-methyl-4,5,6,7-tetrahydrothiazolo[5,4-c]pyridine-2-carboxamide, N-[(1R*,2S*)-2-{[(5-chloroindol-2-yl)carbonyl]amino}-4-[(methylsulfonyl)amino]cyclohexyl]-5-methyl-4,5,6,7-tetrahydrothiazolo[5,4-c]pyridine-2-carboxamide 53) N-((1R*,2)-5-(acetylamino)-2-{[(5-chloro indol-2-yl)carbonyl]amino}cyclohexyl)-5-methyl-4,5,6,7-tetrahydrothiazolo[5,4-c]pyridine-2-carboxamide, N-((1R*,2S*)-4-(acetylamino)-2-{[(5-chloroindol-2-yl)carbonyl]amino}cyclohexyl)-5-methyl-4,5,6,7-tetrahydrothiazolo[5,4-c]pyridine-2-carboxamide 54) N-((1R,2S,5S)-2-{-[(5-chloroindol-2-yl)carbonyl]amino}-5-{[methoxy(methyl)amino]carbonyl}cyclohexyl)-5-methyl-4,5,6,7-tetrahydrothiazolo[5,4-c]pyridine-2-carboxamide 55) N-{(1R,2S,5S)-2-{[(5-chloroindol-2-yl)carbonyl]amino}-5-[(2,2-dimethylhydrazino)carbonyl]cyclohexyl}-5-methyl-4,5,6,7-tetrahydrothiazolo[5,4-c]pyridine-2-carboxamide 56) 6-chloro-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-2-quinolinecarboxamide 57) N-{(1R,2S,5S)-2-{[(5-chloro-4-fluoroindol-2-yl)carbonyl]amino}-5-[(dimethylamino)carbonyl]cyclohexyl}-5-methyl-4,5,6,7-tetrahydrothiazolo[5,4-c]pyridine-2-carboxamide 58) 7-chloro-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)isoquinoline-3-carboxamide 59) N-((3R*,4 S*)-4-{[(5-chloroindol-2-yl)carbonyl]amino}tetrahydrofuran-3-yl)-5-methyl-4,5,6,7-tetrahydrothiazolo[5,4-c]pyridine-2-carboxamide 60) N-((3S,4S)-4-{[(5-chloroindol-2-yl)carbonyl]amino}tetrahydrofuran-3-yl)-5-methyl-4,5,6,7-tetrahydrothiazolo[5,4-c]pyridine-2-carboxamide 61) N-((3R,4R)-4-{[(5-chloroindol-2-yl)carbonyl]amino}tetrahydrofuran-3-yl)-5-methyl-4,5,6,7-tetrahydrothiazolo[5,4-c]pyridine-2-carboxamide 62) (3R,4R)-3-{[(5-chloroindol-2-yl)carbonyl]amino}-4-{[(5-methyl-4,5,6,7-tetrahydrothiazolo[5,4-c]pyridin-2-yl)carbonyl]amino}pyrrolidine-1-carboxylic acid tert-butyl ester 63) N-((3R,4R)-4-{[(5-chloroindol-2-yl)carbonyl]amino}pyrrolidin-3-yl)-5-methyl-4,5,6,7-tetrahydrothiazolo[5,4-c]pyridine-2-carboxamide 64) N-((3S,4S)-4-{[(5-chloroindol-2-yl)carbonyl]amino}-5-oxotetrahydrofuran-3-yl)-5-methyl-4,5,6,7-tetrahydrothiazolo[5,4-c]pyridine-2-carboxamide 65) N-((3S,4S)-4-{[(5-chloroindol-2-yl)carbonyl]amino}-2-oxotetrahydrofuran-3-yl)-5-methyl-4,5,6,7-tetrahydrothiazolo[5,4-c]pyridine-2-carboxamide 66) (3S,4R)-2-(3-{[(5-chloroindol-2-yl)carbonyl]amino}-4-{[(5-methyl-4,5,6,7-tetrahydrothiazolo[5,4-c]pyridin-2-yl)carbonyl]amino}-2-oxopyrrolidin-1-yl)acetic acid ethyl ester 67) N-((3R,4S)-4-{[(5-chloroindol-2-yl)carbonyl]amino}-1-methyl-5-oxopyrrolidin-3-yl)-5-methyl-4,5,6,7-tetrahydrothiazolo[5,4-c]pyridine-2-carboxamide 68) 2-[((3R,4R)-3-{[(5-chloroindol-2-yl)carbonyl]amino}-4-{[(5-methyl-4,5,6,7-tetrahydrothiazolo[5,4-c]pyridin-2-yl)carbonyl]amino}pyrrolidin-1-yl)sulfonyl]acetic acid methyl ester 69) 2-[((3R,4R)-3-{[(5-chloroindol-2-yl)carbonyl]amino}-4-{[(5-methyl-4,5,6,7-tetrahydrothiazolo[5,4-c]pyridin-2-yl)carbonyl]amino}pyrrolidin-1-yl)sulfonyl]acetic acid 70) 2-((3R,4R)-3-{[(5-chloroindol-2-yl)carbonyl]amino}-4-{[(5-methyl-4,5,6,7-tetrahydrothiazolo[5,4-c]pyridin-2-yl)carbonyl]amino}pyrrolidin-1-yl)acetic acid methyl ester 71) 2-((3R,4R)-3-{[(5-chloroindol-2-yl)carbonyl]amino}-4-{[(5-methyl-4,5,6,7-tetrahydrothiazolo[5,4-c]pyridin-2-yl)carbonyl]amino}pyrrolidin-1-yl)acetic acid 72) 3-((3R,4R)-3-{[(5-chloroindol-2-yl)carbonyl]amino}-4-{[(5-methyl-4,5,6,7-tetrahydrothiazolo[5,4-c]pyridin-2-yl)carbonyl]amino}pyrrolidin-1-yl)propionic acid methyl ester 73) 3-03R,4R)-3-{[(5-chloroindol-2-yl)carbonyl]amino}-4-{[(5-methyl-4,5,6,7-tetrahydrothiazolo[5,4-c]pyridin-2-yl)carbonyl]amino}pyrrolidin-1-yl)propionic acid 74) 3-03R,4R)-3-{[(5-chloroindol-2-yl)carbonyl]amino}-4-{[(5-methyl-4,5,6,7-tetrahydrothiazolo[5,4-c]pyridin-2-yl)carbonyl]amino}pyrrolidin-1-yl)-3-oxopropionic acid ethyl ester 75) 343R,4R)-3-{[(5-chloroindol-2-yl)carbonyl]amino}-4-{[(5-methyl-4,5,6,7-tetrahydrothiazolo[5,4-c]pyridin-2-yl)carbonyl]amino}pyrrolidin-1-yl)-3-oxopropionic acid 76) 1-[((3R,4R)-3-{[(5-chloroindol-2-yl)carbonyl]amino}-4-{[(5-methyl-4,5,6,7-tetrahydrothiazolo[5,4-c]pyridin-2-yl)carbonyl]amino}pyrrolidin-1-yl)methyl]cyclopropanecarboxylic acid methyl ester 77) 1-[((3R,4R)-3-{[(5-chloroindol-2-yl)carbonyl]amino}-4-{[(5-methyl-4,5,6,7-tetrahydrothiazolo[5,4-c]pyridin-2-yl)carbonyl]amino}pyrrolidin-1-yl)methyl]cyclopropanecarboxylic acid 78) (3R,4S*)-4-{[(5-chloroindol-2-yl)carbonyl]amino}-3-{[(5-methyl-4,5,6,7-tetrahydrothiazolo[5,4-c]pyridin-2-yl)carbonyl]amino}piperidine-1-carboxylic acid tert-butyl ester 79) N-((3R*,4S*)-4-{[(5-chloroindol-2-yl)carbonyl]amino}piperidin-3-yl)-5-methyl-4,5,6,7-tetrahydrothiazolo[5,4-c]pyridine-2-carboxamide 80) (3R*,4S*)-3-{[(5-chloroindol-2-yl)carbonyl]amino}-4-{[(5-methyl-4,5,6,7-tetrahydrothiazolo[5,4-c]pyridin-2-yl)carbonyl]amino}piperidine-1-carboxylic acid tert-butyl ester 81) N-((3R*,4S*)-3-{[(5-chloroindol-2-yl)carbonyl]amino}piperidin-4-yl)-5-methyl-4,5,6,7-tetrahydrothiazolo[5,4-c]pyridine-2-carboxamide 82) (3R*,4S*)-4-{[(5-fluoroindol-2-yl)carbonyl]amino}-3-{[(5-methyl-4,5,6,7-tetrahydrothiazolo[5,4-c]pyridin-2-yl)carbonyl]amino}piperidine-1-carboxylic acid tert-butyl ester 83) N-((3R*,4S*)-4-{[(5-fluoroindol-2-yl)carbonyl]amino}piperidin-3-yl)-5-methyl-4,5,6,7-tetrahydrothiazolo[5,4-c]pyridine-2-carboxamide 84) N-((3R*,4 S*)-1-acetyl-4-{[(5-chloroindol-2-yl)carbonyl]amino}piperidin-3-yl)-5-methyl-4,5,6,7-tetrahydrothiazolo[5,4-c]pyridine-2-carboxamide 85) N-((3R*,4 S*)-1-acetyl-3-{[(5-chloroindol-2-yl)carbonyl]amino}piperidin-4-yl)-5-methyl-4,5,6,7-tetrahydrothiazolo[5,4-c]pyridine-2-carboxamide 86) N-((3R*,4S*)-1-acetyl-4-{[(5-fluoroindol-2-yl)carbonyl]amino}piperidin-3-yl)-5-methyl-4,5,6,7-tetrahydrothiazolo[5,4-c]pyridine-2-carboxamide 87) N-[(3R*,4S*)-4-{[(5-chloroindol-2-yl)carbonyl]amino}-1-(methylsulfonyl)piperidin-3-yl]-5-methyl-4,5,6,7-tetrahydrothiazolo[5,4-c]pyridine-2-carboxamide
88) N-[(3R*,4S*)-3-{[(5-chloroindol-2-yl)carbonyl]amino}-1-(methylsulfonyl)piperidin-4-yl]-5-methyl-4,5,6,7-tetrahydrothiazolo[5,4-c]pyridine-2-carboxamide
89) N-[(3R*,4S*)-4-{[(5-fluoroindol-2-yl)carbonyl]amino}-1-(methylsulfonyl)piperazin-3-yl]-5-methyl-4,5,6,7-tetrahydrothiazolo[5,4-c]pyridine-2-carboxamide
90) (3R*,4S*)-4-{[(5-chloroindol-2-yl)carbonyl]amino}-3-{[(5-methyl-4,5,6,7-tetrahydrothiazolo[5,4-c]pyridin-2-yl)carbonyl]amino}piperidine-1-carboxylic acid methyl ester
91) (3R*,4S*)-4-{[(5-chloroindol-2-yl)carbonyl]amino}-3-{[(5-methyl-4,5,6,7-tetrahydrothiazolo[5,4-c]pyridin-2-yl)carbonyl]amino}piperidine-1-carboxylic acid ethyl ester
92) (3R*,4S*)-4-{[(5-chloroindol-2-yl)carbonyl]amino}-3-{[(5-methyl-4,5,6,7-tetrahydrothiazolo[5,4-c]pyridin-2-yl)carbonyl]amino}piperidine-1-carboxylic acid 2-methoxyethyl ester
93) (3R*,4S*)-3-{[(5-chloroindol-2-yl)carbonyl]amino}-4-{[(5-methyl-4,5,6,7-tetrahydrothiazolo[5,4-c]pyridin-2-yl)carbonyl]amino}piperidine-1-carboxylic acid ethyl ester
94) N-((3R*,4S*)-4-{[(5-chloroindol-2-yl)carbonyl]amino}-1-propionylpiperidin-3-yl)-5-methyl-4,5,6,7-tetrahydrothiazolo[5,4-c]pyridine-2-carboxamide
95) N-((3R*,4S*)-4-{[(5-chloroindol-2-yl)carbonyl]amino}-1-isobutylylpiperidin-3-yl)-5-methyl-4,5,6,7-tetrahydrothiazolo[5,4-c]pyridine-2-carboxamide
96) N-[(3R*,4S*)-4-{[(5-chloroindol-2-yl)carbonyl]amino}-1-(2,2-dimethylpropanoyl)piperidin-3-yl]-5-methyl-4,5,6,7-tetrahydrothiazolo[5,4-c]pyridine-2-carboxamide
97) N-[(3R*,4S*)-4-{[(5-chloroindol-2-yl)carbonyl]amino}-1-(3,3-dimethylbutanoyl)piperidin-3-yl]-5-methyl-4,5,6,7-tetrahydrothiazolo[5,4-c]pyridine-2-carboxamide
98) N-[(3R*,4S*)-4-{[(5-chloroindol-2-yl)carbonyl]amino}-(2,2,2-trifluoroacetyl)piperidin-3-yl]-5-methyl-4,5,6,7-tetrahydrothiazolo[5,4-c]pyridine-2-carboxamide
99) N-[(3R*,4S*)-4-{[(5-chloroindol-2-yl)carbonyl]amino}-1-(cyclopropylcarbonyl)piperidin-3-yl]-5-methyl-4,5,6,7-tetrahydrothiazolo[5,4-c]pyridine-2-carboxamide
100) N-[(3R*,4S*)-4-{[(5-chloroindol-2-yl)carbonyl]amino}-1-(cyclobutylcarbonyl)piperidin-3-yl]-5-methyl-4,5,6,7-tetrahydrothiazolo[5,4-c]pyridine-2-carboxamide
101) N-[(3R*,4S*)-4-{[(5-chloroindol-2-yl)carbonyl]amino}-1-(cyclopentylcarbonyl)piperidin-3-yl]-5-methyl-4,5,6,7-tetrahydrothiazolo[5,4-c]pyridine-2-carboxamide
102) 2-((3R*,4S*)-4-{[(5-chloroindol-2-yl)carbonyl]amino}-3-{[(5-methyl-4,5,6,7-tetrahydrothiazolo[5,4-c]pyridin-2-yl)carbonyl]amino}piperidin-1-yl)-2-oxoethyl acetate
103) N-(((3R*,4S*)-4-{[(5-chloroindol-2-yl)carbonyl]amino}-1-glycoloylpiperidin-3-yl)-5-methyl-4,5,6,7-tetrahydrothiazolo[5,4-c]pyridine-2-carboxamide
104) N-[(3R*,4S*)-4-{[(5-chloroindol-2-yl)carbonyl]amino}-1-(2-methoxyacetyl)piperidin-3-yl]-5-methyl-4,5,6,7-tetrahydrothiazolo[5,4-c]pyridine-2-carboxamide
105) N-[(3R*,4S*)-4-{[(5-fluoroindol-2-yl)carbonyl]amino}-1-(2-methoxyacetyl)piperidin-3-yl]-5-methyl-4,5,6,7-tetrahydrothiazolo[5,4-c]pyridine-2-carboxamide
106) N-((3R*,4S*)-1-(3-{[tert-butyl(diphenyl)silyl]oxy}-2,2-dimethylpropanoyl)-4-{[(5-chloroindol-2-yl)carbonyl]amino}piperidin-3-yl)-5-methyl-4,5,6,7-tetrahydrothiazolo[5,4-c]pyridine-2-carboxamide
107) N-[(3R*,4S*)-4-{[(5-chloroindol-2-yl)carbonyl]amino}-1-(3-hydroxy-2,2-dimethylpropanoyl)piperidin-3-yl]-5-methyl-4,5,6,7-tetrahydrothiazolo[5,4-c]pyridine-2-carboxamide
108) N-[(3R*,4S*)-4-{[(5-chloroindol-2-yl)carbonyl]amino}-1-(3-methoxy-2,2-dimethylpropanoyl)piperidin-3-yl]-5-methyl-4,5,6,7-tetrahydrothiazolo[5,4-c]pyridine-2-carboxamide
109) 2-((3R*,4S*)-4-{[(5-chloroindol-2-yl)carbonyl]amino}-3-{[(5-methyl-4,5,6,7-tetrahydrothiazolo[5,4-c]pyridin-2-yl)carbonyl]amino}piperidin-1-yl)-1,1-dimethyl-2-oxo ethyl acetate
110) N-[(3R*,4S*)-4-{[(5-chloroindol-2-yl)carbonyl]amino}-1-(2-hydroxy-2-methylpropanoyl)piperidin-3-yl]-5-methyl-4,5,6,7-tetrahydrothiazolo[5,4-c]pyridine-2-carboxamide
111) N-{(3R*,4S*)-4-{[(5-chloroindol-2-yl)carbonyl]amino}-1-[(3-hydroxycyclobutyl)carbonyl]piperidin-3-yl}-5-methyl-4,5,6,7-tetrahydrothiazolo[5,4-c]pyridine-2-carboxamide
112) N-{(3R*,4S*)-4-{[(5-chloroindol-2-yl)carbonyl]amino}-1-[(methoxycyclobutyl)carbonyl]piperidin-3-yl}-5-methyl-4,5,6,7-tetrahydrothiazolo[5,4-c]pyridine-2-carboxamide
113) N-{(3R*,4S*)-4-{[(5-chloroindol-2-yl)carbonyl]amino}-1-[3-methoxy-2-(methoxymethyl)propanoyl]piperidin-3-yl}-5-methyl-4,5,6,7-tetrahydrothiazolo[5,4-c]pyridine-2-carboxamide
114) N-[(3R*,4S*)-4-{[(5-chloroindol-2-yl)carbonyl]amino}-1-(tetrahydro-2H-pyran-4-ylcarbonyl)piperidin-3-yl]-5-methyl-4,5,6,7-tetrahydrothiazolo[5,4-c]pyridine-2-carboxamide
115) N-((3R*,4S*)-1-benzoyl-4-{[(5-chloroindol-2-yl)carbonyl]amino}piperidin-3-yl)-5-methyl-4,5,6,7-tetrahydrothiazolo[5,4-c]pyridine-2-carboxamide
116) N-{(3R*,4S*)-4-{[(5-chloroindol-2-yl)carbonyl]amino}-1-[(dimethylamino)carbonyl]piperidin-3-yl}-5-methyl-4,5,6,7-tetrahydrothiazolo[5,4-c]pyridine-2-carboxamide
117) N-{(3R*,4S*)-4-{[(5-chloroindol-2-yl)carbonyl]amino}-1-[(ethylamino)carbonyl]piperidin-3-yl}-5-methyl-4,5,6,7-tetrahydrothiazolo[5,4-c]pyridine-2-carboxamide
118) N-((3R*,4S*)-1-[(tert-butylamino)carbonyl]-4-{[(5-chloroindol-2-yl)carbonyl]amino}piperidin-3-yl)-5-methyl-4,5,6,7-tetrahydrothiazolo[5,4-c]pyridine-2-carboxamide
119) 2-((3R*,4S*)-4-{[(5-chloroindol-2-yl)carbonyl]amino}-3-{[(5-methyl-4,5,6,7-tetrahydrothiazolo[5,4-c]pyridin-2-yl)carbonyl]amino}piperidin-3-yl)acetic acid methyl ester
120) 2-((3R*,4S*)-4-{[(5-chloroindol-2-yl)carbonyl]amino}-3-{[(5-methyl-4,5,6,7-tetrahydrothiazolo[5,4-c]pyridin-2-yl)carbonyl]amino}piperidin-3-yl)acetic acid
121) N-[(3R*,4S*)-4-{[(5-chloroindol-2-yl)carbonyl]amino}-1-(2-methoxyethyl)piperidin-3-yl]-5-methyl-4,5,6,7-tetrahydrothiazolo[5,4-c]pyridine-2-carboxamide
122) N-[(3R*,4S*)-4-{[(5-chloroindol-2-yl)carbonyl]amino}-1-(2-fluoroethyl)piperidin-3-yl]-5-methyl-4,5,6,7-tetrahydrothiazolo[5,4-c]pyridine-2-carboxamide
123) N-((3R,4S)-1-acetyl-4-{[(5-chloroindol-2-yl)carbonyl]amino}piperidin-3-yl)-5-methyl-4,5,6,7-tetrahydrothiazolo[5,4-c]pyridine-2-carboxamide 124) N-((3R,4R)-1-acetyl-4-{[(5-chloroindol-2-yl)carbonyl]amino}piperidin-3-yl)-5-methyl-4,5,6,7-tetrahydrothiazolo[5,4-c]pyridine-2-carboxamide 125) N-[(3R,4S)-4-{[(5-chloroindol-2-yl)carbonyl]amino}-1-(2-methoxyacetyl)piperidin-3-yl]-5-methyl-4,5,6,7-tetrahydrothiazolo[5,4-c]pyridine-2-carboxamide 126) N-[(3R,4R)-4-{[(5-chloroindol-2-yl)carbonyl]amino}-1-(2-methoxyacetyl)piperidin-3-yl]-5-methyl-4,5,6,7-tetrahydrothiazolo[5,4-c]pyridine-2-carboxamide 127) N-((3R,4R)-4-{[(5-chloroindol-2-yl)carbonyl]amino}-6-oxotetrahydro-2H-pyran-3-yl)-5-methyl-4,5,6,7-tetrahydrothiazolo[5,4-c]pyridine-2-carboxamide 128) N-((3R,4S)-4-{[(5-chloroindol-2-yl)carbonyl]amino}-6-oxotetrahydro-2H-pyran-3-yl)-5-methyl-4,5,6,7-tetrahydrothiazolo[5,4-c]pyridine-2-carboxamide 129) (3R,4S)-5-{[tert-butyl(diphenyl)silyl]oxy}-3-{[(5-chloroindol-2-yl)carbonyl]amino}-4-{[(5-methyl-4,5,6,7-tetrahydrothiazolo[5,4-c]pyridin-2-yl)carbonyl]amino}valeric acid ethyl ester 130) (3R,4S)-3-{[(5-chloroindol-2-yl)carbonyl]amino}-5-hydroxy-4-{[(5-methyl-4,5,6,7-tetrahydrothiazolo[5,4-c]pyridin-2-yl)carbonyl]amino}valeric acid ethyl ester 131) N-((3S,4R)-4-{[(5-chloroindol-2-yl)carbonyl]amino}-6-oxotetrahydro-2H-pyran-3-yl)-5-methyl-4,5,6,7-tetrahydrothiazolo[5,4-c]pyridine-2-carboxamide 132) N-((3R*,4R*)-4-{[(5-chloroindol-2-yl)carbonyl]amino}-1,1-dioxohexahydro-1-thiopyran-3-yl)-5-methyl-4,5,6,7-tetrahydrothiazolo[5,4-c]pyridine-2-carboxamide 133) N-((3R*,4R*)-4-{[(5-fluoroindol-2-yl)carbonyl]amino}-1,1-dioxohexahydro-1-thiopyran-3-yl)-5-methyl-4,5,6,7-tetrahydrothiazolo[5,4-c]pyridine-2-carboxamide 134) N-((3R*,4R*)-3-{[(5-chloroindol-2-yl)carbonyl]amino}-1,1-dioxohexahydro-1-thiopyran-4-yl)-5-methyl-4,5,6,7-tetrahydrothiazolo[5,4-c]pyridine-2-carboxamide 135) N-((3R*,4S*)-4-{[(5-chloroindol-2-yl)carbonyl]amino}-1,1-dioxohexahydro-1-thiopyran-3-yl)-5-methyl-4,5,6,7-tetrahydrothiazolo[5,4-c]pyridine-2-carboxamide 136) N-((3R*,4S*)-4-{[(5-fluoroindol-2-yl)carbonyl]amino}-1,1-dioxohexahydro-1-thiopyran-3-yl)-5-methyl-4,5,6,7-tetrahydrothiazolo[5,4-c]pyridine-2-carboxamide 137) N-((3R*,4R*)-3-{[(5-fluoroindol-2-yl)carbonyl]amino}-1,1-dioxohexahydro-1-thiopyran-4-yl)-5-methyl-4,5,6,7-tetrahydrothiazolo[5,4-c]pyridine-2-carboxamide 138) N-((3S,4R)-4-{[(5-chloroindol-2-yl)carbonyl]amino}-1-methyl-6-oxopiperidin-3-yl)-5-methyl-4,5,6,7-tetrahydrothiazolo[5,4-c]pyridine-2-carboxamide, N-((3R,4R)-4-{[(5-chloroindol-2-yl)carbonyl]amino}-1-methyl-6-oxopiperidin-3-yl)-5-methyl-4,5,6,7-tetrahydrothiazolo[5,4-c]pyridine-2-carboxamide 139) $N^1$-(4-chlorophenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide 140) $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide 141) $N^1$-(3-chlorophenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide 142) $N^1$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-$N^2$-(4-fluorophenyl)ethanediamide 143) $N^1$-(4-bromophenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide 144) $N^1$-(4-chloro-2-methylphenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide 145) $N^1$-(4-chloro-3-methylphenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide 146) $N^1$-(4-chloro-2-fluorophenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide 147) $N^1$-(2,4-dichlorophenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide 148) $N^1$-(3,4-dichlorophenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide 149) $N^1$-(2,4-difluorophenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide 150) $N^1$-(3,4-difluorophenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide 151) $N^1$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-$N^2$-(pyridin-4-yl)ethanediamide 152) $N^1$-(5-bromopyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide 153) $N^1$-(6-chloropyridin-3-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide 154) $N^1$-(6-chloropyridazin-3-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide 155) $N^1$-(5-chlorothiazol-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide 156) N-{(1R,2S,5S)-2-{[2-(4-chloroanilino)acetyl]amino}-5-[(dimethylamino)carbonyl]cyclohexyl}-5-methyl-4,5,6,7-tetrahydrothiazolo[5,4-c]pyridine-2-carboxamide 157) N-{(1R,2S,5S)-2-{[2-(4-chloro-2-fluoroanilino)acetyl]amino}-5-[(dimethylamino)carbonyl]cyclohexyl}-5-methyl-4,5,6,7-tetrahydrothiazolo[5,4-c]pyridine-2-carboxamide 158) N-{(1R,2S,5S)-2-{[(5-chloro-4-fluoroindol-2-yl)carbonyl]amino}-5-[(dimethylamino)carbonyl]cyclohexyl}-5-methyl-4,5,6,7-tetrahydrothiazolo[5,4-c]pyridine-2-carboxamide 159) N-{(1R,2S,5S)-2-{[(5-chloro-3-fluoroindol-2-yl)carbonyl]amino}-5-[(dimethylamino)carbonyl]cyclohexyl}-5-methyl-4,5,6,7-tetrahydrothiazolo[5,4-c]pyridine-2-carboxamide 160) N-{(1R,2S,5S)-2-{[(3-bromo-5-chloroindol-2-yl)carbonyl]amino}-5-[(dimethylamino)carbonyl]cyclohexyl}-5-methyl-4,5,6,7-tetrahydrothiazolo[5,4-c]pyridine-2-carboxamide 161) N-{(1R,2S,5S)-2-{[(3-chloro-5-fluoroindol-2-yl)carbonyl]amino}-5-[(dimethylamino)carbonyl]cyclohexyl}-5-methyl-4,5,6,7-tetrahydrothiazolo[5,4-c]pyridine-2-carboxamide 162) N-{(1R,2S,5S)-2-{[(5-chloro-3-formylindol-2-yl)carbonyl]amino}-5-[dimethylamino)carbonyl]cyclohexyl}-5-methyl-4,5,6,7-tetrahydrothiazolo[5,4-c]pyridine-2-carboxamide 163) 5-chloro-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-$N^3,N^3$-dimethylindole-2,3-dicarboxamide 164) N-{(1R,2S,5S)-2-[(6-chloro-2-naphthoyl)amino]-5-[(dimethylamino)carbonyl]cyclohexyl}-5-methyl-4,5,6,7-tetrahydrothiazolo[5,4-c]pyridine-2-carboxamide 165) 7-chloro-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)cinnoline-3-carboxamide 166) N-{(1R,2S,5S)-2-{[(5-chlorobenzimidazol-2-yl)carbonyl]amino}-5-[(dimethylamino)carbonyl]cyclohexyl}-5-methyl-4,5,6,7-tetrahydrothiazolo[5,4-c]pyridine-2-carboxamide 167) N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-7-fluoroisoquinoline-3-carboxamide 168) N-{(1R,2S,5S)-2-{[(7-chloro-2H-chromen-3-yl)carbonyl]amino}-5-[(dimethylamino)carbonyl]cyclohexyl}-5-methyl-4,5,6,7-tetrahydrothiazolo[5,4-c]pyridine-2-carboxamide 169) N-{(1R,2S,5S)-2-{[(E)-3-(4-chlorophenyl)-2-propenoyl]amino}-5-[(dimethylamino)carbonyl]cyclohexyl}-5-methyl-4,5,6,7-tetrahydrothiazolo[5,4-c]pyridine-2-carboxamide 170) 6-chloro-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-4-oxo-1,4-dihydroquinoline-2-carboxamide 171) 7-chloro-N-((1S,2R,4S)-4-{[ethyl(methyl)amino]carbonyl}-2-{[(5-methyl-4,5,6,7-tetrahydrothiazolo[5,4-c]pyridin-2-yl)carbonyl]amino}cyclohexyl)isoquinoline-3-carboxamide 172) N-{(1R*,2S*,5S*)-2-{[(5-chloroindol-2-yl)carbonyl]amino}-5-[2-(dimethylamino)-2-oxoethyl]cyclohexyl}-5-methyl-4,5,6,7-tetrahydrothiazolo[5,4-c]pyridine-2-carboxamide 173) N-{(1R,2S,5S)-2-{[(5-chloroindol-2-yl)carbonyl]amino}-5-[(methylsulfonyl)methyl]cyclohexyl}-5-methyl-4,5,6,7-tetrahydrothiazolo[5,4-c]pyridine-2-carboxamide 174) N-{(1R,2S,5S)-2-{[2-chloro-6'1'-thieno[2,3-b]pyrrol-5-yl)carbonyl]amino}-5-[(dimethylamino)carbonyl]cyclohexyl}-5-methyl-4,5,6,7-tetrahydrothiazolo[5,4-c]pyridine-2-carboxamide 175) N-{(1R,2S,5S)-2-{[3-(4-chlorophenyl)-2-propynoyl]amino}-5-[(dimethylamino)carbonyl]cyclohexyl}-5-methyl-4,5,6,7-tetrahydrothiazolo[5,4-c]pyridine-2-carboxamide 176) 6-chloro-N-((1S,2R,4S)-4-[(dimethylamino)carbonyl]-2-{[5-methyl-4,5,6,7-tetrahydrothiazolo[5,4-c]pyridin-2-yl)carbonyl]amino}cyclohexyl)-4-oxo-1,4-dihydroquinazoline-2-carboxamide 177) N-{(1R,2S,5S)-2-{[2-(4-chloroanilino)-2-oxoethanethioyl]amino}-5-[(dimethylamino)carbonyl]cyclohexyl}-5-methyl-4,5,6,7-tetrahydrothiazolo[5,4-c]pyridine-2-carboxamide 178) N-{(1R,2S,5S)-2-({2-[(5-chloropyridin-2-yl)amino]-2-oxoethanethioyl}amino)-5-[(dimethylamino)carbonyl]cyclohexyl}-5-methyl-4,5,6,7-tetrahydrothiazolo[5,4-c]pyridine-2-carboxamide 179) N-{(1R,2S,5S)-2-({2-[(5-chloropyridin-2-yl)amino]-2-thioxoacetyl}amino)-5-[(dimethylamino)carbonyl]cyclohexyl}-5-methyl-4,5,6,7-tetrahydrothiazolo[5,4-c]pyridine-2-carboxamide 180) $N^1$-(5-chloro-2-thienyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide 181) N-{(1R,2S,5S)-2-{[(4-chloroanilino)carbonyl]amino}-5-[(dimethylamino)carbonyl]cyclohexyl}-5-methyl-4,5,6,7-tetrahydrothiazolo[5,4-c]pyridine-2-carboxamide 182) $N^1$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-$N^2$-(5-fluoropyridin-2-yl)ethanediamide 183) $N^1$-[4-chloro-2-(trifluoromethyl)phenyl]-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide 184) $N^1$-{4-chloro-2-[(dimethylamino)carbonyl]phenyl}-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide 185) $N^1$-[4-chloro-2-(hydroxymethyl)phenyl]-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide 186) $N^1$-(4-chloro-2-methoxyphenyl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide 187) N-{(1R,2S,5S)-2-{[2-(4-chloro anilino)-2-(hydroxyimino)acetyl]amino}-5-[(dimethylamino)carbonyl]cyclohexyl}-5-methyl-4,5,6,7-tetrahydrothiazolo[5,4-c]pyridine-2-carboxamide 188) $N^1$-(4-chlorophenyl)-$N^2$-43R,4S)-1-(2-methoxyacetyl)-3-{[(5-methyl-4,5,6,7-tetrahydrothiazolo[5,4-c]pyridin-2-yl)carbonyl]amino}piperidin-4-yl)ethanediamide 189) $N^1$-(5-chloropyridin-2-yl)-$N^2$43R,4S)-1-(2-methoxyacetyl)-3-{[(5-methyl-4,5,6,7-tetrahydrothiazolo[5,4-c]pyridin-2-yl)carbonyl]amino}piperidin-4-yl)ethanediamide 190) $N^1$-(5-bromopyridin-2-yl)-$N^2$-((3R,4S)-1-(2-methoxyacetyl)-3-{[(5-methyl-4,5,6,7-tetrahydrothiazolo[5,4-c]pyridin-2-yl)carbonyl]amino}piperidin-4-yl)ethanediamide 191) $N^1$-(4-chlorophenyl)-$N^3$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)malonamide 192) $N^1$-(3-chlorophenyl)-$N^3$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)malonamide 193) $N^1$-(5-chloropyridin-2-yl)-$N^2$-((1S,2R,4S)-4-{[ethyl(methyl)amino]carbonyl}-2-{[(5-methyl-4,5,6,7-tetrahydrothiazolo[5,4-c]pyridin-2-yl)carbonyl]amino}cyclohexyl)ethanediamide 194) N$^1$-(4-chlorophenyl)-N$^2$-((1S,2R,4S)-4-{[ethyl(methyl)amino]carbonyl}-2-{[(5-methyl-4,5,6,7-tetrahydrothiazolo[5,4-c]pyridin-2-yl)carbonyl]amino}cyclohexyl)ethanediamide 195) N$^1$-(5-bromopyridin-2-yl)-N$^2$-((1S,2R,4S)-4-{[ethyl(methyl)amino]carbonyl}-2-{[(5-methyl-4,5,6,7-tetrahydrothiazolo[5,4-c]pyridin-2-yl)carbonyl]amino}cyclohexyl)ethanediamide 196) N$^1$-(4-chloro-3-fluorophenyl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide 197) N-{(1R,2S,5S)-2-{[3-(4-chlorophenyl)-3-oxopropanoyl]amino}-5-[(dimethylamino)carbonyl]cyclohexyl}-5-methyl-4,5,6,7-tetrahydrothiazolo[5,4-c]pyridine-2-carboxamide 198) N$^1$-[(5-chloropyridin-2-yl)amino]-N$^2$-41R,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide 199) N$^1$-(4-chlorophenyl)-N$^2$41R,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide 200) N$^1$-(5-chloropyridin-2-yl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-N$^1$-methylethanediamide 201) N$^1$-(5-chloropyrimidin-2-yl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide 202) N$^1$-(4-chloro-3-methoxyphenyl)-N$^2$-((1S,2R,4S)-4-[(dimethyl-amino)carbonyl]-2-{[(5-methyl-4,5,6,7-tetrahydrothiazolo[5,4-c]pyridin-2-yl)carbonyl]amino}cyclohexyl)ethanediamide 203) N$^1$-(4-chlorophenyl)-N$^2$41R*,2R*)-2-{[(5-methyl-4,5,6,7-tetrahydrothiazolo[5,4-c]pyridin-2-yl)carbonyl]amino}cyclopentyl)ethanediamide 204) N$^1$-(5-chloropyridin-2-yl)-N$^2$41R*,2R*)-2-{[(5-methyl-4,5,6,7-tetrahydrothiazolo[5,4-c]pyridin-2-yl)carbonyl]amino}cyclopentyl)ethanediamide 205) N$^1$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-N$^2$-(4-ethynylphenyl)ethanediamide 206) N$^1$-(5-chloropyrazin-2-yl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide 207) N$^1$-(4-chloro-3-nitrophenyl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide 208) N$^1$-(4-chloro-2-nitrophenyl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide 209) N$^1$-(3-amino-4-chlorophenyl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide 210) N$^1$-(2-amino-4-chlorophenyl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide 211) N$^1$-(6-chloro-4-methylpyridin-3-yl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide 212) N-{(1R,2S,5S)-2-({[(E)-2-(4-chlorophenyl)diazenyl]carbonyl}amino)-5-[(dimethylamino)carbonyl]cyclohexyl}-5-methyl-4,5,6,7-tetrahydrothiazolo[5,4-c]pyridine-2-carboxamide 213) N-{(1R,2S,5S)-2-({[2-(4-chlorophenyl)hydrazino]carbonyl}amino)-5-[(dimethylamino)carbonyl]cyclohexyl}-5-methyl-4,5,6,7-tetrahydrothiazolo[5,4-c]pyridine-2-carboxamide 214) N$^1$-(5-chloropyridin-2-yl)-N$^2$-((1S,2R,4S)-4-[(dimethylamino)carbonyl]-2-{[(4,5,6,7-tetrahydrothiazolo[5,4-c]pyridin-2-yl)carbonyl]amino}cyclohexyl)ethanediamide 215) N-{(3R*,4S*)-4-{[(5-chloroindol-2-yl)carbonyl]amino}-1-[(1-hydroxycyclopropyl)carbonyl]piperidin-3-yl}-5-methyl-4,5,6,7-tetrahydrothiazolo[5,4-c]pyridine-2-carboxamide 216) N-{(3R*,4S*)-4-{[(5-chloroindol-2-yl)carbonyl]amino}-1-[(1-methoxycyclopropyl)carbonyl]piperidin-3-yl}-5-methyl-4,5,6,7-tetrahydrothiazolo[5,4-c]pyridine-2-carboxamide 217) 7-chloro-N-((3R,4S)-1-(2-methoxyacetyl)-3-{[(5-methyl-4,5,6,7-tetrahydrothiazolo[5,4-c]pyridin-2-yl)carbonyl]amino}piperidin-4-yl)-3-isoquinolinecarboxamide 218) N$^1$-(4-chloro-3-fluorophenyl)-N$^2$43R,4S)-1-(2-methoxyacetyl)-3-{[(5-methyl-4,5,6,7-tetrahydrothiazolo[5,4-c]pyridin-2-yl)carbonyl]amino}piperidin-4-yl)ethanediamide 219) N$^1$-(5-chloro-2-thienyl)-N$^2$-((3R,4S)-1-(2-methoxyacetyl)-3-{[(5-methyl-4,5,6,7-tetrahydrothiazolo[5,4-c]pyridin-2-yl)carbonyl]amino}piperidin-4-yl)ethanediamide 220) N-{(1R,2S,5S)-2-{[2-(4-chlorophenoxy)acetyl]amino}-5-[(dimethylamino)carbonyl]cyclohexyl}-5-methyl-4,5,6,7-tetrahydrothiazolo[5,4-c]pyridine-2-carboxamide 221) N-{(1R,2S,5S)-2-{[(6-chloro-4-oxo-4H-chromen-2-yl)carbonyl]amino}-5-[(dimethylamino)carbonyl]cyclohexyl}-5-methyl-4,5,6,7-tetrahydrothiazolo[5,4-c]pyridine-2-carboxamide 222) 7-chloro-N-((3R,4S)-1-(2-methoxyacetyl)-3-{[(5-methyl-4,5,6,7-tetrahydrothiazolo[5,4-c]pyridin-2-yl)carbonyl]amino}piperidin-4-yl)-3-cinnolinecarboxamide 223) N-((1R,2 S,5S)-5-[(dimethylamino)carbonyl]-2-{[2-(4-fluoro anilino)-2-oxoethanethioyl]amino}cyclohexyl)-5-methyl-4,5,6,7-tetrahydrothiazolo[5,4-c]pyridine-2-carboxamide 224) N-[(1R,2S,5S)-5-[(dimethylamino)carbonyl]-2-({2-[(5-fluoropyridin-2-yl)amino]-2-oxoethanethioyl}amino)cyclohexyl]-5-methyl-4,5,6,7-tetrahydrothiazolo[5,4-c]pyridine-2-carboxamide 225) N-{(1R,2 S,5S)-2-[({[(4-chlorophenyl)sulfonyl]amino}carbonyl)amino]-5-[(dimethylamino)carbonyl]cyclohexyl}-5-methyl-4,5,6,7-tetrahydrothiazolo[5,4-c]pyridine-2-carboxamide 226) N$^1$-(5-chloropyridin-2-yl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide 227) N$^1$-(5-chloropyridin-2-yl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide 228) $N^1$-(5-chloropyridin-2-yl)-$N^2$-((1S,2R,4S)-4-[(methylamino)carbonyl]-2-{[(5-methyl-4,5,6,7-tetrahydrothiazolo[5,4-c]pyridin-2-yl)carbonyl]amino}cyclohexyl)ethanediamide 229) N-{(1R,2S,5S)-5-[(dimethylamino)carbonyl]-2-({2-{[(5-methylpyridin-2-yl)amino]-2-oxoethanethioyl}amino)cyclohexyl}-5-methyl-4,5,6,7-tetrahydrothiazolo[5,4-c]pyridine-2-carboxamide 230) N-[(3R,4S)-4-{[2-(4-chloroanilino)-2-oxoethanethioyl]amino}-1-(2-methoxyacetyl)piperidin-3-yl]-5-methyl-4,5,6,7-tetrahydrothiazolo[5,4-c]pyridine-2-carboxamide 231) $N^1$-(5-chloropyridin-2-yl)-$N^2$-((1S,2R,4S)-4-[(dimethylamino)carbothioyl]-2-{[(5-methyl-4,5,6,7-tetrahydrothiazolo[5,4-c]pyridin-2-yl)carbonyl]amino}cyclohexyl)ethanediamide 232) $N^1$-(5-chloropyridin-2-yl)-$N^2$43R,4S)-1-(2-methoxyethanethioyl)-3-{[(5-methyl-4,5,6,7-tetrahydrothiazolo[5,4-c]pyridin-2-yl)carbonyl]amino}piperidin-4-yl)ethanediamide 233) (1S,3R,4S)-4-({2-[(5-chloropyridin-2-yl)amino]-2-oxoacetyl}amino)-3-{[(5-methyl-4,5,6,7-tetrahydrothiazolo[5,4-c]pyridin-2-yl)carbonyl]amino}cyclohexanecarboxylic acid 2,2,2-trichloroethyl ester 234) (1S,3R,4S)-4-({2-[(5-chloropyridin-2-yl)amino]-2-oxoacetyl}amino)-3-{[(5-methyl-4,5,6,7-tetrahydrothiazolo[5,4-c]pyridin-2-yl)carbonyl]amino}cyclohexanecarboxylic acid 235) N-{(1R,2S,5S)-2-{[2-(4-chloroanilino)-1-methoxyimino-2-oxoethyl]amino}-5-[dimethylamino)carbonyl]cyclohexyl}-5-methyl-4,5,6,7-tetrahydrothiazolo[5,4-c]pyridine-2-carboxamide 236) $N^1$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-$N^2$-(5-ethynylpyridin-2-yl)ethanediamide 237) N-{(1R,2S,5S)-2-({2-[(6-chloropyridazin-3-yl)amino]-2-oxoethanethioyl}amino)-5-[(dimethylamino)carbonyl]cyclohexyl}-5-methyl-4,5,6,7-tetrahydrothiazolo[5,4-c]pyridine-2-carboxamide 238) N-{(1R,2S,5S)-2-({2-[(6-chloropyridin-3-yl)amino]-2-oxoethanethioyl}amino)-5-[(dimethylamino)carbonyl]cyclohexyl}-5-methyl-4,5,6,7-tetrahydrothiazolo[5,4-c]pyridine-2-carboxamide 239) $N^1$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-$N^2$-(5-methylpyridin-2-yl)ethanediamide 240) $N^1$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-$N^2$-(4-methylphenyl)ethanediamide 241) $N^1$-(5-chloropyridin-2-yl)-$N^2$-((1S,2R,4S)-4-[(methylamino)carbothioyl]-2-{[(5-methyl-4,5,6,7-tetrahydrothiazolo[5,4-c]pyridin-2-yl)carbonyl]amino}cyclohexyl)ethanediamide 242) N-{(1R,2S,5S)-2-{[(4-chloroanilino)sulfonyl]amino}-5-[(dimethylamino)carbonyl]cyclohexyl}-5-methyl-4,5,6,7-tetrahydrothiazolo[5,4-c]pyridine-2-carboxamide 243) N-{(1R,2S,5S)-2-({2-[(5-chloropyrimidin-2-yl)amino]-2-oxoethanethioyl}amino)-5-[(dimethylamino)carbonyl]cyclohexyl}-5-methyl-4,5,6,7-tetrahydrothiazolo[5,4-c]pyridine-2-carboxamide 244) N-{(1R,2S,5S)-2-{[2-(4-chloro-3-nitroanilino)-2-oxoethanethioyl]amino}-5-[(dimethylamino)carbonyl]cyclohexyl}-5-methyl-4,5,6,7-tetrahydrothiazolo[5,4-c]pyridine-2-carboxamide 245) N-{(1R,2S,5S)-2-{[2-(3-amino-4-chloroanilino)-2-oxoethanethioyl]amino}-5-[(dimethylamino)carbonyl]cyclohexyl}-5-methyl-4,5,6,7-tetrahydrothiazolo[5,4-c]pyridine-2-carboxamide 246) N-{(1R,2S,5S)-2-{[(7-chlorocinnolin-3-yl)carbothioyl]amino}-5-[(dimethylamino)carbonyl]cyclohexyl}-5-methyl-4,5,6,7-tetrahydrothiazolo[5,4-c]pyridine-2-carboxamide 247) N-{(1R,2S,5S)-2-({[(4-chlorobenzoyl)amino]carbonyl}amino)-5-[(dimethylamino)carbonyl]cyclohexyl}-5-methyl-4,5,6,7-tetrahydrothiazolo[5,4-c]pyridine-2-carboxamide 248) N-{(1R,2S,5S)-2-{[(E)-3-(5-chloropyridin-2-yl)acryloyl]amino}-5-[(dimethylamino)carbonyl]cyclohexyl}-5-methyl-4,5,6,7-tetrahydrothiazolo[5,4-c]pyridine-2-carboxamide 249) N-{(1R,2S,5S)-2-{[(Z)-3-(4-chlorophenyl)-2-fluoroacryloyl]amino}-5-[(dimethylamino)carbonyl]cyclohexyl}-5-methyl-4,5,6,7-tetrahydrothiazolo[5,4-c]pyridine-2-carboxamide 250) N-{(1R,2S,5S)-2-({2-[(5-chloropyridin-2-yl)amino]-2-oxoethanethioyl}amino)-5-[(methylamino)carbonyl]cyclohexyl}-5-methyl-4,5,6,7-tetrahydrothiazolo[5,4-c]pyridine-2-carboxamide 251) (3-{[((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)amino]carbonyl}phenyl)(imino)methylcarbamic acid tert-butyl ester 252) N-{(1R,2S,5S)-2-({3-[amino(imino)methyl]benzoyl}amino)-5-[(dimethylamino)carbonyl]cyclohexyl}-5-methyl-4,5,6,7-tetrahydrothiazolo[5,4-c]pyridine-2-carboxamide 253) N-{(1R,2S,5S)-2-[(3-cyanobenzoyl)amino]-5-[(dimethylamino)carbonyl]cyclohexyl}-5-methyl-4,5,6,7-tetrahydrothiazolo[5,4-c]pyridine-2-carboxamide 254) N-{(1R,2S,5S)-2-({3-[amino(hydroxyimino)methyl]benzoyl}amino)-5-[(dimethylamino)carbonyl]cyclohexyl}-5-methyl-4,5,6,7-tetrahydrothiazolo[5,4-c]pyridine-2-carboxamide 255) (3-{[((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)amino]carbonyl}phenyl)(imino)methylcarbamic acid ethyl ester 256) N-[(1R,2S,5S)-5-[(dimethylamino)carbonyl]-2-({3-[imino(methylamino)methyl]benzoyl}amino)cyclohexyl]-5-methyl-4,5,6,7-tetrahydrothiazolo[5,4-c]pyridine-2-carboxamide 257) N-{(1R,2S,5S)-2-({3-[amino(methoxyimino)methyl]benzoyl}amino)-5-[(dimethylamino)carbonyl]cyclohexyl}-5-methyl-4,5,6,7-tetrahydrothiazolo[5,4-c]pyridine-2-carboxamide 258) N-{(1R,2S,5S)-2-{[(Z)-3-(5-chlorothien-2-yl)-2-fluoro-2-propenoyl]amino}-5-[(dimethylamino)carbonyl]cyclohexyl}-5-methyl-4,5,6,7-tetrahydrothiazolo[5,4-c]pyridine-2-carboxamide 259) (1S,3R,4S)-4-({2-[(5-chloropyridin-2-yl)amino]-2-oxoethanethioyl}amino)-3-{[(5-methyl-4,5,6,7-tetrahydrothiazolo[5,4-c]pyridin-2-yl)carbonyl]amino}cyclohexanecarboxylic acid tert-butyl ester 260) (1S,3R,4S)-4-({2-[(5-chloro-2-pyridinyl)amino]-2-oxoethanethioyl}amino)-3-{[(5-methyl-4,5,6,7-tetrahydrothiazolo[5,4-c]pyridin-2-yl)carbonyl]amino}cyclohexanecarboxylic acid 261) N$^1$-(5-chloropyridin-2-yl)-N$^2$-[(1S,2R,4R)-2-{[(5-methyl-4,5,6,7-tetrahydrothiazolo[5,4-c]pyridin-2-yl)carbonyl]amino}-4-(thiazol-2-yl)cyclohexyl]ethanediamide, N$^1$-(5-chloropyridin-2-yl)-N$^2$-[(1S,2R,4S)-2-{[(5-methyl-4,5,6,7-tetrahydrothiazolo[5,4-c]pyridin-2-yl)carbonyl]amino}-4-(thiazol-2-yl)cyclohexyl]ethanediamide 262) N$^1$-(5-chloropyridin-2-yl)-N$^2$-[(1S,2R,4S)-2-{[(5-methyl-4,5,6,7-tetrahydrothiazolo[5,4-c]pyridin-2-yl)carbonyl]amino}-4-(1,2,4-oxadiazol-3-yl)cyclohexyl]ethanediamide 263) N$^1$-(5-chloropyridin-2-yl)-N$^2$-[(1S,2R,4S)-2-{[(5-methyl-4,5,6,7-tetrahydrothiazolo[5,4-c]pyridin-2-yl)carbonyl]amino}-4-(5-methyl-1,3,4-oxadiazol-2-yl)cyclohexyl]ethanediamide 264) N$^1$-(5-chloropyridin-2-yl)-N$^2$-[(1S,2R,4S)-2-{[(5-methyl-4,5,6,7-tetrahydrothizolo[5,4-c]pyridin-2-yl)carbonyl]amino}-4-(1,3,4-oxadiazol-2-yl)cyclohexyl]ethanediamide 265) N$^1$-(5-chloropyridin-2-yl)-N$^2$-[(1S,2R,4S)-2-{[(5-methyl-4,5,6,7-tetrahydrothiazolo[5,4-c]pyridin-2-yl)carbonyl]amino}-4-(1,3-oxazol-2-yl)cyclohexyl]ethanediamide 266) N$^1$-(5-chloropyridin-2-yl)-N$^2$-((1S,2R,4S)-4-(5-methyl-1,3,4-oxadiazol-2-yl)-2-{[(5-methyl-4,5,6,7-tetrahydrothiazolo[5,4-c]pyridin-2-yl)carbonyl]amino}cyclohexyl)ethanediamide 267) N$^1$-(5-chloropyridin-2-yl)-N$^2$-[(1S,2R,4S)-2-{[(5-methyl-4,5,6,7-tetrahydrothiazolo[5,4-c]pyridin-2-yl)carbonyl]amino}-4-(1,3,4-thiadiazol-2-yl)cyclohexyl]ethanediamide 268) N-[(1R,2S,5S)-5-[(dimethylamino)carbonyl]-2-({2-[(5-fluoropyridin-2-yl)amino]-2-oxoethanethioyl}amino)cyclohexyl]-5-methyl-4,5,6,7-tetrahydrothiazolo[5,4-c]pyridine-2-carboxamide 269) N-[(1R,2S,5S)-5-[(dimethylamino)carbonyl]-2-({2-[(5-fluoropyridin-2-yl)amino]-2-oxoethanethioyl}amino)cyclohexyl]-5-methyl-4,5,6,7-tetrahydrothiazolo[5,4-c]pyridine-2-carboxamide 270) N$^1$-(5-chloropyridin-2-yl)-N$^2$-[(1S,2R,4S)-2-{[(5-methyl-4,5,6,7-tetrahydrothiazolo[5,4-c]pyridin-2-yl)carbonyl]amino}-4-(5-methyl-1,3,4-thiadiazol-2-yl)cyclohexyl]ethanediamide 271) N$^1$-(5-chloropyridin-2-yl)-N$^2$-[(1S,2R,4S)-2-{[(5-methyl-4,5,6,7-tetrahydrothiazolo[5,4-c]pyridin-2-yl)carbonyl]amino}-4-(1,3-oxazol-5-yl)cyclohexyl]ethanediamide 272) N$^1$-(5-chloropyridin-2-yl)-N$^2$-((1S,2R,4S)-4-(5-methyl-1,2,4-oxadiazol-3-yl)-2-{[(5-methyl-4,5,6,7-tetrahydrothiazolo[5,4-c]pyridin-2-yl)carbonyl]amino}cyclohexyl)ethanediamide 273) N$^1$-(5-chloropyridin-2-yl)-N$^2$-((1S,2R,4S)-2-{[(5-methyl-4,5,6,7-tetrahydrothiazolo[5,4-c]pyridin-2-yl)carbonyl]amino}-4-(4H-1,2,4-triazol-4-yl)cyclohexyl)ethanediamide 274) N$^1$-(5-chloro-2-thienyl)-N$^2$-((1S,2R,4S)-4-(5-methyl-1,3,4-oxadiazol-2-yl)-2-{[(5-methyl-4,5,6,7-tetrahydrothiazolo[5,4-c]pyridin-2-yl)carbonyl]amino}cyclohexyl)ethanediamide 275) N$^1$-(5-bromo-2-pyridinyl)-N$^2$-((1S,2R,4S)-4-(5-methyl-1,3,4-oxadiazol-2-yl)-2-{[(5-methyl-4,5,6,7-tetrahydrothiazolo[5,4-c]pyridin-2-yl)carbonyl]amino}cyclohexyl)ethanediamide 276) N$^1$-(4-chlorophenyl)-N$^2$-((1S,2R,4S)-4-(5-methyl-1,3,4-oxadiazol-2-yl)-2-{[(5-methyl-4,5,6,7-tetrahydrothiazolo[5,4-c]pyridin-2-yl)carbonyl]amino}cyclohexyl)ethanediamide 277) N-[(1R,2S,5S)-2-{[(5-chloro-1H-indol-2-yl)carbonyl]amino}-5-(5-methyl-1,3,4-oxadiazol-2-yl)cyclohexyl]-5-methyl-4,5,6,7-tetrahydrothiazolo[5,4-c]pyridine-2-carboxamide 278) N$^1$-((1S,2R,4S)-4-(5-methyl-1,3,4-oxadiazol-2-yl)-2-{[(5-methyl-4,5,6,7-tetrahydrothiazolo[5,4-c]pyridin-2-yl)carbonyl]amino}cyclohexyl)-N$^2$-{5-[2-(trimethylsilyl)ethynyl]pyridin-2-yl}ethanediamide 279) N$^1$-(5-ethynylpyridin-2-yl)-N$^2$-((1S,2R,4S)-4-(5-methyl-1,3,4-oxadiazol-2-yl)-2-{[(5-methyl-4,5,6,7-tetrahydrothiazolo[5,4-c]pyridin-2-yl)carbonyl]amino}cyclohexyl)ethanediamide 280) 7-chloro-N-((1S,2R,4S)-4-(5-methyl-1,3,4-oxadiazol-2-yl)-2-{[(5-methyl-4,5,6,7-tetrahydrothiazolo[5,4-c]pyridin-2-yl)carbonyl]amino}cyclohexyl)-3-cinnolinecarboxamide 281) N-[(1R,2S,5S)-2-{[(Z)-3-(4-chlorophenyl)-2-fluoroacryloyl]amino}-5-(5-methyl-1,3,4-oxadiazol-2-yl)cyclohexyl]-5-methyl-4,5,6,7-tetrahydrothiazolo[5,4-c]pyridine-2-carboxamide 282) 7-chloro-N-((1S,2R,4S)-4-(5-methyl-1,3,4-oxadiazol-2-yl)-2-{[(5-methyl-4,5,6,7-tetrahydrothiazolo[5,4-c]pyridin-2-yl)carbonyl]amino}cyclohexyl)-3-isoquinolinecarboxamide 283) 6-chloro-N-((1S,2R,4S)-4-(5-methyl-1,3,4-oxadiazol-2-yl)-2-{[(5-methyl-4,5,6,7-tetrahydrothiazolo[5,4-c]pyridin-2-yl)carbonyl]amino}cyclohexyl)-4-oxo-1,4-dihydro-2-quinazolinecarboxamide 284) N$^1$-(5-chloropyridin-2-yl)-N$^2$-[(1S,2R,4S)-2-{[(5-methyl-4,5,6,7-tetrahydrothiazolo[5,4-c]pyridin-2-yl)carbonyl]amino}-4-(1,2,4-oxadiazol-5-yl)cyclohexyl]ethanediamide 285) N$^1$-(5-chloropyridin-2-yl)-N$^2$-{(1S,2R,4S)-2-{[(5-methyl-4,5,6,7-tetrahydrothiazolo[5,4-c]pyridin-2-yl)carbonyl]amino}-4-[5-(trifluoromethyl)-1,3,4-oxadiazol-2-yl]cyclohexyl}ethanediamide 286) N$^1$-(5-chloro-2-thienyl)-N$^2$-01S,2R,4S)-4-(3-methyl-1,2,4-oxadiazol-5-yl)-2-{[(5-methyl-4,5,6,7-tetrahydrothiazolo[5,4-c]pyridin-2-yl)carbonyl]amino}cyclohexyl)ethanediamide 287) N$^1$-(6-chloropyridazin-3-yl)-N$^2$-((1S,2R,4S)-4-(3-methyl-1,2,4-oxadiazol-5-yl)-2-{[(5-methyl-4,5,6,7-tetrahydrothiazolo[5,4-c]pyridin-2-yl)carbonyl]amino}cyclohexyl)ethanediamide 288) N$^1$-(5-chloropyridin-2-yl)-N$^2$-[(1S,2R,4S)-2-{[(5-methyl-4,5,6,7-tetrahydrothiazolo[5,4-c]pyridin-2-yl)carbonyl]amino}-4-(2-oxo-1,3-oxazolidin-3-yl)cyclohexyl]ethanediamide 289) N$^1$-(5-chloropyridin-2-yl)-N$^2$-[(1S,2R,4S)-2-{[(5-methyl-4,5,6,7-tetrahydrothiazolo[5,4-c]pyridin-2-yl)carbonyl]amino}-4-(tetrazol-1-yl)cyclohexyl]ethanediamide 290) N$^1$-(5-chloropyridin-2-yl)-N$^2$-[(1S,2R,4S)-2-{[(5-methyl-4,5,6,7-tetrahydrothiazolo[5,4-c]pyridin-2-yl)carbonyl]amino}-4-(1H-pyrrol-1-yl)cyclohexyl]ethanediamide 291) N$^1$-(5-chloropyridin-2-yl)-N$^2$-[(1S,2R,4S)-2-{[(5-methyl-4,5,6,7-tetrahydrothiazolo[5,4-c]pyridin-2-yl)carbonyl]amino}-4-(1,2,4-triazol-5-yl)cyclohexyl]ethanediamide 292) N$^1$-(5-chloropyridin-2-yl)-N$^2$-[(1S,2R,4S)-2-{[(5-methyl-4,5,6,7-tetrahydrothiazolo[5,4-c]pyridin-2-yl)carbonyl]amino}-4-(1-methyl-1H-1,2,4-triazol-5-yl)cyclohexyl]ethanediamide 293) 7-chloro-N-((1S,2R,4S)-4-(3-methyl-1,2,4-oxadiazol-5-yl)-2-{[(5-methyl-4,5,6,7-tetrahydrothiazolo[5,4-c]pyridin-2-yl)carbonyl]amino}cyclohexyl)-3-cinnolinecarboxamide 294) N[1]-(5-chloropyridin-2-yl)-N[2]-((3R,4S)-3-{[(5-methyl-4,5,6,7-tetrahydrothiazolo[5,4-c]pyridin-2-yl)carbonyl]amino}-1-(thiazol-2-yl)piperidin-4-yl)ethanediamide Each of these compounds may be produced by use of the compound (5) as a starting material through a method described in Examples of International Publication WO2004/058728 pamphlet.

Example

To further illustrate the present invention in greater detail, the following examples will be given. However, it is to be understood that the present invention is not limited thereto.

Production Example 1

2-Cyano-5-methyl-4,5,6,7-tetrahydrothiazolo[5,4-c]pyridine hydrochloride monohydrate

[F73]

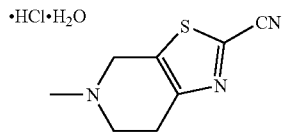

N,N-Dimethylacetamide (25 mL) was added to a mixture of copper cyanide (2.88 g) and sodium cyanide (1.58 g), and the resultant mixture was heated at 150° C. until all ingredients were completely dissolved, to thereby give a clear, colorless solution. 2-Bromo-5-methyl-4,5,6,7-tetrahydrothiazolo[5,4-c]pyridine (5.00 g) was added to the solution, and the resultant mixture was stirred at 150° C. for 18 hours. The reaction mixture was allowed to cool to room temperature, and toluene and saturated aqueous sodium hydrogencarbonate were added thereto. After any insoluble material was filtered off, the toluene layer was separated from the aqueous layer, and the aqueous layer was further extracted with toluene twice. The toluene layers were combined, and the combined toluene layer was dried over sodium sulfate anhydrate. After any insoluble material was filtered off, the filtrate was concentrated under reduced pressure, and the concentrated residue was dissolved in ethanol (35 mL). To the solution was added dropwise 1N HCl in ethanol (25 mL) at room temperature, to thereby form a hydrochloride salt, and the resultant mixture was stirred at 0° C. for 1 hour. The precipitated crystals were collected by filtration, and were washed with ethanol (20 mL). The thus-obtained wet crystal was dried at room temperature under reduced pressure, to thereby give 3.05 g of the title compound.

$^1$H-NMR (D$_2$O) δ ppm: 4.72 (br, 2H), 3.77 (br, 2H), 3.36-3.29 (t, 2H, J=6.2 Hz), 3.13 (s, 3H).

MS (FAB) m/z: 180 (M+H)$^+$

Elementary analysis: as C$_{18}$H$_{12}$ClN$_3$OS,

Calculated: C, 41.11; H, 5.18; Cl, 15.17; N, 17.98; S, 13.72

Found: C, 41.22; H, 4.99; Cl, 15.26; N, 17.95; S, 13.69

Production Example 2

2-Cyano-5-methyl-4,5,6,7-tetrahydrothiazolo[5,4-c]pyridine

[F74]

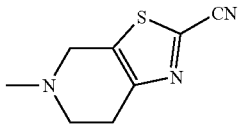

A solution of sodium hydrogencarbonate (272.33 mg) in water (5 mL) was added to 2-cyano-5-methyl-4,5,6,7-tetrahydrothiazolo[5,4-c]pyridine hydrochloride monohydrate (500.30 mg) at room temperature, and after all ingredients were completely dissolved, the resultant solution was extracted with toluene three times (10 mL×3). The toluene layers were combined, and the combined toluene layer was dried over sodium sulfate anhydrate (2.00 g). After any insoluble material was filtered off, the filtrate was concentrated at 40° C. under reduced pressure, to thereby give 384.28 mg of the title compound.

$^1$H-NMR (CDCl$_3$) δ ppm: 3.76-3.73 (t, 2H, J=1.5 Hz), 3.03-2.98 (dt, 2H, J=1.5, 5.9 Hz), 2.89-2.84 (t, 2H, J=5.9 Hz), 2.52 (s, 3H).

MS (FAB) m/z: 180 (M+H)$^+$

Elementary analysis: as C$_8$H$_9$N$_3$S,

Calculated: C, 53.61; H, 5.06; N, 23.44; S, 17.89

Found: C, 53.40; H, 5.08; N, 23.41; S, 17.89

Production Example 3

5-Methyl-4,5,6,7-tetrahydrothiazolo[5,4-c]pyridine-2-carboxylic acid hydrochloride

[F75]

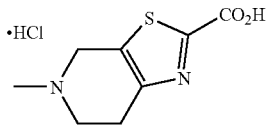

To 2-cyano-5-methyl-4,5,6,7-tetrahydrothiazolo[5,4-c]pyridine hydrochloride monohydrate (500.61 mg) were added ethanol (5 mL) and 4N aqueous lithium hydroxide (1.34 mL) at room temperature, and the resultant mixture was stirred at 50° C. for 7 hours. After the reaction mixture was cooled with ice-water, 1N HCl in ethanol (7.5 mL) was added thereto, to thereby form a hydrochloride salt, followed by stirring at the same temperature for 1.5 hours. The precipitated crystals were collected by filtration, and were washed with ethanol (2 mL). The wet crystal was dried at room temperature under reduced pressure, to thereby give 466.98 mg of the title compound.

$^1$H-NMR (D$_2$O) δ ppm: 4.82-4.88 (d, 1H, J=16.0 Hz), 4.51-4.57 (d, 1H, J=16.0 Hz), 3.88-3.96 (m, 1H), 3.60-3.70 (m, 1H), 3.22-3.33 (m, 2H), 3.15 (s, 3H).

MS (EI) m/z: 198 (M)$^+$

Elementary analysis: as C$_8$H$_{11}$ClN$_2$O$_2$S,

Calculated: C, 40.94; H, 4.72; Cl, 15.11; N, 11.94; S, 13.66

Found: C, 40.50; H, 4.66; Cl, 15.31; N, 11.97; S, 13.68

Production Example 4

5-Methyl-4,5,6,7-tetrahydrothiazolo[5,4-c]pyridine-2-carboxylic acid hydrochloride

[F76]

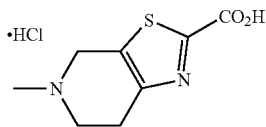

To 2-cyano-5-methyl-4,5,6,7-tetrahydrothiazolo[5,4-c]pyridine (199.30 mg) were added ethanol (2 mL) and 4N aqueous lithium hydroxide (0.42 mL) at room temperature, and the mixture was stirred at 50° C. for 10 hours. The reaction mixture was cooled with ice-water, and 1N HCl in ethanol (2.8 mL) was added thereto, to thereby form a hydrochloride salt. The precipitated crystals were collected by filtration, and were washed with ethanol (1 mL). The wet matter was dried at room temperature under reduced pressure, to thereby give 215.37 mg of the title compound.

$^1$'-NMR ($D_2O$) δ ppm: 4.82-4.88 (d, 1H, J=16.0 Hz), 4.51-4.57 (d, 1H, J=16.0 Hz), 3.88-3.96 (m, 1H), 3.60-3.70 (m, 1H), 3.22-3.33 (m, 2H), 3.15 (s, 3H).

MS (EI) m/z: 198 (M)$^+$

Production Example 5

5-Methyl-4,5,6,7-tetrahydrothiazolo[5,4-c]pyridine

[F77]

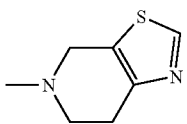

2-Amino-5-methyl-4,5,6,7-tetrahydrothiazolo[5,4-c]pyridine (10.00 g) was dissolved in a mixture of sulfuric acid (25 mL), hypophosphorous acid (50%, 13 mL), and water (100 mL) at 15 to 18° C., to thereby give an orange solution. To the solution was added dropwise a solution of sodium nitrite (8.15 g) in water (30 mL) at −2 to 3° C. over 30 minutes. After the resultant mixture was stirred at 0 to 10° C. for 2.5 hours, 8N aqueous potassium hydroxide (130 mL) was added dropwise thereto, and the pH was found to be 12.6. The precipitated potassium sulfate was filtered off, and was washed with ethyl acetate (200 mL). The aqueous layer was separated from the filtrate, and was further extracted with ethyl acetate twice (200 mL×2). The organic layers were combined, and the combined organic layer was dried over sodium sulfate anhydrate (30.00 g). After any insoluble material was filtered off and washed with ethyl acetate (100 mL), the filtrate was concentrated under reduced pressure, to thereby give 6.15 g of the title compound.

$^1$H-NMR (CDCl$_3$) δ ppm: 8.62 (s, 1H), 3.71-3.67 (t, 2H, J=1.7 Hz), 3.01-2.95 (dt, 2H, J=1.7 Hz, 5.9 Hz), 2.84-2.80 (t, 2H, J=5.9 Hz), 2.51 (s, 3H).

Production Example 6

5-Methyl-4,5,6,7-tetrahydrothiazolo[5,4-c]pyridine p-toluenesulfonic acid salt

[F78]

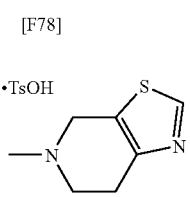

5-Methyl-4,5,6,7-tetrahydrothiazolo[5,4-c]pyridine (1.00 g) was dissolved in 2-propanol (10 mL) at room temperature, and p-toluenesulfonic acid monohydrate (1.23 g) was added thereto at room temperature, followed by stirring at room temperature for 20 minutes. When the resultant mixture was cooled to 0° C., a salt was crystallized out of the mixture. After the resultant mixture was stirred at 0° C. for 2 hours, the precipitated salt was collected by filtration, and was washed with 2-propanol (2 mmol). The wet material was dried at room temperature under reduced pressure, to thereby give 1.91 g of the title compound.

$^1$H-NMR ($D_2O$) δ ppm: 9.00 (s, 1H), 7.68-7.65 (d, 2H, J=8.1 Hz), 4.25-4.85 (br, 2H), 3.40-3.95 (br, 2H), 3.25-3.18 (t, 2H, J=6.0 Hz), 3.08 (s, 3H), 2.38 (s, 3H).

MS (EI) m/z: 154 (M)$^+$

Elementary analysis: as $C_{14}H_{18}N_2O_3S_2$,

Calculated: C, 51.51; H, 5.56; N, 8.58; S, 19.65

Found: C, 51.24; H, 5.52; N, 8.81; S, 19.37

Production Example 7

5-Methyl-4,5,6,7-tetrahydrothiazolo[5,4-c]pyridine-2-carboxylic acid hydrochloride

[F79]

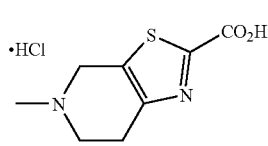

5-Methyl-4,5,6,7-tetrahydrothiazolo[5,4-c]pyridine (1.00 g) was dissolved in toluene (10 mL) at room temperature, and triethylamine (1.81 mL) and trichloroacetyl chloride (1.45 mL) were sequentially added thereto at room temperature, followed by stirring at room temperature for 4 hours. To the resultant mixture was added a solution of lithium hydroxide monohydrate (1.22 g) in water (10 mL), to thereby perform hydrolysis. The organic layer was separated from the aqueous layer, and was further extracted with water (10 mL). The aqueous layers were combined, and the combined aqueous layer was concentrated in a bath at 50° C. under reduced pressure. Ethanol (10 mL) was added thereto, and the resultant mixture was again concentrated under reduced pressure.

Ethanol (15 mL) was added to the concentrated residue, and the resultant mixture was cooled with ice-water. Concentrated hydrochloric acid (2.7 mL) was added dropwise thereto, to thereby form a hydrochloride salt, and the resultant mixture was stirred at the same temperature for 1.5 hours. The precipitated crystals were collected by filtration, and were washed with ethanol (4 mL). The wet matter was dried at room temperature under reduced pressure, to thereby give 1.25 g of the title compound.

$^1$H-NMR (D$_2$O) δ ppm: 4.82-4.88 (d, 1H, J=16.0 Hz), 4.51-4.57 (d, 1H, J=16.0 Hz), 3.88-3.96 (m, 1H), 3.60-3.70 (m, 1H), 3.22-3.33 (m, 2H), 3.15 (s, 3H)

MS (FAB) m/z: 199 (M+H)$^+$

Production Example 8

2-Amino-5-methyl-4,5,6,7-tetrahydrothiazolo[5,4-c]pyridine

[F80]

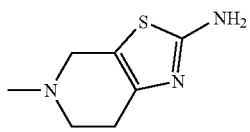

A solution of 1-methyl-4-piperidone (180.0 g) in 2-propanol (1.44 L) was heated to 50° C., and to the solution were sequentially added a solution of cyanamide (67.0 g) in 2-propanol (360 mL) and sulfur powder (51.0 g). After a catalytic amount of pyrrolidine (13.3 mL) was added thereto, the resultant mixture was stirred at or above 50° C. for 2 hours, and was allowed to cool to room temperature, followed by stirring overnight. The resultant mixture was cooled to or below 10° C. in an ice-water bath, and was stirred for 1 hour at the same temperature. The precipitated crystals were collected by filtration, and were washed with 2-propanol (540 mL) The wet crystal was dried at 40° C. under reduced pressure, to thereby give 209.9 g of the title compound.

$^1$H-NMR (CDCl$_3$) δ ppm: 4.86 (br, 2H), 3.47-3.46 (t, 2H, J=1.9 Hz), 2.78-2.71 (m, 2H), 2.71-2.65 (m, 2H), 2.47 (s, 3H).

MS (FAB) m/z: 170 (M+H)$^+$

Elementary analysis: as C$_7$H$_{11}$N$_3$S,

Calculated: C, 49.68; H, 6.55; N, 24.83; S, 18.95

Found: C, 49.70; H, 6.39; N, 24.91; S, 19.00

Production Example 9

2-Amino-5-methyl-4,5,6,7-tetrahydrothiazolo[5,4-c]pyridine dihydrobromide

[F81]

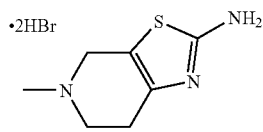

1-Methyl-4-piperidone (100.0 g) was dissolved in 2-propanol (800 mL) at room temperature, and the solution was heated to an internal temperature of 50° C. in a water bath. To the resultant mixture were sequentially added a solution of cyanamide (37.16 g) in 2-propanol (200 mL) and sulfur powder (28.34 g) at 50° C. A catalytic amount of pyrrolidine (7.4 mL) was added thereto, and the resultant mixture was stirred at 50 to 64° C. for 1 hour. After the resultant mixture was allowed to cool to room temperature, 48% hydrobromic acid (358.0 g) was added dropwise thereto at 30 to 40° C., and the mixture was cooled to or below 10° C. in an ice-water bath, followed by stirring at the same temperature for 1.5 hours. The precipitated crystals were collected by filtration, and were washed with 2-propanol (500 mL). The wet crystal was dried at 40° C. under reduced pressure, to thereby give 258.2 g of the title compound.

$^1$H-NMR (D$_2$O) δ ppm: 4.45-4.53 (d, 1H, J=15.2 Hz), 4.20-4.26 (d, 1H, J=15.2 Hz), 3.75-3.90 (m, 1H), 3.50-3.67 (m, 1H), 3.10 (s, 3H), 2.91-3.18 (m, 2H).

Elementary analysis: as C$_7$H$_{13}$Br$_2$N$_3$S,

Calculated: C, 25.39; H, 3.96; Br, 48.27; N, 12.69; S, 9.69

Found: C, 25.54; H, 3.93; Br, 48.09; N, 12.62; S, 9.72

Production Example 10

2-Bromo-5-methyl-4,5,6,7-tetrahydrothiazolo[5,4-c]pyridine

[F82]

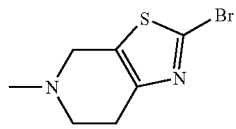

2-Amino-5-methyl-4,5,6,7-tetrahydrothiazolo[5,4-c]pyridine (600.0 g) was suspended in water (6.0 L), and 48% hydrobromic acid (4.2 L) was added dropwise thereto at 5 to 15° C. A solution of sodium nitrite (367.2 g) in water (1.8 L) was added dropwise thereto at 0 to 5° C. over 1.5 hours, and the reaction mixture was heated to 30° C., followed by stirring for 24 hours. The resultant mixture was made strongly basic (pH 12.5) with 5N aqueous sodium hydroxide (6.0 L). The aqueous layer was extracted with toluene twice (12.0 L, 6.0 L), and the toluene layers were combined. The combined toluene layer was dried over sodium sulfate anhydrate (1202.0 g), and after any insoluble material was filtered off, the mother liquor was concentrated at 40° C. under reduced pressure, to thereby give 557.6 g of the title compound.

$^1$H-NMR (CDCl$_3$) δ ppm: 3.58-3.57 (t, 3H, J=1.8 Hz), 2.92-2.87 (m, 2H), 2.81-2.76 (m, 2H), 2.49 (s, 3H).

Production Example 11

2-Bromo-5-methyl-4,5,6,7-tetrahydrothiazolo[5,4-c]pyridine p-toluenesulfonic acid salt

[F83]

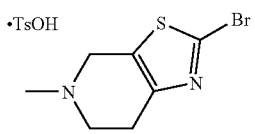

2-Bromo-5-methyl-4,5,6,7-tetrahydrothiazolo[5,4-c]pyridine (557.6 g) was dissolved in methanol (3.9 L), and to the solution was added dropwise a solution of p-toluenesulfonic acid monohydrate (500.0 g) in methanol (1.7 L) at 30° C. The resultant mixture was stirred at the same temperature for 1 hour, and then at or below 10° C. for 2 hours. The precipitated crystals were collected by filtration, and were washed with methanol (1.1 L), followed by drying at 40° C. under reduced pressure, to thereby give 851.9 g of the title compound.

$^1$H-NMR (DMSO-d$_6$) δ ppm: 10.15 (br, 1H), 7.47-7.43 (d, 2H, J=8.2 Hz), 7.09-7.07 (d, 2H, J=8.2 Hz), 4.47 (s, 2H), 3.58 (s, 2H) 3.04 (t, 2H, J=6.1 Hz), 2.96 (s, 3H), 2.29 (s, 3H).

Elementary analysis: as $C_{14}H_{17}BrN_2O_3S_2$,
Calculated: C, 41.48; H, 4.23; Br, 19.71; N, 6.91; S, 15.82
Found: C, 41.52; H, 4.33; Br, 19.80; N, 6.99; S, 15.90

Production Example 12

2-Bromo-5-methyl-4,5,6,7-tetrahydrothiazolo[5,4-c]pyridine p-toluenesulfonic acid salt

[F84]

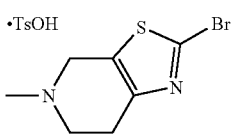

2-Amino-5-methyl-4,5,6,7-tetrahydrothiazolo[5,4-c]pyridine dihydrobromide (50.01 g) was suspended in a mixture of water (250 mL) and 48% hydrobromic acid (175 mL) at room temperature. After the suspension was cooled to an internal temperature of 10° C. or lower, a solution of sodium nitrite (15.63 g) in water (75 mL) was added dropwise thereto over 1.5 hours while the internal temperature was kept at or below 10° C. After the resultant mixture was stirred at or below 10° C. for 20 hours, 10N aqueous sodium hydroxide (175 mL) was added dropwise thereto while being kept at or below 20° C., to thereby make the solution basic, and the pH of the resultant solution was found to be 13.1. Subsequently, the aqueous layer was extracted with toluene twice (375 mL, 250 mL), and the toluene layers were combined. A quarter of the amount of the combined toluene layer was used for the following procedures. The toluene layer was concentrated, and the concentrated residue was dissolved in methanol (43.8 mL). A solution of p-toluenesulfonic acid monohydrate (5.03 g) in methanol (18.8 mL) was added dropwise thereto at room temperature, and the mixture was cooled to or below 10° C., followed by stirring at the same temperature for 1.5 hours. The precipitated crystals were collected by filtration, and were washed with methanol (18.8 mL). The wet crystal was dried at 40° C. under reduced pressure, to thereby give 9.05 g of the title compound.

$^1$H-NMR (DMSO-d$_6$) δ ppm: 10.15 (br, 1H), 7.47-7.43 (d, 2H, J=8.2 Hz), 7.09-7.07 (d, 2H, J=8.2 Hz), 4.47 (s, 2H), 3.58 (s, 2H), 3.04 (t, 2H, J=6.1 Hz), 2.96 (s, 3H), 2.29 (s, 3H).

Elementary analysis: as $C_{14}H_{17}BrN_2O_3S_2$,
Calculated: C, 41.48; H, 4.23; Br, 19.71; N, 6.91; S, 15.82
Found: C, 41.54; H, 4.18; Br, 19.83; N, 7.03; S, 16.02

Production Example 13

Lithium 5-methyl-4,5,6,7-tetrahydrothiazolo[5,4-c]pyridine-2-carboxylate

[F85]

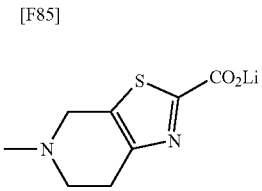

To 2-bromo-5-methyl-4,5,6,7-tetrahydrothiazolo[5,4-c]pyridine p-toluenesulfonic acid salt (490.0 g) was added 2N aqueous sodium hydroxide (2.45 L), and the mixture was stirred at room temperature for 30 minutes. The resultant mixture was extracted with toluene twice (4.9 L×2), and the organic layer was dried over sodium sulfate anhydrate (979.8 g). After any insoluble material was filtered off, the mother liquor was concentrated at or below 40° C. under reduced pressure, to thereby give 2-bromo-5-methyl-4,5,6,7-tetrahydrothiazolo[5,4-c]pyridine (284.0 g) as a brown oily compound. The resultant 2-bromo-5-methyl-4,5,6,7-tetrahydrothiazolo[5,4-c]pyridine (284.0 g) was dissolved in anhydrous tetrahydrofuran (2.84 L). After the system was purged with argon, n-Butyllithium (as 1.59 mol/L n-hexane solution, 766 mL) was added dropwise to the solution at −40 to −30° C., and the resultant mixture was stirred at the same temperature for 1 hour. After passing carbon dioxide gas through the reaction mixture at −40 to −25° C., the mixture was stirred under carbon dioxide atmosphere at the same temperature for 1 hour. The resultant mixture was heated to room temperature, and ethyl acetate (1.42 L) was added thereto. The precipitated solid was filtered off, and was washed with ethyl acetate (0.85 L). The thus-obtained solid material was dried at 40° C. under reduced pressure, and was pulverized, to thereby give 235.1 g of the title compound.

$^1$H-NMR (DMSO-d$_6$) δ ppm: 3.54 (s, 2H), 2.65-2.85 (m, 4H), 2.36 (s, 3H).

Production Example 14

5-Methyl-4,5,6,7-tetrahydrothiazolo[5,4-c]pyridine-2-carboxylic acid hydrochloride

[F86]

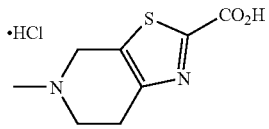

To lithium 5-methyl-4,5,6,7-tetrahydrothiazolo[5,4-c]pyridine-2-carboxylate (3.00 g) was added 1N HCl in ethanol (36 mL), and the mixture was stirred at room temperature for 1 hour. The precipitated crystals were collected by filtration, and were washed with ethanol (9 mL). The wet crystal was dried at room temperature under reduced pressure, to thereby give 2.76 g of the title compound.

$^1$H-NMR (D$_2$O) δ ppm: 4.82-4.88 (d, 1H, J=16.0112), 4.51-4.57 (d, 1H, J=16.0 Hz), 3.88-3.96 (m, 1H), 3.60-3.70 (m, 1H), 3.22-3.33 (m, 2H), 3.15 (s, 3H).

Elementary analysis: as $C_8H_{11}ClN_2O_2S$,
Calculated: C, 40.94; H, 4.72; N, 11.94; S, 13.66
Found: C, 40.51; H, 4.65; N, 11.79; S, 13.53

Production Example 15

5-Methyl-4,5,6,7-tetrahydrothiazolo[5,4-c]pyridine-2-carboxylic acid hydrochloride

[F87]

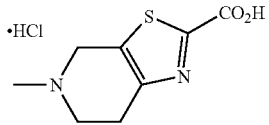

2-Bromo-5-methyl-4,5,6,7-tetrahydrothiazolo[5,4-c]pyridine p-toluenesulfonic acid salt (40.00 g) was mixed with 1N aqueous sodium hydroxide (200 mL) at room temperature, and the mixture was stirred for 30 minutes. The aqueous layer was extracted with toluene twice (400 mL×2), and the organic layers were combined. The combined organic layer was washed with 5% brine (200 mL), and was concentrated to 80 mL at an external temperature of 50° C. or lower under reduced pressure. A sample for water content measurement was taken from the resultant mixture (weight of the mixture after concentration: 91.03 g, weight of the mixture after sampling: 87.68 g). The sample of the concentrated mixture was subjected to water content measurement with Karl-Fischer Moisture Titrator, and the water content was found to be 0.0231% (on a weight-to-weight ratio). The remaining portion of the concentrated mixture after sampling was dissolved in anhydrous tetrahydrofuran (231 mL). After the system was purged with argon, the reaction mixture was cooled to an internal temperature of −30° C. or lower, and to the solution was added dropwise n-butyllithium (as 1.59 mol/L n-hexane solution, 61.7 mL) while the internal temperature was kept at or below −30° C., followed by stirring at the same temperature for 1 hour. After passing carbon dioxide gas through the resultant mixture while the internal temperature was kept at or below −30° C., the reaction mixture was stirred under carbon dioxide atmosphere for 1 hour. The resultant mixture was heated to an internal temperature of 15° C., and methanol (193 mL) was added thereto, to thereby dissolve the precipitated solid, and concentrated hydrochloric acid (19.3 mL) was added dropwise thereto while the internal temperature was kept at or below 20° C. The resultant mixture was cooled to an internal temperature of 10° C. or lower, and was stirred at the same temperature for 1 hour. The precipitated crystals were collected by filtration, and were washed with methanol (58 mL) The wet crystal was dried at room temperature under reduced pressure, to thereby give 21.20 g of the title compound.

$^1$H-NMR (D$_2$O) δ ppm: 4.82-4.88 (d, 1H, J=16.0 Hz), 4.51-4.57 (d, 1H, J=16.0 Hz), 3.88-3.96 (m, 1H), 3.60-3.70 (m, 1H), 3.22-3.33 (m, 2H), 3.15 (s, 3H).

MS (EI) m/z: 198 (M)$^+$

Elementary analysis: as $C_8H_{11}ClN_2O_2S$,
Calculated: C, 40.94; H, 4.72; Cl, 15.11; N, 11.94; S, 13.66
Found: C, 40.33; H, 4.56; Cl, 14.81; N, 11.91; S, 13.87

Production Example 16

N$^1$-(5-Chloropyridin-2-yl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide

[F88]

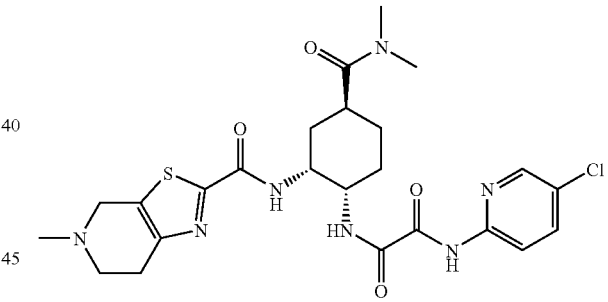

N$^1$-{(1S,2R,4S)-2-Amino-4-[(dimethylamino)carbonyl]cyclohexyl}-N$^2$-(5-chloropyridin-2-yl)ethanediamide (553.4 mg) was dissolved in dimethylacetamide (7 mL), and to the solution were added 1-hydroxybenzotriazole monohydrate (245.1 mg), 5-methyl-4,5,6,7-tetrahydrothiazolo[5,4-c]pyridine-2-carboxylic acid hydrochloride (386.0 mg), and 1-(3-dimethylaminopropyl)-3-ethylcarbodiimide hydrochloride (345.0 mg) at room temperature. The resultant mixture was stirred for 13 hours, and triethylamine and water were added thereto. The precipitated crystals were collected by filtration, and were dried, to thereby give 674.1 mg of the title compound.

$^1$H-NMR (CDCl$_3$) δ ppm: 1.60-1.98 (3H, m), 2.00-2.16 (3H, m), 2.52 (3H, s), 2.78-2.90 (3H, m), 2.92-2.98 (2H, m), 2.95 (3H, s), 3.06 (3H, s), 3.69 (1H, d, J=15.4 Hz), 3.75 (1H, d, J=15.4 Hz), 4.07-4.15 (1H, m), 4.66-4.72 (1H, m), 7.40 (1H, d, J=8.8, 0.6 Hz), 7.68 (1H, dd, J=8.8, 2.4 Hz), 8.03 (1H, d, J=7.8 Hz), 8.16 (1H, dd, J=8.8, 0.6 Hz), 8.30 (1H, dd, J=2.4, 0.6 Hz), 9.72 (1H, s). MS (ESI) m/z: 548 (M+H)$^+$.

The invention claimed is:

1. A process for producing 5-methyl-4,5,6,7-tetrahydrothiazolo[5,4-c]pyridine of formula (6) or a salt thereof, comprising:

[F13]

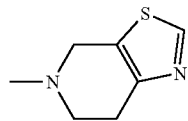

(6)

reacting 2-amino-5-methyl-4,5,6,7-tetrahydrothiazolo[5,4-c]pyridine of formula (2) or a salt thereof,

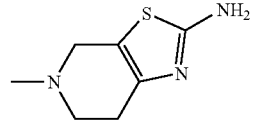

(2)

with an alkali metal nitrite in the presence of a reducing agent in an aqueous solution of an acidic compound.

2. The process according to claim 1, wherein the reducing agent is hypophosphorous acid.

3. The process according to claim 1, wherein the alkali metal nitrite is sodium nitrite.

* * * * *

UNITED STATES PATENT AND TRADEMARK OFFICE
CERTIFICATE OF CORRECTION

PATENT NO. : 7,880,005 B2  
APPLICATION NO. : 12/631002  
DATED : February 1, 2011  
INVENTOR(S) : Hiroshi Nagasawa et al.

It is certified that error appears in the above-identified patent and that said Letters Patent is hereby corrected as shown below:

Title Page and col. 1
Item 54 should read -- PROCESS FOR PRODUCING 5-METHYL-4,5,6,7-TETRAHYDROTHIAZOLO[5,4-c]PYRIDINE-2-CARBOXYLIC ACID --

Signed and Sealed this
Third Day of May, 2011

David J. Kappos
*Director of the United States Patent and Trademark Office*